US008911964B2

(12) United States Patent
Pla et al.

(10) Patent No.: US 8,911,964 B2
(45) Date of Patent: *Dec. 16, 2014

(54) FED-BATCH METHOD OF MAKING HUMAN ANTI-TNF-ALPHA ANTIBODY

(71) Applicant: AbbVie Inc., North Chicago, IL (US)

(72) Inventors: Itzcoatl A. Pla, Worcester, MA (US); Joseph G. Matuck, Worcester, MA (US); John C. Fann, Shrewsbury, MA (US); Christof Schulz, Ayer, MA (US); Nichole A. Roy, Worcester, MA (US); David F. Bruton, Enfield, CT (US); James McIntire, Castro Valley, CA (US); Yu-Hsiang David Chang, Solana Beach, CA (US); Thomas Seewoester, Simi Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/226,579

(22) Filed: Mar. 26, 2014

(65) Prior Publication Data

US 2014/0234905 A1    Aug. 21, 2014

Related U.S. Application Data

(63) Continuation-in-part of application No. 14/195,588, filed on Mar. 3, 2014, now abandoned, which is a continuation of application No. 13/308,075, filed on Nov. 30, 2011, now Pat. No. 8,663,945, which is a continuation of application No. 11/901,274, filed on Sep. 13, 2007, now Pat. No. 8,093,045.

(60) Provisional application No. 60/876,374, filed on Dec. 21, 2006, provisional application No. 60/845,158, filed on Sep. 13, 2006.

(51) Int. Cl.

| G01N 1/30 | (2006.01) |
| G01N 33/48 | (2006.01) |
| C12P 21/04 | (2006.01) |
| C12N 5/07 | (2010.01) |
| C12N 5/16 | (2006.01) |
| C12N 5/10 | (2006.01) |
| C12N 5/00 | (2006.01) |
| C12N 5/02 | (2006.01) |
| C07K 16/24 | (2006.01) |

(52) U.S. Cl.
CPC ............ *C07K 16/241* (2013.01); *C12N 5/0037* (2013.01)
USPC ........... 435/41; 435/69.6; 435/70.3; 435/326; 435/358; 435/404

(58) Field of Classification Search
CPC .......... C12N 1/04; C12N 5/0681; C12N 5/16; C12N 15/63; C12N 15/64; C12N 15/67; C12N 15/85; C12N 2015/85; C12N 2500/05; C12N 2500/32; C12N 2500/34; C12N 2500/60; C12N 2501/10
See application file for complete search history.

(56) References Cited

U.S. PATENT DOCUMENTS

| 5,045,468 | A | 9/1991 | Darfler |
| 5,096,816 | A | 3/1992 | Maiorella |
| 5,110,913 | A | 5/1992 | Coan et al. |
| 5,545,403 | A | 8/1996 | Page |
| 5,633,162 | A | 5/1997 | Keen et al. |
| 5,641,870 | A | 6/1997 | Rinderknecht et al. |
| 5,656,272 | A | 8/1997 | Le et al. |
| 5,672,502 | A | 9/1997 | Birch et al. |
| 5,705,364 | A | 1/1998 | Etcheverry et al. |
| 5,721,121 | A | 2/1998 | Etcheverry et al. |
| 5,811,299 | A | 9/1998 | Renner et al. |
| 5,876,961 | A | 3/1999 | Crowe et al. |
| 5,976,833 | A | 11/1999 | Furukawa et al. |
| 6,048,728 | A | 4/2000 | Inlow et al. |
| 6,090,382 | A | 7/2000 | Salfeld et al. |
| 6,127,526 | A | 10/2000 | Blank |
| 6,258,562 | B1 | 7/2001 | Salfeld et al. |
| 6,399,381 | B1 | 6/2002 | Blum et al. |
| 6,406,909 | B1 | 6/2002 | Shibuya et al. |
| 6,410,270 | B1 | 6/2002 | Strittmatter et al. |
| 6,413,746 | B1 | 7/2002 | Field |
| 6,448,380 | B2 | 9/2002 | Rathjen et al. |
| 6,451,983 | B2 | 9/2002 | Rathjen et al. |
| 6,498,237 | B2 | 12/2002 | Rathjen et al. |
| 6,509,015 | B1 | 1/2003 | Salfeld et al. |
| 6,528,286 | B1 | 3/2003 | Ryll |
| 6,680,181 | B2 | 1/2004 | Castan |
| 6,693,173 | B2 | 2/2004 | Mamidi et al. |
| 6,870,034 | B2 | 3/2005 | Breece et al. |

(Continued)

FOREIGN PATENT DOCUMENTS

| EP | 0481791 A2 | 4/1992 |
| EP | 1745141 B1 | 1/2010 |

(Continued)

OTHER PUBLICATIONS

Sandadi S, et al. Biotechnol. Prog. 21:1537-1542, 2005.*
SIGMA product information sheet. "CHO DHFR—Medium". Three pages. Oct. 2003.*
Sung H, et al. Applied Microbiology and Biotechnology. 63(5):527-536, Feb. 2004.*
Heidemann R, et al. Cytotechnology. 32:157-167, 2000.*
Altamirano C, et al. Biotechnol. Bioeng. 76:351-360, 2001.*
U.S. Appl. No. 12/910,461, filed Oct. 22, 2010, Salfeld et al.
Altamirano, C., et al., "Strategies for fed batch cultivation of t-PA producing CHO cells: substitution of glucose and glutamine and rational design of culture medium," J. Biotechn. 110:171-179, 2004.

(Continued)

Primary Examiner — Robert Landsman
(74) Attorney, Agent, or Firm — Foley Hoag LLP

(57) ABSTRACT

The invention describes improved methods and compositions for producing a recombinant protein, e.g., an antibody, in mammalian cell culture. In addition, the invention provides improved cell culture media, including improved production media, feed solutions, and combination feeds, which may be used to improve protein productivity in mammalian cell culture.

30 Claims, 1 Drawing Sheet

(56) References Cited

U.S. PATENT DOCUMENTS

| | | | |
|---|---|---|---|
| 6,872,549 B2 | 3/2005 | Van Ness et al. | |
| 6,890,736 B1 | 5/2005 | Reddy et al. | |
| 6,914,128 B1 | 7/2005 | Salfeld et al. | |
| 6,924,124 B1 | 8/2005 | Singh | |
| 6,974,681 B1 | 12/2005 | McGrew | |
| 7,070,775 B2 | 7/2006 | Le et al. | |
| 7,074,404 B2 | 7/2006 | Basey et al. | |
| 7,122,641 B2 | 10/2006 | Vedantham et al. | |
| 7,189,820 B2 * | 3/2007 | Ruben | 530/387.3 |
| 7,192,584 B2 | 3/2007 | Le et al. | |
| 7,208,585 B2 | 4/2007 | Fong et al. | |
| 7,223,394 B2 | 5/2007 | Salfeld et al. | |
| 7,250,165 B2 | 7/2007 | Heavner et al. | |
| 7,276,239 B2 | 10/2007 | Le et al. | |
| 7,332,303 B2 | 2/2008 | Schilling et al. | |
| 7,390,660 B2 | 6/2008 | Behrendt et al. | |
| 7,429,491 B2 | 9/2008 | Luan et al. | |
| 7,485,704 B2 | 2/2009 | Fahrner et al. | |
| 7,504,485 B2 | 3/2009 | Salfeld et al. | |
| 7,521,206 B2 | 4/2009 | Heavner et al. | |
| 7,521,210 B2 | 4/2009 | Knudsen | |
| 7,541,031 B2 | 6/2009 | Salfeld et al. | |
| 7,588,761 B2 | 9/2009 | Salfeld et al. | |
| 7,645,609 B2 | 1/2010 | Follstad | |
| 7,714,122 B2 | 5/2010 | Nix et al. | |
| 7,767,207 B2 | 8/2010 | Ghayer et al. | |
| 7,820,799 B2 | 10/2010 | Godavarti et al. | |
| 7,883,704 B2 | 2/2011 | Salfeld et al. | |
| 7,947,471 B2 | 5/2011 | Knudsen | |
| 7,972,835 B2 | 7/2011 | Hitosugi et al. | |
| 8,058,407 B2 | 11/2011 | Sun et al. | |
| 8,067,182 B2 | 11/2011 | Kelley et al. | |
| 8,093,364 B2 | 1/2012 | Gagnon | |
| 8,163,551 B2 | 4/2012 | Alley et al. | |
| 8,192,951 B2 | 6/2012 | Wang et al. | |
| 8,209,132 B2 | 6/2012 | Bosques et al. | |
| 8,350,013 B2 | 1/2013 | Sun | |
| 8,361,797 B2 | 1/2013 | Osborne et al. | |
| 8,435,527 B2 | 5/2013 | Yumioka et al. | |
| 2002/0045207 A1 | 4/2002 | Krummen et al. | |
| 2002/0132299 A1 | 9/2002 | Field | |
| 2003/0049725 A1 | 3/2003 | Heavner et al. | |
| 2003/0050450 A1 | 3/2003 | Coffman et al. | |
| 2003/0096414 A1 | 5/2003 | Ciccarone et al. | |
| 2003/0157108 A1 | 8/2003 | Presta | |
| 2003/0175884 A1 | 9/2003 | Umana et al. | |
| 2003/0201229 A1 | 10/2003 | Siwak et al. | |
| 2004/0029229 A1 | 2/2004 | Reeves et al. | |
| 2004/0033562 A1 | 2/2004 | Miller | |
| 2004/0120952 A1 | 6/2004 | Knight et al. | |
| 2004/0132140 A1 | 7/2004 | Satoh et al. | |
| 2004/0171152 A1 | 9/2004 | Price et al. | |
| 2004/0214289 A1 | 10/2004 | deVries et al. | |
| 2005/0004354 A1 | 1/2005 | Salfeld et al. | |
| 2005/0100965 A1 | 5/2005 | Ghayur et al. | |
| 2005/0107594 A1 | 5/2005 | Sun et al. | |
| 2005/0123541 A1 | 6/2005 | Heavner et al. | |
| 2005/0249735 A1 | 11/2005 | Le et al. | |
| 2005/0272124 A1 | 12/2005 | Chen et al. | |
| 2006/0018907 A1 | 1/2006 | Le et al. | |
| 2006/0246073 A1 | 11/2006 | Knight et al. | |
| 2007/0004009 A1 | 1/2007 | Dixit et al. | |
| 2007/0110743 A1 | 5/2007 | Drapeau et al. | |
| 2007/0111284 A1 | 5/2007 | Ryll | |
| 2007/0161084 A1 | 7/2007 | Crowell et al. | |
| 2007/0184529 A1 | 8/2007 | Etcheverry et al. | |
| 2007/0190057 A1 | 8/2007 | Wu et al. | |
| 2007/0196373 A1 | 8/2007 | Le et al. | |
| 2007/0213513 A1 | 9/2007 | Van Alstine et al. | |
| 2007/0298040 A1 | 12/2007 | Le et al. | |
| 2008/0025976 A1 | 1/2008 | Le et al. | |
| 2008/0219952 A1 | 9/2008 | Fischer et al. | |
| 2008/0269132 A1 | 10/2008 | Gomes et al. | |
| 2008/0269468 A1 | 10/2008 | Vogel et al. | |
| 2008/0274507 A1 | 11/2008 | Gomes et al. | |
| 2008/0305114 A1 | 12/2008 | Salfeld et al. |
| 2008/0311078 A1 | 12/2008 | Gokarn et al. |
| 2009/0053786 A1 | 2/2009 | Kao et al. |
| 2009/0068705 A1 | 3/2009 | Drapeau et al. |
| 2009/0142828 A1 | 6/2009 | Bucciarelli et al. |
| 2009/0175857 A1 | 7/2009 | Salfeld et al. |
| 2009/0203055 A1 | 8/2009 | Ngantung et al. |
| 2009/0208500 A1 | 8/2009 | Joly et al. |
| 2009/0269302 A1 | 10/2009 | Salfeld et al. |
| 2009/0291062 A1 | 11/2009 | Fraunhofer et al. |
| 2010/0221823 A1 | 9/2010 | McCoy et al. |
| 2010/0234577 A1 | 9/2010 | Mazzola et al. |
| 2010/0256336 A1 | 10/2010 | Yuk et al. |
| 2011/0003338 A1 | 1/2011 | Bayer et al. |
| 2011/0053223 A1 | 3/2011 | Bayer et al. |
| 2011/0053265 A1 | 3/2011 | Follstad et al. |
| 2011/0081679 A1 | 4/2011 | Jing et al. |
| 2011/0086798 A1 | 4/2011 | Sethuraman et al. |
| 2011/0097336 A1 | 4/2011 | Wu et al. |
| 2011/0130544 A1 | 6/2011 | Ram et al. |
| 2011/0207676 A1 | 8/2011 | Callewaert et al. |
| 2011/0213126 A1 | 9/2011 | Gonzalez et al. |
| 2011/0236391 A1 | 9/2011 | Mahler et al. |
| 2012/0015438 A1 | 1/2012 | Schilling et al. |
| 2012/0039908 A1 | 2/2012 | Combs et al. |
| 2012/0053325 A1 | 3/2012 | Gronke et al. |
| 2012/0077963 A1 | 3/2012 | Hongo et al. |
| 2012/0122759 A1 | 5/2012 | Brown et al. |
| 2012/0149878 A1 | 6/2012 | Gillespie et al. |
| 2012/0183997 A1 | 7/2012 | Alley et al. |
| 2012/0190005 A1 | 7/2012 | Schaub et al. |
| 2012/0201831 A1 | 8/2012 | Salfeld et al. |
| 2012/0208986 A1 | 8/2012 | Wenger et al. |
| 2012/0213792 A1 | 8/2012 | Salfeld et al. |
| 2012/0244168 A1 | 9/2012 | Salfeld et al. |
| 2012/0277165 A1 | 11/2012 | Collins et al. |
| 2012/0283416 A1 | 11/2012 | Frauenschuh et al. |
| 2012/0283419 A1 | 11/2012 | Thiyagarajan et al. |
| 2012/0288494 A1 | 11/2012 | Borhani et al. |
| 2012/0308514 A1 | 12/2012 | Salfeld et al. |
| 2013/0041139 A1 | 2/2013 | Brown et al. |
| 2013/0065219 A1 | 3/2013 | Tsang et al. |
| 2013/0084605 A1 | 4/2013 | Zhou et al. |
| 2013/0096283 A1 | 4/2013 | Khetan et al. |

FOREIGN PATENT DOCUMENTS

| | | | |
|---|---|---|---|
| EP | 2357250 A2 | 8/2011 |
| EP | 1851305 B1 | 1/2012 |
| EP | 2144929 B1 | 1/2012 |
| EP | 2080809 B1 | 2/2012 |
| EP | 2152856 B1 | 8/2012 |
| EP | 2495307 A1 | 9/2012 |
| EP | 2528002 A2 | 11/2012 |
| EP | 2213726 B1 | 12/2012 |
| EP | 2574677 A1 | 4/2013 |
| WO | WO-97/29131 A1 | 8/1997 |
| WO | WO-99/32605 A1 | 7/1999 |
| WO | WO-99/57246 A1 | 11/1999 |
| WO | WO-00/03000 A2 | 1/2000 |
| WO | WO-01/77362 A1 | 10/2001 |
| WO | WO-02/12501 A2 | 2/2002 |
| WO | WO-02/12502 A2 | 2/2002 |
| WO | WO-03/045995 A2 | 6/2003 |
| WO | WO-2004/008100 A2 | 1/2004 |
| WO | WO-2004/058800 A2 | 7/2004 |
| WO | WO-2004/058944 A2 | 7/2004 |
| WO | WO-2006/045438 A1 | 5/2006 |
| WO | WO-2007/087384 A2 | 8/2007 |
| WO | WO-2008/068879 A1 | 6/2008 |
| WO | WO-2008/121616 A2 | 10/2008 |
| WO | WO-2008/135498 A2 | 11/2008 |
| WO | WO-2009/023562 A2 | 2/2009 |
| WO | WO-2009/058812 A1 | 5/2009 |
| WO | WO-2010/036443 A1 | 4/2010 |
| WO | WO-2010/072381 A1 | 7/2010 |
| WO | WO-2010/080062 A1 | 7/2010 |
| WO | WO-2010/120739 A1 | 10/2010 |
| WO | WO-2010/122460 A1 | 10/2010 |

(56) References Cited

FOREIGN PATENT DOCUMENTS

| | | |
|---|---|---|
| WO | WO-2011/005773 A2 | 1/2011 |
| WO | WO-2011/009623 A1 | 1/2011 |
| WO | WO-2011/015926 A1 | 2/2011 |
| WO | WO-2011/024025 A1 | 3/2011 |
| WO | WO-2011/031397 A1 | 3/2011 |
| WO | WO-2011/044180 A1 | 4/2011 |
| WO | WO-2011/069056 A2 | 6/2011 |
| WO | WO-2011/081898 A1 | 7/2011 |
| WO | WO-2011/127322 A1 | 10/2011 |
| WO | WO-2011/134919 A2 | 11/2011 |
| WO | WO-2011/134920 A1 | 11/2011 |
| WO | WO-2012/019160 A1 | 2/2012 |
| WO | WO-2012/030512 A1 | 3/2012 |
| WO | WO-2012/050175 A1 | 4/2012 |
| WO | WO-2012/062810 A2 | 5/2012 |
| WO | WO-2012/084829 A1 | 6/2012 |
| WO | WO-2012/120500 A2 | 9/2012 |
| WO | WO-2012/134987 A1 | 10/2012 |
| WO | WO-2012/140138 A1 | 10/2012 |
| WO | WO-2012/145682 A1 | 10/2012 |
| WO | WO-2012/147048 A2 | 11/2012 |
| WO | WO-2012/158551 A1 | 11/2012 |
| WO | WO-2013/006461 A1 | 1/2013 |
| WO | WO-2013/006479 A2 | 1/2013 |
| WO | WO-2013/009648 A2 | 1/2013 |
| WO | WO-2013/013013 A2 | 1/2013 |
| WO | WO-2013/057078 A1 | 4/2013 |

OTHER PUBLICATIONS

Ballez, J.S. et al., "Plant protein hydrolysates support CH0-320 cells proliferation and recombinant IFN-[gamma] production in suspension and inside microcarriers in protein-free media," Cytotechnology 44:3, 103-114, 2004.

Biblia TA, et al., "In Pursuit of Optimal Fed-Batch Process for Monoclonal Antibody Production," Biotechnol. Prog. 11 (1 ):1-13, Jan.-Feb. 1995.

Birch, Jr. et al., "Antibody production", Adv. Drug Delivery Reviews 58:671-685, 2006.

Blaker, GJ, et al., "The Glucose, Insulin and Glutamine Requirements of Suspension Cultures of Hela Cells in a Defined Culture Medium", J. Cell Sci. 9:529-537, 1971.

Bollati-Fogolin M., et al., "Temperature Reduction in Cultures of hGM-CSF-expressing CHO Cells: Effects on Productivity and Product Quantity", Biotechnol. Prog. 21 :17-21, 2005.

Chang KH, et al., "N-Acetylcysteine Increases the Biosynthesis of Recombinant EPO in Apoptotic Chinese Hamster Ovary Cells", Free Radic Res. 30(2):85-91, 1999.

Chua FKF, et al., "Hyper-Simulation of monoclonal antibody production by high osmolarity stress in eRDF medium," J. Biotechnology 37(3):265-275, Nov. 15, 1994.

Gatto, B. "Biologics targeted at TNF: design, production and challenges", Reumatismo 58(2): 94-1 03, 2006.

Grunberg, J. et al., "High-Yield Production of Recombinant Antibody Fragments in HEK-293 Cells Using Sodium Butyrate", BioTechniques 34(5):968-972, May 2003.

Han Kyu Oh et al., "Effect of N-Acetylcysteine on Butyrate-Treated Chinese Hamster Ovary Cells to Improve the Production of Recombinant Human Interferon-β-1a", Biotechnol. Prog. 21 (4): 1154-1164, 2005.

Heidemann R, et al., "The use of peptones as medium additives for the production of a recombinant therapeutic protein in high density perfusion cultures of mammalian cells," Cytotechnology. 32:157-167, 2000.

Kazuaki, F. et al., "Enhancement of productivity of recombinant alpha-amidating enzyme by low temperature culture", Cytotechnology 31 :85-94, 1999.

Kim, NS. et al., "Inhibition of sodium butyrate-induced apoptosis in recombinant Chinese hamster ovary cells by constitutively expressing antisense RNA of caspase-3", Biotechn. & Bioengin. 78(2):217-228, 2002.

Meuwly, F. et al., "Conversion of a CHO cell culture process from perfusion to fed-batch technology without altering product quality", J. Biotechn. 123:106-116, 2006.

Moore, A., et al., "Effects of temperature shift on cell cycle, apoptosis and nucleotide pools in CHO cell batch cultures", Cytotechnology, 23:47-54, 1997.

Oh, D-K. et al., "Increased erythritol production in fed-batch cultures of *Torula* sp. by controlling glucose concentration", J. Industrial Microb. & Biotechn. 26(4): 248-252, 2001.

Oh, Skw, et al., "Substantial Overproduction of Antibodies by Applying Osmotic Pressure and Sodium Butyrate", Biotechn. Bioengin. 42(5):601-610, 1993.

Reichert JM., et al., "Monoclonal antibody successes in the clinic", Nature Biotech. 23(9):1073-1078, 2005.

Rheinwald Jg, et al., "Growth of Cultured Mammalian Cells on Secondary Glucose Sources", Cell, 287-293, 1974.

Sandadi, S. et al., "Heuristic Optimization of Antibody Production by Chinese Hamster Ovary Cells", Biotech. Progress, American Institute of Chem. Engineers, 21 (5): 1537-1542, 2005.

SIGMA product information sheet. "CHO DHFR-Medium". Three pages. Oct. 2003.

Sung Y H et al., "Yeast hydrolysate as a low-cost additive to serum-free medium for the production of human thrombpoietin in suspension cultures of Chinese hamster ovary cells," Applied Microbiology and Biotechnology 63:5, 527-536, 2004.

Takagi M, et al., "The effect of osmolarity on metabolism and morphology in adhesion and suspension Chinese hamster ovary cells producing tissue plasminogen activator," Cytotechnology 32:171-179, 2000.

Wurm, FM, "Production of recombinant protein therapeutics in cultivated mammalian cells", Nature Biotechnology 22(11 ):1393-1398, 2004.

\* cited by examiner

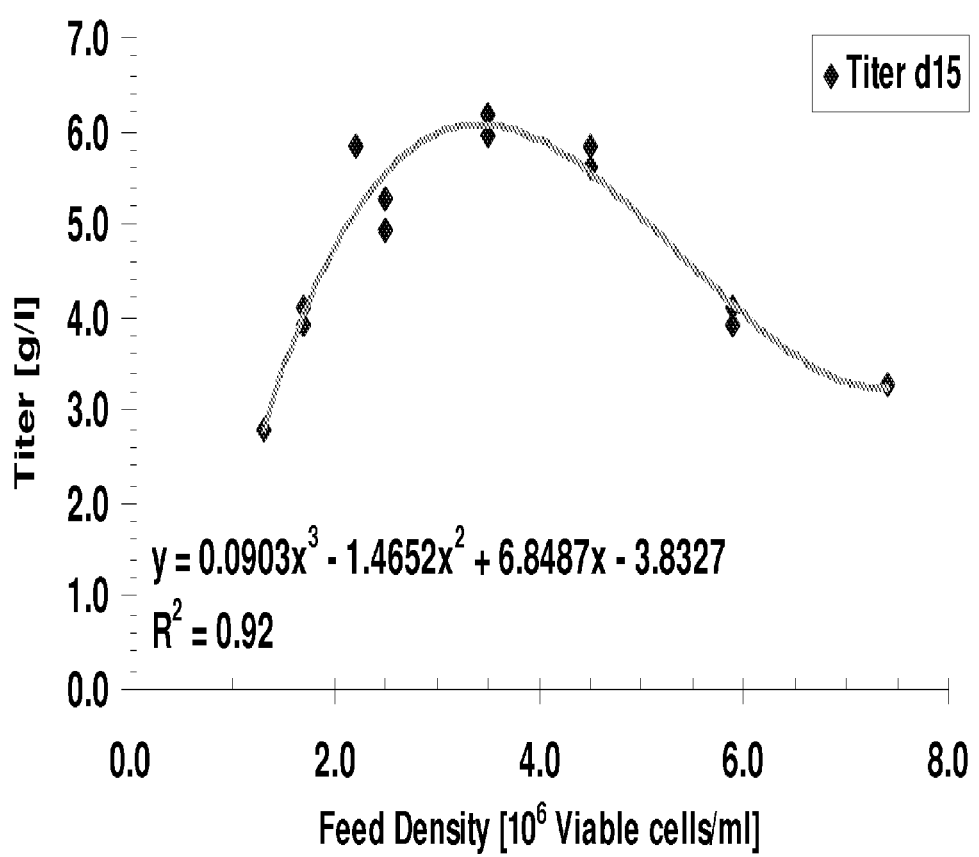

SEQUENCE LISTING

<160> NUMBER OF SEQ ID NOS: 8

<210> SEQ ID NO 1
<211> LENGTH: 107
<212> TYPE: PRT
<213> ORGANISM: Artificial Sequence
<220> FEATURE:
<223> OTHER INFORMATION: Variable light chain

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

```
Tyr Ala Ala Ser Thr Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
                100                 105

<210> SEQ ID NO 2
<211> LENGTH: 121
<212> TYPE: PRT
<213> ORGANISM: Artificial Sequence
<220> FEATURE:
<223> OTHER INFORMATION: Variable heavy chain

<400> SEQUENCE: 2

Glu Val Gln Leu Val Glu Ser Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
        50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser
            115                 120

<210> SEQ ID NO 3
<211> LENGTH: 9
<212> TYPE: PRT
<213> ORGANISM: Artificial Sequence
<220> FEATURE:
<223> OTHER INFORMATION: Variable light chain CDR3
<220> FEATURE:
<221> NAME/KEY: VARIANT
<222> LOCATION: (9)..(9)
<223> OTHER INFORMATION: Xaa = Thr or Ala

<400> SEQUENCE: 3

Gln Arg Tyr Asn Arg Ala Pro Tyr Xaa
 1               5

<210> SEQ ID NO 4
<211> LENGTH: 12
<212> TYPE: PRT
<213> ORGANISM: Artificial Sequence
<220> FEATURE:
<223> OTHER INFORMATION: Variable heavy chain CDR3
<220> FEATURE:
<221> NAME/KEY: VARIANT
<222> LOCATION: (12)..(12)
<223> OTHER INFORMATION: Xaa=Tyr or Asn

<400> SEQUENCE: 4

Val Ser Tyr Leu Ser Thr Ala Ser Ser Leu Asp Xaa
```

```
<210> SEQ ID NO 5
<211> LENGTH: 7
<212> TYPE: PRT
<213> ORGANISM: Artificial Sequence
<220> FEATURE:
<223> OTHER INFORMATION: Variable light chain CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: Variable heavy chain CDR2

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: Variable light chain CDR1

<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Variable heavy chain CDR1

<400> SEQUENCE: 8

Asp Tyr Ala Met His
1               5
```

US 8,911,964 B2

FED-BATCH METHOD OF MAKING HUMAN ANTI-TNF-ALPHA ANTIBODY

RELATED APPLICATIONS

This application is a continuation-in-part of U.S. patent application Ser. No. 14/195,588, which was filed on Mar. 3, 2014 as a continuation of U.S. patent application Ser. No. 13/308,075, filed Nov. 30, 2011 and now U.S. Pat. No. 8,663,945, which is a continuation of U.S. patent application Ser. No. 11/901,274, filed Sep. 13, 2007 and now U.S. Pat. No. 8,093,045, which claims the benefit of priority to U.S. Provisional Application No. 60/845,158, filed on Sep. 13, 2006, and U.S. Provisional Application No. 60/876,374, filed on Dec. 21, 2006. The contents of each of the above priority documents is incorporated by reference herein. This application also incorporates by reference U.S. Pat. Nos. 8,093,045 and 8,663,995 and U.S. Patent Application Publication Nos. 2008/0227136 and 2012/0077213 in their entireties.

BACKGROUND OF THE INVENTION

Recombinant DNA technology has provided a means to produce proteins in amounts which allow for their use in a spectrum of applications, including therapeutic, diagnostic, agricultural, and research purposes.

One goal of recombinant protein production is the optimization of cell culture media and conditions in order to obtain the greatest amount of protein and the most efficient means of productivity. Any improvement, including incremental improvements, can have enormous benefits economically. In the pharmaceutical industry, optimization of protein production for biologics used in therapies for the treatment of disease is advantageous, as any improvement can have significant impact when the biologic is manufactured on a large scale. As such, there remains a need to maximize protein production from cell cultures expressing biologic proteins for use in medicine.

Typically mammalian cell culture media is based on commercially available media formulations, including, for example, DMEM or Ham's F12. Often media formulations are not sufficiently enriched to support increases in both cell growth and biologic protein expression. There remains a need for improved cell culture media, supplements, and cell culture methods for improved protein production.

SUMMARY OF THE INVENTION

The invention provides methods and compositions for improving protein expression in cell culture, particularly mammalian cell culture. The invention relates to improved cell culture media, including media for growing cells for protein expression and cell culture production media optimized for protein expression.

The invention also includes optimized methods and media formulations for high protein expression in mammalian cell culture. In particular, the cell culture media is optimized for expression of antibodies in mammalian cell culture, e.g., CHO cells. Improved fed batch methods and compositions for promoting protein production by adding supplemental solutions, e.g., hydrolysate containing solutions and concentration basal media solutions, are also provided.

The invention provides improved salt-free basal growth media for use in mammalian cell culture. The invention includes a serum-free cell culture medium comprising Part A, Part B, and Part C, wherein Part A consists essentially of a modified basal medium which excludes the following components: sodium bicarbonate, a buffer, mono-basic sodium phosphate, di-basic sodium phosphate, an osmolarity regulator, a surfactant, and monosaccharide glucose; Part B consists essentially of an inorganic iron source; and Part C comprises a recombinant growth factor; a buffer; an osmolarity regulator; an energy source; and at least two different non-animal hydrolysates.

In one embodiment, Part A further comprises non-ferrous metal ions, vitamins, or a combination of both. In one embodiment, the inorganic iron source of Part B is ferric citrate e.g., about 100-150 mg/L or 0.1-1 mM final solution concentration ferric citrate. In another embodiment, the inorganic iron source of Part B is ferric citrate e.g., about 122.5 mg/L or 0.5 mM final solution concentration ferric citrate.

In one embodiment, the recombinant growth factor of Part C is selected from the group consisting of insulin or a recombinant analog, IGF-1, and a combination of insulin and IGF-1, e.g., about 4 mg/L to 13 mg/L insulin, or a recombinant analog thereof.

In one embodiment, the buffer which is excluded from the modified basal medium is HEPES buffer.

In one embodiment, the buffer of Part C comprises a phosphate buffer, HEPES, and sodium bicarbonate, e.g., about 0.1 to 3 g/L sodium bicarbonate, about 0.1 to 3 g/L HEPES. In one embodiment, the buffer of Part C comprises 1.6 g/L of sodium bicarbonate and/or about 1.8 g/L HEPES. In one embodiment, the phosphate buffer comprises about 0.01 to 0.5 g/L mono- and di-basic sodium phosphates.

In a further embodiment, Part C further comprises asparagine, glutamine, or glutamine and asparagine.

In one embodiment, the osmolarity regulator of Part C is NaCl, e.g., about 1.0 to 6.5 g/L NaCl.

In one embodiment, the energy source of Part C is a monosaccharide, e.g., glucose (such as D-glucose), maltose, mannose, galactose and fructose. In one embodiment, the cell culture medium of the invention comprises no greater than about 7.0 g/L glucose.

In another embodiment, the cell culture medium of the invention comprises at least two different non-animal based hydrolysates of Part C are a plant-based hydrolysate and a hydrolysate which is neither animal or plant-based. An example of a plant-based hydrolysate that may be used in the invention is a soy-based hydrolysate. An example of a hydrolysate that is neither animal or plant-based is a yeast-based hydrolysate.

In one embodiment, the cell culture medium of the invention further comprises methotrexate. In one embodiment, the cell culture medium further comprises about 100 nM to 5000 nM methotrexate.

In yet another embodiment, the cell culture medium further comprises a cell protectant or surfactant. An example of a surfactant that may be used in the cell culture medium of the invention is methyl cellulose or a pluronic polyol, e.g., Pluronic F-68. In one embodiment, the cell culture medium comprises about 0.1-5 g/L Pluronic F-68. In one embodiment, the cell culture medium comprises about 1.0 g/L Pluronic F-68.

In still another embodiment of the invention, the cell culture medium further comprises L-glutamine.

In one embodiment, the cell culture medium has a pH range from 7.1 to 7.3.

In another embodiment, the cell culture medium of the invention has an osmolality ranging from about 320 to 450 mOsm/kg.

The invention includes a serum-free cell culture medium comprising: a basal medium; about 8-12 ml/kg or 116-126 mg/L ferric citrate; about 2-6 mg/kg recombinant human insulin; about 2-5 g/kg anhydrous glucose; about 0.1-0.5 g/kg L-glutamine; about 1-3 g/kg sodium bicarbonate; about 0.01-0.05 g/kg $NaH_2PO_4.H_2O$; about 0.4 to 0.5 g/kg of $Na_2HPO_4.7H_2O$; and about 1.0-3.0 g/kg yeast-based hydrolysate. In one embodiment, the cell culture medium comprises a basal medium; about 10.0 ml/kg or 122 mg/L ferric citrate; about 4.0 mg/kg recombinant human insulin; about 3.5 g/kg anhydrous glucose; about 0.29 g/kg L-glutamine; about 1.6 g/kg sodium bicarbonate; about 0.03 g/kg $NaH_2PO_4.H_2O$; about 0.43 to 0.44 g/kg of $Na_2HPO_4.7H_2O$; and about 2.0 g/kg yeast-based hydrolysate. In one embodiment, the cell culture medium consists essentially of a basal medium; about 10.0 ml/kg or 122 mg/L ferric citrate; about 4.0 mg/kg recombinant human insulin; about 3.5 g/kg anhydrous glucose; about 0.29 g/kg L-glutamine; about 1.6 g/kg sodium bicarbonate; about 0.03 g/kg $NaH_2PO_4.H_2O$; about 0.43 to 0.44 g/kg of $Na_2HPO_4.7H_2O$; and about 2.0 g/kg yeast-based hydrolysate.

The invention further provides a serum-free cell culture medium consisting essentially of a basal medium; about 8-12 ml/kg or 116-126 mg/L ferric citrate; about 2-6 mg/kg recombinant human insulin; about 2-5 g/kg anhydrous glucose; about 0.1-0.5 g/kg L-glutamine; about 1-3 g/kg sodium bicarbonate; about 0.01-0.05 g/kg $NaH_2PO_4.H_2O$; about 0.4 to 0.5 g/kg of $Na_2HPO_4.7H_2O$; and about 1.0-3.0 g/kg yeast-based hydrolysate. In one embodiment, the cell culture consists essentially of a basal medium; about 8-12 ml/kg or 116-126 mg/L ferric citrate; about 2-6 mg/kg recombinant human insulin; about 2-5 g/kg anhydrous glucose; about 0.1-0.5 g/kg L-glutamine; about 1-3 g/kg sodium bicarbonate; about 0.01-0.05 g/kg $NaH_2PO_4.H_2O$; about 0.4 to 0.5 g/kg of $Na_2HPO_4.7H_2O$; and about 1.0-3.0 g/kg yeast-based hydrolysate In one embodiment, the cell culture medium further comprises about 2.50 mL/kg methotrexate.

The invention also includes a method for producing a protein comprising culturing mammalian cells comprising a nucleic acid encoding the protein in the culture medium of the invention; and transferring the culture of into a cell culture production medium, such that the protein is produced.

In one embodiment, the protein is an antibody, including for example, D2E7 (adalimumab).

The invention further provides a serum-free cell culture production medium comprising: a modified basal medium which excludes the following components sodium bicarbonate, buffer, mono-basic sodium phosphate, di-basic sodium phosphate, an osmolarity regulator, a surfactant, and monosaccharide glucose; about 8 to 12 ml/kg or 122.45 mg/L ferric citrate; about 4 to 8 mL/kg or 10 to 14 mg/kg recombinant human insulin; about 5 to 9 g/kg anhydrous glucose; about 0.5 to 0.7 g/kg L-glutamine; about 1 to 2 g/kg sodium bicarbonate; about 1 to 2 g/kg HEPES; about 2 to 3 g/kg NaCl; about 0.5 to 2 g/kg Pluronic F-68; about 0.01 to 0.1 g/kg $NaH_2PO_4.H_2O$; about 0.4 to 0.5 g/kg $Na_2HPO_4.7H_2O$; about 8 to 12 g/kg yeast-based hydrolysate; and about 60 to 70 g/kg plant-based hydrolysate. In one embodiment, the cell culture production medium consists essentially of a modified basal medium which excludes the following components sodium bicarbonate, buffer, mono-basic sodium phosphate, di-basic sodium phosphate, an osmolarity regulator, a surfactant, and monosaccharide glucose; about 8 to 12 ml/kg or 122.45 mg/L ferric citrate; about 4 to 8 mL/kg or 10 to 14 mg/kg recombinant human insulin; about 5 to 9 g/kg anhydrous glucose; about 0.5 to 0.7 g/kg L-glutamine; about 1 to 2 g/kg sodium bicarbonate; about 1 to 2 g/kg HEPES; about 2 to 3 g/kg NaCl; about 0.5 to 2 g/kg Pluronic F-68; about 0.01 to 0.1 g/kg $NaH_2PO_4.H_2O$; about 0.4 to 0.5 g/kg $Na_2HPO_4.7H_2O$; about 8 to 12 g/kg yeast-based hydrolysate; and about 60 to 70 g/kg plant-based hydrolysate. In another embodiment, the cell culture production medium comprises a basal medium, about 10.0 ml/kg or 122.45 mg/L ferric citrate; about 6.0 mL/kg or 12 mg/kg recombinant human insulin; about 7.0 g/kg anhydrous glucose; about 0.58 to 0.59 g/kg L-glutamine; about 1.6 g/kg sodium bicarbonate; about 1.8 g/kg HEPES; about 2.4 to 2.5 g/kg NaCl; about 1.0 g/kg Pluronic F-68; about 0.03 to 0.04 g/kg $NaH_2PO_4.H_2O$; about 0.43 to 0.44 g/kg $Na_2HPO_4.7H_2O$; about 10.7 g/kg yeast-based hydrolysate; and about 6.9 to 7.0 g/kg plant-based hydrolysate.

The invention also provides a serum-free cell culture medium comprising a modified basal medium, which excludes the following components sodium bicarbonate, buffer, mono-basic sodium phosphate, di-basic sodium phosphate, an osmolarity regulator, a surfactant, and monosaccharide glucose; about 8 to 12 ml/kg or 122.45 mg/L ferric citrate; about 3 to 5 mL/kg or 6 to 8 mg/kg recombinant human insulin; about 5 to 9 g/kg anhydrous glucose; about 0.1 to 2 g/kg L-glutamine; about 1 to 2 g/kg sodium bicarbonate; about 1 to 2 g/kg HEPES; about 2 to 3 g/kg NaCl; about 0.1 to 2 g/kg Pluronic F-68; about 0.01 to 0.1 g/kg $NaH_2PO_4.H_2O$; about 0.4 to 0.5 g/kg $Na_2HPO_4.7H_2O$; about 0.4 to 0.5 g/kg L-asparagine monohydrate; about 2 to 6 g/kg yeast-based hydrolysate; and about 2 to 4 g/kg plant-based hydrolysate. In one embodiment, the cell culture medium consists essentially of a modified basal medium, which excludes the following components sodium bicarbonate, buffer, mono-basic sodium phosphate, di-basic sodium phosphate, an osmolarity regulator, a surfactant, and monosaccharide glucose; about 8 to 12 ml/kg or 122.45 mg/L ferric citrate; about 3 to 5 mL/kg or 6 to 8 mg/kg recombinant human insulin; about 5 to 9 g/kg anhydrous glucose; about 0.1 to 2 g/kg L-glutamine; about 1 to 2 g/kg sodium bicarbonate; about 1 to 2 g/kg HEPES; about 2 to 3 g/kg NaCl; about 0.1 to 2 g/kg Pluronic F-68; about 0.01 to 0.1 g/kg $NaH_2PO_4.H_2O$; about 0.4 to 0.5 g/kg $Na_2HPO_4.7H_2O$; about 0.4 to 0.5 g/kg L-asparagine monohydrate; about 2 to 6 g/kg yeast-based hydrolysate; and about 2 to 4 g/kg plant-based hydrolysate. In one embodiment, the cell culture medium comprises a modified basal medium; about 10.0 ml/kg or 122.45 mg/kg ferric citrate; about 3.8 to 3.9 mL/kg or 7.8 mg/kg recombinant human insulin; about 7.0 g/kg anhydrous glucose; about 0.8 to 0.9 g/kg L-glutamine; about 1.6 g/kg sodium bicarbonate; about 1.8 g/kg HEPES; about 2.6 to 2.7 g/kg NaCl; about 1.0 g/kg Pluronic F-68; about 0.03 to 0.04 g/kg $NaH_2PO_4.H_2O$; about 0.43 to 0.44 g/kg $Na_2HPO_4.7H_2O$; about 0.45 g/kg L-asparagine monohydrate; about 4.0 g/kg yeast-based hydrolysate; and about 2.6 g/kg plant-based hydrolysate.

The invention also includes a serum-free cell culture medium comprising a modified basal medium, which excludes the following components sodium bicarbonate, buffer, mono-basic sodium phosphate, di-basic sodium phosphate, an osmolarity regulator, a surfactant, and monosaccharide glucose; about 8 to 10 ml/kg or 120 to 130 mg/L ferric citrate; about 3 to 5 mL/kg or 7.8 mg/kg recombinant human insulin; about 5 to 9 g/kg anhydrous glucose; about 0.8 to 0.9 g/kg L-glutamine; about 0.3 to 0.5 g/kg L-asparagine monohydrate; about 1 of 2 g/kg sodium bicarbonate; about 1 to 2 g/kg HEPES; about 2 to 3 g/kg NaCl; about 0.5 to 2 g/kg Pluronic F-68; about 0.01 to 0.1 g/kg $NaH_2PO_4.H_2O$; about 0.1 to 1.0 g/kg $Na_2HPO_4.7H_2O$; about 2 to 6 g/kg yeast-based hydrolysate; and about 2 to 4 g/kg plant-based hydrolysate. In one embodiment, the cell culture medium consists essentially of a modified basal medium, which excludes the following components sodium bicarbonate, buffer, mono-basic sodium phosphate, di-basic sodium phosphate, an osmolarity regulator, a surfactant, and monosaccharide glucose; about 8 to 10 ml/kg or 120 to 130 mg/L ferric citrate; about 3 to 5 mL/kg or 7.8 mg/kg recombinant human insulin; about 5 to 9 g/kg anhydrous glucose; about 0.8 to 0.9 g/kg L-glutamine; about 0.3 to 0.5 g/kg L-asparagine monohydrate; about 1 of 2 g/kg sodium bicarbonate; about 1 to 2 g/kg HEPES; about 2 to 3 g/kg NaCl; about 0.5 to 2 g/kg Pluronic F-68; about 0.01 to 0.1 g/kg $NaH_2PO_4.H_2O$; about 0.1 to 1.0 g/kg $Na_2HPO_4.7H_2O$; about 2 to 6 g/kg yeast-based hydrolysate; and about 2 to 4 g/kg plant-based hydrolysate. In another embodiment, the cell culture medium comprises a modified basal medium; about 10 ml/kg or 122 mg/L ferric citrate; about 3.8 to 3.9 mL/kg or 7.8 mg/kg recombinant human insulin; about 7.0 g/kg anhydrous glucose; about 0.87 to 0.88 g/kg L-glutamine; about 0.45 g/kg L-asparagine monohydrate; about 1.6 g/kg sodium bicarbonate about 1.8 g/kg HEPES; about 2.67 to 2.68 g/kg NaCl; about 1.0 g/kg Pluronic F-68; about 0.03 to 0.04 g/kg $NaH_2PO_4.H_2O$; about 0.43 to 0.44 g/kg $Na_2HPO_4.7H_2O$; about 4.0 g/kg yeast-based hydrolysate; and about 2.6 g/kg plant-based hydrolysate.

The invention includes a serum-free cell culture medium comprising basal cell growth medium; about 8 to 12 ml/kg or 120 to 130 mg/L ferric citrate; about 2 to 6 mg/kg recombinant human insulin; about 150 to 250 g/kg anhydrous glucose; about 0.1 to 0.5 g/kg L-glutamine; about 1 to 2 g/kg sodium bicarbonate; and about 5 to 15 g/kg yeast-based hydrolysate. In one embodiment, the cell culture medium consists essentially of basal cell growth medium; about 8 to 12 ml/kg or 120 to 130 mg/L ferric citrate; about 2 to 6 mg/kg recombinant human insulin; about 150 to 250 g/kg anhydrous glucose; about 0.1 to 0.5 g/kg L-glutamine; about 1 to 2 g/kg sodium bicarbonate; and about 5 to 15 g/kg yeast-based hydrolysate. In a further embodiment, the cell culture medium comprises basal cell growth medium; about 10 ml/kg or 122.45 mg/L ferric citrate; about 4 mg/kg recombinant human insulin; about 200 g/kg anhydrous glucose; about 0.29 to 0.30 g/kg L-glutamine; about 1.6 g/kg sodium bicarbonate; and about 11 g/kg yeast-based hydrolysate. In an additional embodiment, the protein is an antibody, including, for example a fully human, anti-IL-12 antibody, e.g., ABT-874

The invention also includes a serum-free cell culture medium comprising basal cell growth medium; about 8 to 12 ml/kg or 120 to 130 mg/L ferric citrate; about 2 to 6 mg/kg recombinant human insulin; about 1 to 3 g/kg anhydrous glucose; about 0.1 to 1 g/kg L-glutamine; about 1 to 2 g/kg sodium bicarbonate; and about 1 to 4 g/kg yeast-based hydrolysate. In one embodiment, the cell culture medium consists essentially of basal cell growth medium; about 8 to 12 ml/kg or 120 to 130 mg/L ferric citrate; about 2 to 6 mg/kg recombinant human insulin; about 1 to 3 g/kg anhydrous glucose; about 0.1 to 1 g/kg L-glutamine; about 1 to 2 g/kg sodium bicarbonate; and about 1 to 4 g/kg yeast-based hydrolysate. In another embodiment, the cell culture medium comprises a basal cell growth medium; about 10 ml/kg or 122.45 mg/L ferric citrate; about 4 mg/kg recombinant human insulin; about 1.5 g/kg anhydrous glucose; about 0.29 to 0.30 g/kg L-glutamine; about 1.6 g/kg sodium bicarbonate; and about 2 g/kg yeast-based hydrolysate. In one embodiment, the pH of the cell culture medium is about 7.10 to 7.30 and the osmolality ranges from about 300 to 340 mOsm/kg. In still another embodiment, the cell culture medium comprises at least 8 g/kg yeast-based hydrolysate. In one embodiment, the protein which is produced in a mammalian cell, e.g., CHO cell, using the cell culture medium is an antibody, including, for example, an anti-IL-12 antibody or an anti-EPO-R antibody, e.g., ABT-874.

The invention further provides a cell culture medium comprising a modified basal medium which excludes the following components sodium bicarbonate, buffer, mono-basic sodium phosphate, di-basic sodium phosphate, an osmolarity regulator, a surfactant, and monosaccharide glucose; about 8 to 12 ml/kg or 120 to 130 mg/L ferric citrate; about 2.5 to 4.5 mL/kg or 7.8 mg/kg recombinant human insulin; about 5 to 9 g/kg anhydrous glucose; about 0.5 to 1 g/kg L-glutamine; about 0.1 to 1 g/kg L-asparagine monohydrate; about 1 to 2 g/kg sodium bicarbonate; about 1 to 2 g/kg HEPES; about 1 to 4 g/kg NaCl; about 0.1 to 2 g/kg Pluronic F-68; about 0.01 to 0.1 g/kg $NaH_2PO_4.H_2O$; about 0.1 to 1 g/kg $Na_2HPO_4.7H_2O$; about 2 to 6 g/kg yeast-based hydrolysate; and about 2 to 6 g/kg plant-based hydrolysate. In one embodiment, the cell culture medium of the invention consists essentially of a modified basal medium which excludes the following components sodium bicarbonate, buffer, mono-basic sodium phosphate, di-basic sodium phosphate, an osmolarity regulator, a surfactant, and monosaccharide glucose; about 8 to 12 ml/kg or 120 to 130 mg/L ferric citrate; about 2.5 to 4.5 mL/kg or 7.8 mg/kg recombinant human insulin; about 5 to 9 g/kg anhydrous glucose; about 0.5 to 1 g/kg L-glutamine; about 0.1 to 1 g/kg L-asparagine monohydrate; about 1 to 2 g/kg sodium bicarbonate; about 1 to 2 g/kg HEPES; about 1 to 4 g/kg NaCl; about 0.1 to 2 g/kg Pluronic F-68; about 0.01 to 0.1 g/kg $NaH_2PO_4.H_2O$; about 0.1 to 1 g/kg $Na_2HPO_4.7H_2O$; about 2 to 6 g/kg yeast-based hydrolysate; and about 2 to 6 g/kg plant-based hydrolysate. In another embodiment, the cell culture medium comprises a modified basal medium; about 10 ml/kg or 122.45 mg/L ferric citrate; about 3.8 to 3.9 mL/kg or 7.8 mg/kg recombinant human insulin; about 7.0 g/kg anhydrous glucose; about 0.87 to 0.88 g/kg L-glutamine; about 0.45 g/kg L-asparagine monohydrate; about 1.6 g/kg sodium bicarbonate; about 1.8 g/kg HEPES; about 2.67 g/kg NaCl; about 1.0 g/kg Pluronic F-68; about 0.03 to 0.04 g/kg $NaH_2PO_4.H_2O$; about 0.43 to 0.44 g/kg $Na_2HPO_4.7H_2O$; about 4.0 g/kg yeast-based hydrolysate; and about 2.6 g/kg plant-based hydrolysate.

The invention also includes a cell culture production medium comprising a modified basal medium, which is modified to remove the following components sodium bicarbonate, HEPES buffer, mono-basic sodium phosphate, di-basic sodium phosphate, an osmolarity regulator, a surfactant, and monosaccharide glucose; about 8 to 12 ml/kg or 120 to 130 mg/L ferric citrate; about 4 to 8 mL/kg or 10 to 14 mg/kg recombinant human insulin; about 5 to 9 g/kg anhydrous glucose; about 0.1 to 1 g/kg L-glutamine; about 1 to 2 g/kg sodium bicarbonate; about 1 to 2 g/kg HEPES; about 1 to 3 g/kg NaCl; about 0.5 to 2 g/kg Pluronic F-68; about 0.01 to 0.1 g/kg $NaH_2PO_4.H_2O$; about 0.1 to 1 g/kg $Na_2HPO_4.7H_2O$; about 8 to 12 g/kg yeast-based hydrolysate; and about 6 to 8 g/kg plant-based hydrolysate. In one embodiment, the cell culture production medium of the invention consists essentially of a modified basal medium, which is modified to remove the following components sodium bicarbonate, HEPES buffer, mono-basic sodium phosphate, di-basic sodium phosphate, an osmolarity regulator, a surfactant, and monosaccharide glucose; about 8 to 12 ml/kg or 120 to 130 mg/L ferric citrate; about 4 to 8 mL/kg or 10 to 14 mg/kg recombinant human insulin; about 5 to 9 g/kg anhydrous glucose; about 0.1 to 1 g/kg L-glutamine; about 1 to 2 g/kg sodium bicarbonate; about 1 to 2 g/kg HEPES; about 1 to 3 g/kg NaCl; about 0.5 to 2 g/kg Pluronic F-68; about 0.01 to 0.1 g/kg $NaH_2PO_4.H_2O$; about 0.1 to 1 g/kg $Na_2HPO_4.7H_2O$;

about 8 to 12 g/kg yeast-based hydrolysate; and about 6 to 8 g/kg plant-based hydrolysate. In another embodiment, the cell culture production medium comprises a modified basal medium;
about 10 ml/kg or 122.45 mg/L ferric citrate; about 6.0 mL/kg or 12 mg/kg recombinant human insulin; about 7.0 g/kg anhydrous glucose; about 0.58 to 0.59 g/kg L-glutamine; about 1.6 g/kg sodium bicarbonate about 1.8 g/kg HEPES; about 2.45 g/kg NaCl; about 1.0 g/kg Pluronic F-68; about 0.03 to 0.04 g/kg NaH$_2$PO$_4$.H$_2$O; about 0.43 to 0.44 g/kg Na$_2$HPO$_4$.7H$_2$O; about 10.7 g/kg yeast-based hydrolysate; and about 6.9 to 7.0 g/kg plant-based hydrolysate.

Another aspect of the invention is a cell culture production medium comprising a modified basal medium which excludes the following components sodium bicarbonate, buffer, mono-basic sodium phosphate, di-basic sodium phosphate, an osmolarity regulator, a surfactant, and monosaccharide glucose; about 8 to 12 ml/kg or 110 to 130 mg/L ferric citrate; about 4 to 8 mL/kg or 11 to 15 mg/kg recombinant human insulin; about 5 to 9 g/kg anhydrous glucose; about 0.1 to 1 g/kg L-glutamine; about 1 to 2 g/kg sodium bicarbonate about 1 to 2 g/kg HEPES; about 1 to 3 g/kg NaCl; about 0.1 to 2 g/kg Pluronic F-68; about 0.01 to 0.1 g/kg NaH$_2$PO$_4$.H$_2$O; about 0.1 to 1 g/kg Na$_2$HPO$_4$.7H$_2$O; about 12 to 16 g/kg yeast-based hydrolysate; and about 8 to 10 g/kg plant-based hydrolysate. In one embodiment, the cell culture production medium consists essentially of a modified basal medium which excludes the following components sodium bicarbonate, buffer, mono-basic sodium phosphate, di-basic sodium phosphate, an osmolarity regulator, a surfactant, and monosaccharide glucose; about 8 to 12 ml/kg or 110 to 130 mg/L ferric citrate; about 4 to 8 mL/kg or 11 to 15 mg/kg recombinant human insulin; about 5 to 9 g/kg anhydrous glucose; about 0.1 to 1 g/kg L-glutamine; about 1 to 2 g/kg sodium bicarbonate about 1 to 2 g/kg HEPES; about 1 to 3 g/kg NaCl; about 0.1 to 2 g/kg Pluronic F-68; about 0.01 to 0.1 g/kg NaH$_2$PO$_4$.H$_2$O; about 0.1 to 1 g/kg Na$_2$HPO$_4$.7H$_2$O; about 12 to 16 g/kg yeast-based hydrolysate; and about 8 to 10 g/kg plant-based hydrolysate. In another embodiment, the cell culture production medium of the invention comprises a modified basal medium; about 10 ml/kg or 122.45 mg/L ferric citrate; about 6.5 mL/kg or 13 mg/kg recombinant human insulin; about 7.0 g/kg anhydrous glucose; about 0.58 to 0.59 g/kg L-glutamine; about 1.6 g/kg sodium bicarbonate; about 1.8 g/kg HEPES; about 2.45 g/kg NaCl; about 1.0 g/kg Pluronic F-68; about 0.03 to 0.04 g/kg NaH$_2$PO$_4$.H$_2$O; about 0.43 to 0.44 g/kg Na$_2$HPO$_4$.7H$_2$O; about 14.2 to 14.3 g/kg yeast-based hydrolysate; and about 9.2 to 9.3 g/kg plant-based hydrolysate.

In one embodiment, the cell culture medium has a pH of about 6 to 8. In another embodiment, the cell culture medium has a pH of about 7.10 to 7.20.

In one embodiment, the cell culture medium has osmolality of about 350 to 450 mOsm/kg. In another one embodiment, the cell culture medium has osmolality of about 373 to 403 mOsm/kg.

The cell culture media of the invention may further comprise methotrexate. In one embodiment, the cell culture medium further comprises methotrexate, e.g., about 1-10 mL/kg. In another embodiment, the cell culture medium further comprises methotrexate, e.g., about 2.50 mL/kg In one embodiment, the protein which is expressed in the cell culture is an antibody, or antigen-binding fragment thereof. In one embodiment, the antibody, or antigen-binding fragment thereof, is an anti-TNFα antibody or an anti-EPO-R antibody. In another embodiment, the anti-TNFα antibody, or antigen-binding fragment thereof, is a fully human anti-TNFα antibody, including, for example, the fully human anti-TNFα antibody is D2E7 (adalimumab). In yet another embodiment, the antibody, or antigen-binding fragment thereof, is an anti-IL-12 or an anti-IL-18 antibody, including a fully human anti-IL-12 or an anti-IL-18 antibody.

The invention also includes a method of producing a protein, e.g., an antibody or antigen-binding portion thereof, comprising culturing a mammalian cell comprising a nucleic acid encoding the protein, e.g., antibody, in a cell culture medium presented herein. In one embodiment, the cell culture medium is a cell culture production medium. Examples of antibodies, or antigen binding fragments thereof, which may be produced using the methods and compositions of the invention include an anti-IL-18 antibody, an anti-TNFα antibody, an anti-IL-12 antibody, and an anti-EPO receptor (EPO-R) antibody.

In one embodiment, the invention further comprises isolating the protein from the cell culture media, e.g., cell culture production media, described herein.

In one embodiment, the cell culture media and methods of the invention are for culturing mammalian cells, including Chinese Hamster Ovary (CHO) cells.

The invention also includes a Chinese Hamster Ovary (CHO) cell in any of the cell culture media described herein.

The invention also provides an improved fed batch method and related cell culture media for producing proteins in mammalian cell culture, e.g., CHO cells. One aspect of the invention is a fed batch method of producing a protein comprising culturing mammalian cells comprising a nucleic acid encoding the protein in a cell culture comprising a cell culture production medium; and feeding the mammalian cells by adding a hydrolysate enrichment solution and a basal enrichment solution to the cell culture during a time period, wherein the hydrolysate enrichment solution comprises at least two different non-animal-based hydrolysates, such that the protein is produced.

In one embodiment, the basal enrichment solution comprises a concentrated basal medium. In another embodiment, the basal enrichment solution comprises a basal medium, asparagine, and glucose. In still another embodiment, the basal medium is PF CHO.

In one embodiment, the hydrolysate enrichment solution comprises a first hydrolysate which is not derived from a plant or an animal and a second plant-based hydrolysate. In one embodiment, the hydrolysate which is not derived from a plant or an animal and a plant-based hydrolysate is a yeast-based hydrolysate. In one embodiment, the plant-based hydrolysate is a soy-based hydrolysate In one embodiment, the protein which is produced is an antibody, or antigen binding portion thereof. Examples of antibodies, or antigen-binding portions thereof, which may be used in the fed batch methods of the invention include an anti-TNFα antibody, an anti-IL-12 antibody, an anti-IL-18 antibody, and an anti-EPO receptor (EPO-R) antibody.

The invention includes a fed batch method of producing an anti-TNFα antibody, including, for example a fully human anti-TNFα antibody such as adalimumab, comprising culturing Chinese Hamster Ovary (CHO) cells comprising a nucleic acid encoding the anti-TNFα antibody in a cell culture comprising a cell culture production medium; and feeding the CHO cells by adding a hydrolysate enrichment solution and a basal enrichment solution to the cell culture during a time period, wherein the basal enrichment solution comprises a basal medium, asparagine, and glucose, and wherein the hydrolysate enrichment solution comprises at least two different non-animal-based hydrolysates, such that the anti-TNFα antibody is produced.

The invention also features a fed batch method of producing an anti-TNFα antibody comprising culturing CHO cells comprising a nucleic acid encoding the anti-TNFα antibody in a cell culture comprising a cell culture production medium comprising a at least 1-5 g/L, e.g., 2.0 g/L of glucose, wherein the concentration of glucose is controlled by adding glucose to the cell culture production medium as required to maintain a concentration of at least 1-5 g/L, e.g., 2.0 g/L of glucose; and feeding the CHO cells by adding a hydrolysate enrichment solution and a basal enrichment solution to the cell culture during a time period, wherein the basal enrichment solution comprises a basal medium, asparagine, and glucose, and wherein the hydrolysate enrichment solution comprises at least two different non-animal-based hydrolysates, such that the anti-TNFα antibody is produced.

In one embodiment, the invention includes further recovering the anti-TNFα antibody. In yet another embodiment, the cell culture is cultured at a temperature ranging from about 32 to 38° C., e.g., 35° C.

In one embodiment, the cell culture production medium is maintained between 20 and 65% dissolved oxygen, e.g., at about 30% dissolved oxygen In one embodiment, the osmolarity of the cell culture production medium is maintained throughout the culturing to no more than 500 mOsm.

In one embodiment, the hydrolysate enrichment solution comprises a first hydrolysate which is not derived from a plant or an animal and a second plant-based hydrolysate. In yet another embodiment, the hydrolysate which is not derived from a plant or an animal and a plant-based hydrolysate is a yeast-based hydrolysate. In still another embodiment, the plant-based hydrolysate is a soy-based hydrolysate. In one embodiment, the hydrolysate enrichment solution consists essentially of about 50-280 g/kg, e.g., 250 to 280 g/kg, of a soy-based hydrolysate and about 75-300 g/kg, e.g., 150 to 180 g/kg, of a yeast-based hydrolysate. In one embodiment, the hydrolysate enrichment solution comprises about 50-280 g/kg, e.g., 250 to 280 g/kg, of a soy-based hydrolysate and about 75-300 g/kg, e.g., 150 to 180 g/kg, of a yeast-based hydrolysate.

In one embodiment, the basal medium is PF CHO.

In one embodiment, the basal enrichment solution has a pH of about 9.0 to 10.5.

In still another embodiment, the time period of the fed batch method is between about 9 to 15 days; or about 12 days.

In yet another embodiment, the basal enrichment solution is added to the cell culture production medium on at least one of the following days of the time period: Day 4, Day 6, Day 9, and Day 11. In one embodiment, the hydrolysate enrichment solution is added to the cell culture production medium on Day 4, Day 7, or Day 4 and Day 7 of the time period.

In still another embodiment, the fed batch methods further comprises adjusting the pH of the cell culture production medium according to a pH linear ramp, wherein the pH linear ramp comprises starting from a pH of about 6.5-8, e.g., 7.1 to 7.2 and resulting in a final pH of about 6.5-7.0, e.g., 6.9. In one embodiment, the pH linear ramp is adjusted over a period of at least about 24 hours. In another embodiment, the pH linear ramp is adjusted over a period of at least about 48 hours. In still another embodiment, the pH linear ramp is adjusted over a period of about 72 hours.

The invention also includes using the cell culture media described herein in the fed batch method, e.g., cell culture production medium comprising a modified basal medium which excludes the following components sodium bicarbonate, buffer, mono-basic sodium phosphate, di-basic sodium phosphate, an osmolarity regulator, a surfactant, and monosaccharide glucose; about 8 to 10 ml/kg or 110 to 130 mg/L ferric citrate; about 4 to 8 mL/kg or 10 to 14 mg/kg recombinant human insulin; about 5 to 9 g/kg anhydrous glucose; about 0.1 to 1 g/kg L-glutamine; about 1 to 3 g/kg sodium bicarbonate; about 1 to 3 g/kg HEPES; about 2 to 3 g/kg NaCl; about 0.1 to 2 g/kg Pluronic F-68; about 0.01 to 0.1 g/kg $NaH_2PO_4$—$H_2O$; about 0.1 to 0.1 g/kg $Na_2HPO_4.7H_2O$; about 8 to 12 g/kg yeast-based hydrolysate; and about 6 to 8 g/kg plant-based hydrolysate. In one embodiment, the cell cell culture production medium comprises modified basal medium; about 10.0 ml/kg or 122.45 mg/L ferric citrate; about 6.0 mL/kg or 12 mg/kg recombinant human insulin; about 7.0 g/kg anhydrous glucose; about 0.58 to 0.59 g/kg L-glutamine; about 1.6 g/kg sodium bicarbonate; about 1.8 g/kg HEPES; about 2.45 g/kg NaCl; about 1.0 g/kg Pluronic F-68; about 0.03 to 0.04 g/kg $NaH_2PO_4$—$H_2O$; about 0.43 to 0.44 g/kg $Na_2HPO_4.7H_2O$; about 10.7 g/kg yeast-based hydrolysate; and about 6.9 to 7.0 g/kg plant-based hydrolysate.

The invention also provides a fed batch method of producing an anti-IL12 antibody, such as, for example, a fully human anti-IL12 antibody (e.g., ABT-874) comprising culturing CHO cells comprising a nucleic acid encoding the antibody in a cell culture comprising a cell culture production medium, feeding the CHO cells by adding a hydrolysate enrichment solution and a basal enrichment solution to the cell culture during a time period, wherein the basal enrichment solution comprises a basal medium, asparagine, and glucose, and wherein the hydrolysate enrichment solution comprises at least two different non-animal-based hydrosylates, such that the anti-IL12 antibody is produced.

In one embodiment, the hydrolysate enrichment solution further comprises glucose.

In one embodiment, the invention also includes recovering the anti-IL12 antibody.

In one embodiment, the cell culture is cultured at a temperature ranging from about 32 to 38° C., e.g., about 33° C.

In one embodiment of the invention, the cell culture production medium is maintained at between 20-65% dissolved oxygen, e.g., at about 40% dissolved oxygen.

In yet another embodiment, the cell culture production medium has a pH of about 6.7 to 7.2.

In a further embodiment of the invention, the hydrolysate enrichment solution comprises a hydrolysate which is not derived from a plant or an animal and a plant-based hydrolysate. In one embodiment, the hydrolysate which is not derived from a plant or an animal is a yeast-based hydrolysate. In another embodiment, the plant-based hydrolysate is a soy-based hydrolysate. In still another embodiment, the hydrolysate enrichment solution consists essentially of about 50-225 g/kg, e.g., 150 to 180 g/kg, of a soy-based hydrolysate; about 75-300, e.g., 250 to 280 g/kg of a yeast-based hydrolysate; and about 1-5 g/L, e.g., 2 to 3 g/L, of glucose. In still another embodiment, the hydrolysate enrichment solution comprises about 50-225 g/kg, e.g., 150 to 180 g/kg, of a soy-based hydrolysate, about 75-300, e.g., 250 to 280 g/kg of a yeast-based hydrolysate, and about 1-5 g/L, e.g., 2 to 3 g/L, of glucose. In one embodiment, the basal enrichment solution comprises a basal medium, asparagine, and glucose.

In yet another embodiment, the basal enrichment solution has a pH of about 9-10, e.g., about 9.7, and an osmolarity of about 1400 to 1500 mOsm. In a further embodiment, the basal medium in the basal enrichment solution is PF CHO.

In one embodiment, the time period of the fed batch method is between 14-15 days.

In one embodiment, the basal enrichment solution is added to the cell culture production medium every other day beginning on day 5 of the time period.

In one embodiment of the invention, the hydrolysate enrichment solution is added to the cell culture production medium every day beginning on day 6 of the time period. In still another embodiment, the basal enrichment solution and the hydrolysate enrichment solution are added to the cell culture production medium every day beginning on day 5 of the time period.

The invention also includes using the cell culture media described herein in the fed batch method, e.g., cell culture production medium comprising a modified basal medium excluding the following components sodium bicarbonate, buffer, mono-basic sodium phosphate, di-basic sodium phosphate, an osmolarity regulator, a surfactant, and monosaccharide glucose; about 8 to 12 ml/kg or 110 to 130 mg/L ferric citrate; about 5 to 8 mL/kg or 11 to 15 mg/kg recombinant human insulin; about 5 to 9 g/kg anhydrous glucose; about 0.1 to 1 g/kg L-glutamine; about 1 to 2 g/kg sodium bicarbonate about 1 to 2 g/kg HEPES; about 2 to 3 g/kg NaCl; about 0.1 to 2 g/kg Pluronic F-68; about 0.01 to 0.1 g/kg $NaH_2PO_4$—$H_2O$; about 0.1 to 1 g/kg $Na_2HPO_4.7H_2O$; about 6 to 12 g/kg yeast-based hydrolysate; and about 6 to 8 g/kg plant-based hydrolysate. In one embodiment, the cell culture production medium comprises about 10 ml/kg or 122.45 mg/L ferric citrate; about 6.5 mL/kg or 13 mg/kg recombinant human insulin; about 7.0 g/kg anhydrous glucose; about 0.58 to 0.59 g/kg L-glutamine; about 1.6 g/kg sodium bicarbonate; about 1.8 g/kg HEPES; about 2.45 g/kg NaCl; about 1.0 g/kg Pluronic F-68; about 0.03 to 0.04 g/kg $NaH_2PO_4$—$H_2O$; about 0.43 to 0.44 g/kg $Na_2HPO_4.7H_2O$; about 10.7 g/kg yeast-based hydrolysate; and about 6.9 to 7.0 g/kg plant-based hydrolysate.

In one embodiment, the invention features methods for culturing cells on a large scale. In one embodiment, the large scale cell culture is greater than about 10 L. In another embodiment, the large scale cell culture is about 13 L.

The invention also provides combination feed solutions which are advantageous because these solutions provide a combination of nutrients in one solution. The invention includes a combination feed solution comprising glucose; a basal medium; an amino acid other than glutamine; and at least two different non-animal based hydrolysates. The invention also includes a combination feed solution consisting essentially of glucose; a basal medium; an amino acid other than glutamine; and at least two different non-animal based hydrolysates.

In one embodiment, the feed solution has a pH of about 6.0 to 8.0.

In one embodiment, the combination feed solution comprises about 100 to 250 g/kg glucose. In one embodiment, the combination feed solution comprises the amino acid asparagine, e.g., about 1.0 to 15.0 g of asparagine; or about 3.0 to 5.0 g/kg asparagine.

In one embodiment, the at least two different non-animal based hydrosylates in the combination feed solution are a plant-based hydrolysate and a hydrolysate which is not animal-based or plant based. In one embodiment, the hydrolysate which is not animal-based or plant-based is a yeast-based hydrolysate. In one embodiment, the plant-based hydrolysate is a soy-based hydrolysate.

In one embodiment, the combination feed solution comprises a basal medium that is either PF-CHO or DMEM/F12 medium. In one embodiment, the basal cell medium is a modified basal medium and excludes the following components: sodium bicarbonate, buffer, mono-basic sodium phosphate, di-basic sodium phosphate, an osmolarity regulator, a surfactant, glutamine, and glucose In still another embodiment, the combination feed solution further has a turbidity of less than about 15 NTU.

The invention features a method of maintaining a steady glucose level of a cell culture production medium comprising adding the combination feed solutions described herein.

Another aspect of the invention is a method for making a combination feed solution comprising a basal medium, glucose, and at least two different non-animal based hydrolysates comprising combining glucose and the basal cell medium into a solution; adjusting the pH of the solution of a) to about 9.5 to 10.5; adding the at least two different non-animal based hydrolysates to the solution of b); and adjusting the pH of the solution of c) such that the combination feed solution has a pH of about 6.5 to 7.5. In one embodiment, step c) comprises adding a first hydrolysate which is not animal-based or plant-based and a second plant-based hydrolysate. In one embodiment, the hydrolysate which is not animal-based or plant-based is a yeast-based hydrolysate. In still another embodiment, the plant-based hydrolysate is a soy-based hydrolysate.

The invention further provides methods for increased protein, e.g., antibody or antigen-binding portions thereof, production from mammalian cell culture. The invention provides a method for producing at least about 1.5 g/L of an antibody from a mammalian cell culture comprising culturing mammalian cells comprising a nucleic acid encoding the antibody in a cell culture production medium; and adding a combination feed solution having a pH of about 6.7 to 7.2 to the cell culture production medium, wherein the combination feed solution comprises glucose; a basal cell medium; an amino acid other than glutamine; and at least two different non-animal based hydrosylates, such that at least about 1.5 g/L of the antibody is produced. In one embodiment, at least 2 g/L of the antibody is produced. In another embodiment, at least 4 g/L of the antibody is produced. In still another embodiment, at least 5 g/L of the antibody is produced. In a further embodiment, the invention provides a method for producing about 6 g/L of an antibody.

In one embodiment, the combination feed solution comprises about 100 to 250 g/kg glucose.

The invention also provides a method for increasing titer of an antibody produced from a mammalian cell culture comprising culturing mammalian cells comprising a nucleic acid encoding the antibody in a cell culture production medium; and adding a combination feed solution having a pH of about 6.7 to 7.2 to the cell culture production medium, wherein the combination feed solution comprises glucose; a basal cell medium; an amino acid other than glutamine; and at least two different non-animal based hydrolysates, such that the titer of the antibody produced is at least 50% more than a control mammalian cell culture which is cultured according to steps a) and excluding step b). In one embodiment, the titer of the antibody produced is at least 100% more than the control. In another embodiment, the titer of the antibody produced is at least 150% more than the control.

In one embodiment, the combination feed solution is added when the cell density reaches at least $2.0 \times 10^6$ cells/mL. In one embodiment, the combination feed solution is added when the cell density reaches at least $3.5 \times 10^6$ cells/ml.

The invention further provides a method for producing a protein, e.g., an antibody or antigen-binding portion thereof, in a mammalian cell culture comprising culturing mammalian cells comprising a nucleic acid encoding the protein in a cell culture production medium; and adding a combination feed solution to the cell culture production medium using a feedback control system to monitor a metabolic indicator level in the cell culture production medium, wherein the combination feed solution is added to the cell culture production medium at a time point determined by the feedback control system, such that the antibody is produced. In one embodiment, the metabolic indicator is glucose or glutamine. In another embodiment, the feed solution is a combination feed solution comprising glucose; a basal cell medium; an amino acid other than glutamine; and at least two different non-animal based hydrolysates. In one embodiment, the antibody is an anti-TNFα antibody, an anti-IL-12 antibody, an anti-IL-18 antibody, and an anti-EPO receptor (EPO-R) antibody.

In one embodiment, a titer of at least 1.5 g/L of antibody is produced using the methods of the invention. In another embodiment, a titer of at least 2 g/L is produced. In another embodiment, a titer of at least 0.7 g/L of antibody is produced using the methods of the invention.

In one embodiment of the invention, the combination feed solution comprises about 3.0 to 12.5 g/kg asparagine.

In one embodiment of the invention, the combination feed solution comprises about 100 to 200 g/kg glucose.

In yet another embodiment, the invention further comprises monitoring a glucose level in the cell culture medium such that the glucose level is maintained between about 0.25 and 20.0 g/L. In one embodiment, the glucose level is monitored using an automated sampling device.

In one embodiment, the antibody, or antigen binding portion thereof, which is produced using the methods and compositions disclosed herein is selected from the group consisting of an anti-TNFα antibody, an anti-IL-18 antibody, an anti-EPO-R antibody, and an anti-Il-12 antibody. In one embodiment, the antibody, or antigen-binding portion thereof, is a fully human antibody. In one embodiment, the anti-TNFα antibody is D2E7 (adalimumab). In one embodiment, the anti-IL-18 antibody is ABT-325. In one embodiment, the anti-IL-12 antibody is ABT-874.

The invention also provides a method of determining a feed profile for producing a protein in a mammalian cell culture comprising culturing mammalian cells comprising a nucleic acid encoding the antibody in a cell culture production medium; and adding a combination feed solution to the cell culture production medium using a feedback control system to monitor a metabolic indicator in the cell culture production medium, wherein the combination feed solution is added to the cell culture production medium to meet a target metabolic indicator setpoint; and determining the amount of the combination feed solution added to the cell culture production medium per day, such that a feed profile is determined. In one embodiment, the metabolic indicator is glucose or glutamine.

The invention also includes a fed batch method for producing a protein in a mammalian cell culture comprising adding a combination feed solution to the mammalian cell culture according to the feed profile determined using the methods of the invention.

Another aspect of the invention is improved cell culture media which include sodium butyrate and/or N-acetylcysteine. The invention features a method of producing an antibody in a mammalian cell culture such that the titer of the antibody is at least 300 mg/L, said method comprising culturing mammalian cells comprising a nucleic acid encoding the antibody in a cell culture production medium; adding sodium butyrate, N-acetylcysteine, or a combination thereof, to the cell culture medium, wherein the sodium butyrate is added to a final concentration of about 0.1 mM to 10 mM and the N-acetylcysteine is added to a final concentration of about 1 mM to 80 mM, such that the antibody is produced at a titer of at least 300 mg/L. In one embodiment, the antibody titer is at least about 100 mg/L. In one embodiment, the antibody titer is at least about 200 mg/L. In one embodiment, the antibody titer is at least about 250 mg/L. In one embodiment, the antibody titer is at least about 300 mg/L. In one embodiment, the antibody titer is at least about 400 mg/L.

The invention also provides a method of producing an antibody in a mammalian cell culture such that the titer of the antibody is at least 10% greater than a control mammalian cell culture, said method comprising a) culturing mammalian cells comprising a nucleic acid encoding the antibody in a cell culture production medium; and b) adding sodium butyrate, N-acetylcysteine, or a combination thereof, to the cell culture medium, wherein the sodium butyrate is added to a final concentration of about 0.1 mM to 10 mM and the N-acetylcysteine is added to a final concentration of about 1 mM to 80 mM, such that the titer of the antibody is at least 10% greater than the control, wherein the control mammalian cell culture comprises step a) and excludes step b). In one embodiment, the antibody titer of the mammalian cell culture is improved at least 29% over the control mammalian cell culture. In one embodiment, the antibody titer of the mammalian cell culture is improved at least 40% over the control mammalian cell culture. In one embodiment, the antibody titer of the mammalian cell culture is improved at least 70% over the control mammalian cell culture. In one embodiment, the antibody titer of the mammalian cell culture is at least 90% greater than the control mammalian cell culture.

In one embodiment, sodium butyrate, N-acetylcysteine, or combination thereof, is added to the mammalian cell culture during the growth phase of the mammalian cell culture.

In one embodiment, the sodium butyrate, N-acetylcysteine, or combination thereof is added to the mammalian cell culture between days 4 and 7 of the culture time.

In one embodiment, the sodium butyrate, N-acetylcysteine, or combination thereof is added to the mammalian cell culture on day 0 of the culture time.

In another embodiment, the final concentration of sodium butyrate is about 0.1 mM to 10 mM. In one embodiment, the final concentration of sodium butyrate is about 0.1 mM to 8.0 mM. In one embodiment, the final concentration of sodium butyrate is about 0.1 mM to 3.0 mM of sodium butyrate.

In one embodiment, the final concentration of N-acetylcysteine is about 20 mM to 60 mM. In one embodiment, the final concentration of N-acetylcysteine is about 10 mM. In one embodiment, the final concentration of N-acetylcysteine is about 8 mM.

The invention further provides a method of extending longevity of a mammalian cell culture by at least 35% in comparison to a control mammalian cell culture, said method comprising a) culturing mammalian cells comprising a nucleic acid encoding the antibody in a cell culture production medium; and b) adding about 1 mM to 80 mM N-acetylcysteine to the cell medium; a such that the longevity of the mammalian cell culture is extended by at least 35% in comparison to a control mammalian cell culture, wherein the control mammalian cell culture comprises step a) and excludes step b).

In one embodiment, the longevity of the mammalian cell culture is extended at least about 45% in comparison to the control mammalian cell culture. In one embodiment, the longevity of the mammalian cell culture is extended at least about 55% in comparison to the control mammalian cell culture.

In one embodiment, the method of the invention features adding a final concentration of about 8 mM N-acetylcysteine to the cell culture production medium.

In one embodiment, the antibody, or antigen-binding portion thereof, is selected from the group consisting of an anti-TNFα antibody, an anti-IL-18 antibody (e.g., ABT-325), and an anti-Il-12 antibody.

The invention provides a serum-free cell culture medium comprising Part A, Part B, and Part C, wherein Part A consists essentially of a modified basal medium which excludes the following components: sodium bicarbonate, a buffer, mono-basic sodium phosphate, di-basic sodium phosphate, an osmolarity regulator, a surfactant, and monosaccharide glucose; Part B consists essentially of an inorganic iron source; and Part C comprises a recombinant growth factor; a buffer; an osmolarity regulator; an energy source; and at least two different non-animal hydrolysates. In one embodiment, Part C consists essentially of a recombinant growth factor; a buffer; an osmolarity regulator; an energy source; and at least two different non-animal hydrolysates The invention also provides a serum-free cell culture production medium comprising a modified basal medium having reduced vitamin content and excluding the following components sodium bicarbonate, buffer, mono-basic sodium phosphate, di-basic sodium phosphate, an osmolarity regulator, a surfactant, and monosaccharide glucose; about 10 ml/kg or 122.45 mg/L ferric citrate; about 6.5 mL/kg or 13 mg/kg recombinant human insulin; about 7.0 g/kg anhydrous glucose; about 0.58 to 0.59 g/kg L-glutamine; about 1.6 g/kg sodium bicarbonate about 1.8 g/kg HEPES; about 2.45 g/kg NaCl; about 1.0 g/kg Pluronic F-68; about 0.03 to 0.04 g/kg $NaH_2PO_4.H_2O$; about 0.43 to 0.44 g/kg $Na_2HPO_4.7H_2O$; about 10.7 g/kg yeast-based hydrolysate; and about 6.9 to 7.0 g/kg plant-based hydrolysate.

The invention also provides a serum-free cell culture medium comprising: a modified basal medium, having reduced vitamin content and excluding the following components sodium bicarbonate, buffer, mono-basic sodium phosphate, di-basic sodium phosphate, an osmolarity regulator, a surfactant, and monosaccharide glucose; about 150 g/kg anhydrous glucose; about 5.0 g/kg L-asparagine monohydrate; about 1.6 g/kg sodium bicarbonate; about 65 g/kg yeast-based hydrolysate; and about 41 g/kg plant-based hydrolysate.

The invention further provides a serum-free cell culture medium comprising: a modified basal medium having reduced vitamin content and excluding the following components sodium bicarbonate, buffer, mono-basic sodium phosphate, di-basic sodium phosphate, an osmolarity regulator, a surfactant, and monosaccharide glucose; about 10 ml/kg or 122.45 mg/L ferric citrate; about 6.5 mL/kg or 13 mg/kg recombinant human insulin; about 200 g/kg anhydrous glucose; about 0.58 to 0.59 g/kg L-glutamine; about 1.6 g/kg sodium bicarbonate about 1.8 g/kg HEPES; about 2.45 g/kg NaCl; about 1.0 g/kg Pluronic F-68; about 0.03 to 0.04 g/kg $NaH_2PO_4.H_2O$; about 0.43 to 0.44 g/kg $Na_2HPO_4.7H_2O$; about 10.7 g/kg yeast-based hydrolysate; and about 6.9 to 7.0 g/kg plant-based hydrolysate.

The invention also provides the following embodiments for improved media. The invention includes an improved media for culturing CHO cells to express recombinant biologics comprising parts A, B and C wherein: Part A comprises water, amino acids, vitamins and other co-factors; Part B comprises an inorganic iron source; and Part C comprises recombinant growth factors, buffers, an osmolarity regulator, an energy source, non-ferrous metal ions, hydrolysates and additional agents.

In one embodiment, part C comprises sodium bicarbonate, HEPES, mono- and di-basic sodium phosphates, sodium chloride, Pluronic F-68 and Glucose. In another embodiment, 1.5 g/L of sodium bicarbonate is added. In a further embodiment, 1.8 g/L HEPES is added. In still another embodiment, 0.1-0.5 g/L mono- and di-basic sodium phosphates is added. In yet another embodiment, 1 g/L to 6.5 g/L sodium chloride is added. In a further embodiment, 1.0 g/L Pluronic F-68 is added. In one embodiment, 1 g/L to 7 g/L glucose is added. In one embodiment, the vitamins are selected from the group consisting of PABA (p-aminobenzoic acid), Biotin, D-Ca Pantothenate (vitamin B5), Folic acid, i-Inositol, Niacinamide, Pyrodoxine (vitamin B6), Riboflavin (vitamin B2), Thiamine (vitamin B1), and Cyanocobalamin (vitamin B12). In another embodiment, the other co-factors are selected from the group consisting of lipid factors, an alcohol amine, amino acids and peptides. In still another embodiment, the lipid factors are selected from the group consisting of choline chloride and phosphatidylcholine. In yet another embodiment, the alcohol amine is ethanolamine in one embodiment, the amino acids are selected from the group consisting of asparagine, glutamine and putrescine.

In one embodiment, the peptide is glutathione. In one embodiment, 0.4 mg/L to 1.65 mg/L glutathione is added.

In still another embodiment, the inorganic iron source in Part B is ferric citrate. In one embodiment, 10 mL/L or 122 mg/L ferric citrate is added. In yet another embodiment, the ferric citrate is held to a concentration of 122 mg/L. In one embodiment, the recombinant growth factor is insulin or a recombinant analog, IGF-1 or a combination of insulin and IGF-1. In one embodiment, 4 mg/L to 13 mg/L insulin or a recombinant analog is added. In another embodiment, 25 ng/L to 150 ng/L IGF-1 is added. In yet another embodiment, 50 ng/L to 100 ng/L IGF-1 is added. In still another embodiment, 25 ng/L to 150 ng/L IGF-1 is supplemented to the insulin. In one embodiment, 50 ng/L to 100 ng/L IGF-1 is supplemented to the insulin.

In still another embodiment, the osmolarity regulator is selected from a group consisting of NaCl, KCl, $KNO_3$. In one embodiment, 0 g/L to 10 g/L osmolarity regulator is added. In another embodiment, 0 g/L to 6.5 g/L osmolarity regulator is added.

In still another embodiment, the energy source is a monosaccharide, e.g., glucose (e.g., D-glucose), maltose, mannose, galactose and fructose. In one embodiment, 1.0 to 7.0 g/L glucose is added. In another embodiment, 1.5 to 5.0 g/L glucose is added.

In yet another embodiment, the non-ferrous metal ions are added in the form of chloride and sulfate salts. In one embodiment, the non-ferrous metal ions are selected from the group consisting of potassium, magnesium, cupric, selenium, zinc, nickel, manganese, tin, cadmium, molybdate, vanadate and silicate. In one embodiment, the buffer is selected from the group consisting of carbonates, chlorides, sulphates and phosphates. In one embodiment, the buffer is selected from the group consisting of $NaHCO_3$, $CaCl_2$, $MGSO_4$, $NaH_2PO_4$, $Na_2HPO_4$, $C_3H_3O_3Na$ and N-[2-hydroxyethyl]piperazine-N'-[2-ethansul-phonic acid] known as HEPES.

In one embodiment of the invention, one of the additional agents added to the medium is methotrexate. In one embodiment, the methotrexate is used for growing CHO cells that express anti-IL-18, anti-IL12, anti-TNF-alpha (e.g., fully human anti-TNF alpha), or anti-EPO-R antibodies. In one embodiment, 100 nM to 5000 nM, is added. In one embodiment, 500 nM methotrexate is added to the medium. In one embodiment, 100 nM methotrexate is added. In one embodiment, 5000 nM methotrexate is added.

In still another embodiment of the invention, one of the additional agents is a cell protectorant, e.g., methyl cellulose or a pluronic polyol (e.g., Pluronic F-68). In one embodiment, 0.5 g/L to 1.0 g/L methyl cellulose is added. In one embodiment, 0.5 g/L to 1.0 g/L Pluronic F-68 is added. In one embodiment, 0.7 g/L to 1.2 g/L Pluronic F-68 is added.

In yet another embodiment, the pH of Part A is increased to a maximum pH of 10. In one embodiment, the pH of Part A is then reduced to a minimum of 7.0 as hydrolysates are added.

The invention also provides an improved medium for CHO cells expressing fully human anti-TNF-alpha antibody comprising: 10.0 ml/kg or 122 mg/kg ferric citrate; 2 mL/kg or 4.0 mg/kg recombinant human insulin; 3.5 g/kg anhydrous glucose; 0.292 g/k L-glutamine; 1.6 g/kg Sodium bicarbonate; 0.031 g/kg $NaH_2PO_4$—$H_2O$; 0.436 g/kg of $Na_2HPO_4.7H_2O$; 2.0 g/kg Hydrolysate; and 2.50 mL/kg Methotrexate.

The invention also provides an improved medium for CHO cells expressing fully human anti-TNF-alpha antibody comprising: 10.0 ml/kg or 122 mg/kg ferric citrate; 6.0 mL/kg or 12 mg/kg recombinant human insulin; 7.0 g/kg anhydrous glucose; 0.584 g/kg L-glutamine; 1.6 g/kg sodium bicarbonate; 1.8 g/kg HEPES; 2.45 g/kg NaCl; 1.0 g/kg Pluronic F-68; 0.031 g/kg $NaH_2PO_4$—$H_2O$; 0.436 g/kg $Na_2HPO_4.7H_2O$; 10.7 g/kg hydrolysate; 6.92 g/kg Phytone peptone; and 2.50 mL/kg Methotrexate.

Also included in the invention is an improved medium for CHO cells expressing fully human anti-TNF-alpha antibody comprising: 10 ml/kg or 122 mg/L ferric citrate; 3.88 mL/kg or 7.8 mg/kg recombinant human insulin; 7.0 g/kg anhydrous glucose; 0.876 g/kg L-glutamine; 0.45 g/kg L-asparagine monohydrate; 1.6 g/kg sodium bicarbonate; 1.8 g/kg HEPES; 2.67 g/kg NaCl; 1.0 g/k Pluronic F-68; 0.031 g/kg $NaH_2PO_4$—$H_2O$; 0.436 g/kg $Na_2HPO_4.7H_2O$; 10.7 g/kg Hydrolysate; 6.92 g/kg Phytone peptone; and 2.50 mL/kg Methotrexate.

The invention further provides an improved medium for CHO cells expressing fully human anti-TNF-alpha antibody comprising: 10 ml/kg or 122 mg/L ferric citrate; 3.88 mL/kg or 7.8 mg/kg recombinant human insulin; 7.0 g/kg anhydrous glucose; 0.876 g/kg L-glutamine; 0.45 g/kg L-asparagine monohydrate; 1.6 g/kg sodium bicarbonate; 1.8 g/kg HEPES; 2.67 g/kg NaCl; 1.0 g/k Pluronic F-68; 0.031 g/kg $NaH_2PO_4$—$H_2O$; 0.436 g/kg $Na_2HPO_4.7H_2O$; 4.0 g/kg Hydrolysate; 2.6 g/kg Phytone peptone; and 2.50 mL/kg Methotrexate.

Another aspect of the invention is an improved medium for CHO cells expressing an anti-IL-18 antibody comprising: 10 ml/kg or 122 mg/L ferric citrate; 3.88 mL/kg or 7.8 mg/kg recombinant human insulin; 7.0 g/kg anhydrous glucose; 0.876 g/kg L-glutamine; 0.45 g/kg L-asparagine monohydrate; 1.6 g/kg sodium bicarbonate; 1.8 g/kg HEPES; 2.675 g/kg NaCl; 1.0 g/k Pluronic F-68; 0.031 g/kg $NaH_2PO_4$—$H_2O$; 0.436 g/kg $Na_2HPO_4.7H_2O$; 4.0 g/kg yeast source hydrolysate; 2.579 g/kg Phytone peptone; and 2.50 mL/kg Methotrexate.

The invention provides an improved medium for CHO cells expressing an anti-IL-18 antibody comprising: 10 ml/kg or 122 mg/L ferric citrate; 6.5 mL/kg or 13 mg/kg recombinant human insulin; 7.0 g/kg anhydrous glucose; 0.584 g/kg L-glutamine; 1.6 g/kg sodium bicarbonate; 1.8 g/kg HEPES; 2.45 g/kg NaCl; 1.0 g/k Pluronic F-68; 0.031 g/kg $NaH_2PO_4$—$H_2O$; 0.436 g/kg $Na_2HPO_4.7H_2O$; 10.7 g/kg yeast hydrolysate; and 6.92 g/kg Phytone peptone.

The invention provides an improved medium for CHO cells expressing an anti-IL-18 antibody comprising: 150.0 g/kg anhydrous glucose; 5.0 g/kg L-asparagine monohydrate; 65.0 g/kg yeast hydrolysate; and 41.0 g/kg Phytone peptone.

The invention also provides an improved medium for CHO cells expressing an anti-IL-18 antibody comprising: 10 ml/kg or 122 mg/kg ferric citrate; 6.5 mL/kg or 13 mg/kg recombinant human insulin; 200.0 g/kg anhydrous glucose; 0.584 g/kg L-glutamine; 1.6 g/kg sodium bicarbonate 1.8 g/kg HEPES; 2.45 g/kg NaCl; 1.0 ml/kg Pluronic F-68; 0.031 g/kg $NaH_2PO_4$—$H_2O$; 0.436 g/kg $Na_2HPO_4.7H_2O$; 10.7 g/kg yeast hydrolysate; and 6.92 g/kg Phytone peptone.

The invention includes an improved medium for CHO cells expressing an anti-IL-18 antibody comprising: 10 ml/kg or 122 mg/kg ferric citrate; 2 mL/kg or 4 mg/kg recombinant human insulin; 3.5+1.5 g/kg anhydrous glucose; 0.292 g/kg L-glutamine; 1.6 g/kg sodium bicarbonate; 2 g/kg yeast hydrolysate; and 0.25 mL/kg methotrexate.

The invention includes an improved medium for CHO cells expressing an anti-IL-18 antibody comprising: 10 ml/kg or 122 mg/kg ferric citrate; 2 mL/kg or 4 mg/kg recombinant human insulin; 3.5+1.5 g/kg anhydrous glucose; 0.292 g/kg L-glutamine; 1.6 g/kg sodium bicarbonate; 11 g/kg yeast hydrolysate; and 0.250 mL/kg methotrexate.

The invention includes an improved medium for CHO cells expressing an anti-IL-18 antibody comprising: 10 ml/kg or 122 mg/kg ferric citrate; 2 mL/kg or 4 mg/kg recombinant human insulin; 200 g/l anhydrous glucose; 0.292 g/kg L-glutamine; 1.6 g/kg sodium bicarbonate; 8 g/kg yeast hydrolysate; and 0.250 mL/kg methotrexate.

The invention includes an improved medium for CHO cells expressing an anti-IL-18 antibody comprising: 10 ml/kg or 122 mg/kg ferric citrate; 3.88 mL/kg or 7.76 mg/L recombinant human insulin; 7.0 g/l anhydrous dextrose; 0.876 g/L L-glutamine; 1.6 g/kg sodium bicarbonate; 1.8 g/L HEPES; 2.67 g/L NaCl; 1.0 g/L Pluronic; 0.031 g/L $NaH_2PO4.H_2O$; 0.436 g/L $Na_2HPO4.7H_2O$; 4.0 g/L yeastolate; 2.579 g/L phytone peptone; 0.05 mL/kg methotrexate; 3.5 mL/L 2N NaOH; and 2.91 g/L 2N HCl; which results in a final pH of 7.10 to 7.20 and a final osmolality of 373 to 403 mOsmo/kg.

The invention includes an improved media for CHO cells expressing an anti-IL-18 antibody comprising: 10 ml/kg or 122 mg/kg ferric citrate; 13 mg/L recombinant human insulin; 7.0 g/l anhydrous dextrose; 0.584 g/L L-glutamine; 1.6 g/kg sodium bicarbonate; 1.8 g/L HEPES; 2.45 g/L NaCl; 1.0 g/L Pluronic; 0.031 g/L $NaH_2PO_4.H_2O$; 0.436 g/L $Na_2HPO_4.7H_2O$; 10.7 g/L yeastolate; 6.92 g/L phytone peptone; 0.05 mL/kg methotrexate; 5.67 mL/L 2N NaOH; and 2.5 g/L 2N HCl; which results in a final pH of 7.10 to 7.20 and a final osmolality of 373 to 403 mOsmo/kg.

The invention includes an improved medium for CHO cells expressing an anti-IL-18 antibody comprising: 10 ml/kg or 122 mg/kg ferric citrate; 4 mg/kg recombinant human insulin; 1.5 g/kg anhydrous dextrose; 0.292 g/kg L-glutamine; 1.6 g/kg sodium bicarbonate; 2.0 g/L yeastolate; and 0.25 mL/kg methotrexate; which results in a final pH of 7.10 to 7.30 and a final osmolality of 300 to 340 mOsmo/kg.

The invention includes an improved medium for CHO cells expressing an anti-IL-18 antibody comprising: 10 ml/kg or 122 mg/kg ferric citrate; 13 mg/kg recombinant human insulin; 7.0 g/kg anhydrous dextrose; 0.584 g/kg L-glutamine; 1.6 g/kg sodium bicarbonate; 1.8 g/kg HEPES; 2.45 g/kg NaCl; 1.0 g/kg Pluronic F-68; 0.031 g/kg $NaH_2PO_4.H_2O$; 0.436 g/kg $Na_2HPO_4.7H_2O$; 10.7 g/L yeastolate; and 6.92 g/kg phytone peptone; n5.67 mL/kg NaOH; and 2.5 mL/kg HCl; which results in a final pH of 7.10 to 7.20 and a final osmolality of 373 to 403 mOsmo/kg.

The invention includes an improved medium for CHO cells expressing an anti-IL-18 antibody comprising: 10 ml/kg or 122 mg/kg ferric citrate; 7.76 mg/kg recombinant human insulin; 7.0 g/l anhydrous dextrose; 0.876 g/kg L-glutamine; 1.6 g/kg sodium bicarbonate; 1.8 g/kg HEPES; 2.67 g/kg NaCl; 1.0 g/kg Pluronic F-68; 0.031 g/kg $NaH_2PO_4.H_2O$; 0.436 g/kg $Na_2HPO_4.7H_2O$; 4.0 g/L yeastolate; and 2.579 g/L phytone peptone; 0.05 mL/L methotrexate; 3.5 mL/kg NaOH; and 2.91 mL/kg HCl; which results in a final pH of 7.10 to 7.20 and a final osmolality of 373 to 403 mOsmo/kg.

The invention includes an improved medium for CHO cells expressing an anti-IL-18 antibody comprising: 10 ml/kg or 122 mg/kg ferric citrate; 13 mg/kg recombinant human insulin; 7.0 g/l anhydrous dextrose; 0.584 g/kg L-glutamine; 1.6 g/kg sodium bicarbonate; 1.8 g/kg HEPES; 2.45 g/kg NaCl; 1.0 g/kg Pluronic F-68; 0.031 g/kg $NaH_2PO_4.H_2O$; 0.436 g/kg $Na_2HPO_4.7H_2O$; 10.7 g/L yeastolate; and 6.92 g/L phytone peptone; 0.05 mL/L methotrexate; 5.67 mL/kg NaOH; and 2.5 mL/kg HCl; which results in a final pH of 7.10 to 7.20 and a final osmolality of 373 to 403 mOsmo/kg.

The invention includes an improved medium for CHO cells expressing an anti-IL-18 antibody comprising: 10 ml/kg or 122 mg/kg ferric citrate; 13 mg/kg recombinant human insulin; 7.0 g/l anhydrous dextrose; 0.584 g/kg L-glutamine; 1.6 g/kg sodium bicarbonate; 1.8 g/kg HEPES; 1.0 g/kg Pluronic F-68; 0.031 g/kg $NaH_2PO4.H_2O$; 0.436 g/kg $Na_2HPO_4.7H_2O$; 14.27 g/L yeastolate; 9.23 g/L phytone peptone; 0.05 mL/L methotrexate; 8.95 mL/kg NaOH; and 4.1 mL/kg HCl; which results in a final pH of 7.10 to 7.20 and a final osmolality of 373 to 403 mOsmo/kg.

The invention also features a method of increasing the productivity of a CHO cell line producing an IgG1 antibody by increasing the final titer comprising: adding sodium butyrate; and adding N-acetylcysteine. In one embodiment, the IgG1 antibody is anti-IL-18. In one embodiment, the increase in productivity is measure by an increase in the final titer. In one embodiment, the increase in the final titer is achieved through the addition of sodium butyrate in a concentration from 0.1 mM to 10 mM. In one embodiment, the concentration of sodium butyrate is 0.1 mM to 8.0 mM. In one embodiment, the concentration of sodium butyrate is 0.1 mM to 3.0 mM. In one embodiment, the concentration of sodium butyrate is 0.125 mM to 2.0 mM. In one embodiment, the concentration of sodium butyrate is 0.125 mM. In one embodiment, the increase in final titer is 10-80%. In one embodiment, the increase in final titer is 20-60%. In one embodiment, the increase in final titer is 35-55%. In one embodiment, the increase in final titer is 40%. In one embodiment, improved cell culture longevity is achieved through the addition of N-acetylcysteine in a concentration from 0.1 mM to 10 mM. In one embodiment, the increase in cell culture longevity is 5-50%.

The invention also provides a cell culture medium increasing the productivity of a CHO cell line producing an IgG1 antibody by increasing the final titer comprising: SR-371; and sodium butyrate. In one embodiment, the IgG1 antibody is anti-IL-18. In one embodiment, the productivity increase is measured by the final anti IL-18 titer increasing by 10-80%. In one embodiment, the productivity increase is measured by the final anti IL-18 titer increasing by 20-60%. In one embodiment, the productivity increase is measured by the final anti IL-18 titer increasing by 35-55%. In one embodiment, the productivity increase is measured by the final anti IL-18 titer increasing by 40%. In one embodiment, the concentration of sodium butyrate added is 0.125 mM to 8.0 mM. In one embodiment, the concentration of sodium butyrate added is 0.2 mM to 3.0 mM. In one embodiment, the concentration of sodium butyrate added is 0.3 mM to 2.0 mM. In one embodiment, the concentration of sodium butyrate added is 0.125 mM. In one embodiment, the concentration of N-acetylcysteine added is 1 mM to 10 mM. In one embodiment, the concentration of N-acetylcysteine added is 5 mM to 10 mM. In one embodiment, the average final titer is increased by 5-50%. In one embodiment, the average final titer is increased by 15-35%. In one embodiment, the average final titer is increased by 25-35%.

In one embodiment, the human neutralizing, antibody, or an antigen-binding portion thereof, having a high affinity for human TNFα is an isolated human antibody, or an antigen-binding portion thereof, with a light chain variable region (LCVR) having a CDR3 domain comprising the amino acid sequence of SEQ ID NO:3, or modified from SEQ ID NO:3 by a single alanine substitution at position 1, 4, 5, 7 or 8, and with a heavy chain variable region (HCVR) having a CDR3 domain comprising the amino acid sequence of SEQ ID NO:4, or modified from SEQ ID NO:4 by a single alanine substitution at position 2, 3, 4, 5, 6, 8, 9, 10 or 11. Preferably, the LCVR further has a CDR2 domain comprising the amino acid sequence of SEQ ID NO:5 (i.e., the D2E7 VL CDR2) and the HCVR further has a CDR2 domain comprising the amino acid sequence of SEQ ID NO: 6 (i.e., the D2E7 VH CDR2). Even more preferably, the LCVR further has CDR1 domain comprising the amino acid sequence of SEQ ID NO:7 (i.e., the D2E7 VL CDR1) and the HCVR has a CDR1 domain comprising the amino acid sequence of SEQ ID NO:8 (i.e., the D2E7 VH CDR1).

In another embodiment, the human neutralizing, antibody, or an antigen-binding portion thereof, having a high affinity for human TNFα is an isolated human antibody, or an antigen-binding portion thereof, with a light chain variable region (LCVR) comprising the amino acid sequence of SEQ ID NO:1 (i.e., the D2E7 VL) and a heavy chain variable region (HCVR) comprising the amino acid sequence of SEQ ID NO:2 (i.e., the D2E7 VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region.

DESCRIPTION OF FIGURE

FIG. 1 graphically depicts ABT-874 growth titer as a function of viable cell density at seed. Titer results at day 15 are strongly correlated to the viable cell density at feed. A polynomial fit to the above data suggests the optimal feed density to occur around $3.5 \cdot 10^6$ cells-ml$^-$. Process parameters were pH=6.9, T=35° C., DO=40%, inoculum ratio 1:5 or 1:4 into 4× medium, feeding begun at specified density, 1% of initial volume for 10 days.

DETAILED DESCRIPTION OF THE INVENTION

I. Definitions

While the terminology used in this application is standard within the art, definitions of certain terms are provided herein to assure clarity and definiteness to the meaning of the claims. The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Examples of antibodies which may be produced using the methods and compositions of the invention include tumor necrosis factor (TNF)— a antibodies (also referred to as anti-TNFα antibodies), interleukin (IL)-12 antibodies (also referred to as anti-IL12 antibodies), interleukin (IL)-18 antibodies (also referred to as anti-IL18 antibodies), and EPO/R antibodies (also referred to herein as anti-EPO/R antibodies). TNFα antibodies which may be produced using the invention are described in further detail in U.S. Pat. Nos. 6,090,382; 6,258,562; and 6,509,015, each of which is incorporated herein by reference in its entirety.

The invention may also be used to produce antibody fragments. The term "antigen-binding portion" or "antigen binding fragment" of an antibody (or simply "antibody portion"), as used herein, refers to one or more fragments of an antibody that retain the ability to specifically bind to an antigen (e.g., hTNFα). It has been shown that fragments of a full-length antibody can perform the antigen-binding function of an antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-546), which consists of a VH or VL domain; (vi) an isolated complementarity determining region (CDR); and (vii) a dual variable domain (DVD) antibody. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) *Proc. Natl. Acad. Sci. USA* 85:5879-5883). Such single chain antibodies are also encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444-6448; Poljak et al. (1994) *Structure* 2:1121-1123). Examples of antibody portions which may be produced by the methods of the invention are described in further detail in U.S. Pat. Nos. 6,090,382, 6,258,562, 6,509,015, each of which is incorporated herein by reference in its entirety. Production of antibody fragments or portions using the methods and compositions of the invention are also included within scope of the invention.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287) or antibodies prepared, expressed, created or isolated by any other means that involves splicing of human immunoglobulin gene sequences to other DNA sequences. Such recombinant human antibodies have variable and constant regions derived from human germ line immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germ line VH and VL sequences, may not naturally exist within the human antibody germ line repertoire in vivo.

An "isolated antibody", as used herein, is intended to refer to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as TNFα molecules from other species. Moreover, an isolated antibody may be substantially free of other cellular material and/or chemicals.

The term "basal medium" refers to any medium which is capable of supporting growth of cells. The basal medium supplies standard inorganic salts, such as zinc, iron, magnesium, calcium and potassium, as well as trace elements, vitamins, an energy source, a buffer system, and essential amino acids. Examples of basal media include, but are not limited to, Dulbecco's Modified Eagle's Medium (DMEM), DME/F12, Minimal Essential Medium (MEM), Basal Medium Eagle (BME), RPMI 1640, F-10, F-12, .α-Minimal Essential Medium (α-MEM), Glasgow's Minimal Essential Medium (G-MEM), PF CHO (SAFC Biosciences) and Iscove's Modified Dulbecco's Medium.

The term "modified basal medium," as used herein, refers to a basal medium from which at least one standard ingredient, component, or nutrient, (i.e., at least one ingredient, component, or nutrient found in a classically formulated basal medium known in the art), has been excluded, decreased, or increased. The term "modified" as used in the context of "modified basal medium" may also refer to changes in proportion between the individual components within the basal medium. In a preferred embodiment of the invention, a modified basal medium excludes at least one of the following components: sodium bicarbonate, a buffer, sodium phosphate (mono-based and/or di-basic), an osmolarity regulator, a surfactant, and glucose, e.g., monosaccharide glucose.

As used herein, the terms "cell culture medium," "culture medium," and "medium formulation" refer to a nutritive solution for the maintenance, growth, propagation, or expansion of cells in an artificial in vitro environment outside of a multicellular organism or tissue. Cell culture medium may be optimized for a specific cell culture use, including, for example, cell culture growth medium which is formulated to promote cellular growth, or cell culture production medium which is formulated to promote recombinant protein production. The terms nutrient, ingredient, and component are used interchangeably herein to refer to the constituents that make up a cell culture medium.

The terms "cell culture production medium" or "production medium" as used herein refer to cell culture medium designed to be used during the production phase of a cell culture. In a preferred embodiment, production medium is designed for recombinant protein expression during production phase. Examples of production media are provided herein, including Tables 2-7 of the Examples section.

The terms "fed batch cell culture" and "fed batch culture," as used herein, refer to a cell culture wherein the cells, preferably mammalian, and culture medium are supplied to the culturing vessel initially and additional culture nutrients are fed, continuously or in discrete increments, to the culture during culturing, with or without periodic cell and/or product harvest before termination of culture.

A "fed batch method," refers to a method by which a fed batch cell culture is supplied with additional nutrients. For example, a fed batch method may comprise adding supplemental media according to a determined feeding schedule within a given time period.

As used herein, the term "feed" refers to any addition of any substance made to a culture after inoculation. Feeding can be one or more additions.

As used herein, the terms "feed solution," "feed medium" and "feeding medium" refer to a medium containing one or more nutrients that is added to the culture beginning at some time after inoculation. In one embodiment, the feed solution is a combination feed comprising a basal medium and at least one hydrolysate, e.g., soy-based, hydrolysate, a yeast-based hydrolysate, or a combination of the two types of hydrolysates. In another embodiment of the invention, a feed solution may include only a basal medium, such as a concentrated basal medium, or may include only hydrolysates, or concentrated hydrolysates.

As used herein, the term "feedback control system" refers to a process of monitoring a given parameter, whereby an additional agent is added or an environmental modification of the cell culture is performed in order to meet a desired parameter setpoint. In one embodiment, the given parameter is the glucose level of a mammalian cell culture, whereby the glucose level is used to determine when a feed solution, e.g., a combination feed solution, should be added to the cell culture. A feedback control system may be used to maintain nutritional components needed to optimize protein production in a mammalian cell culture.

As used herein, the term "feed profile" refers to a schedule for supplementing a mammalian cell culture with a feed solution, e.g., a combination feed solution. A feed profile is preferable generated using a feedback control system.

Cells may be "genetically engineered" to express a specific polypeptide or protein when recombinant nucleic acid sequences that allow expression of the polypeptide have been introduced into the cells using methods of "genetic engineering," such as viral infection with a recombinant virus, transfection, transformation, or electroporation. See e.g. Kaufman et al. (1990), Meth. Enzymol. 185: 487-511; Current Protocols in Molecular Biology, Ausubel et al., eds. (Wiley & Sons, New York, 1988, and quarterly updates). Methods and vectors for genetically engineering cells and/or cell lines to express a protein of interest are well known to those skilled in the art. Genetic engineering techniques include but are not limited to expression vectors, targeted homologous recombination and gene activation (see, for example, U.S. Pat. No. 5,272,071 to Chappel) and trans activation by engineered transcription factors (see e.g., Segal et al., 1999, Proc. Natl. Acad. Sci. USA 96(6):2758-63). Optionally, the polypeptides are expressed under the control of a heterologous control element such as, for example, a promoter that does not in nature direct the production of that polypeptide. For example, the promoter can be a strong viral promoter (e.g., CMV, SV40) that directs the expression of a mammalian polypeptide. The host cell may or may not normally produce the polypeptide. For example, the host cell can be a CHO cell that has been genetically engineered to produce a human polypeptide, meaning that nucleic acid encoding the human polypeptide has been introduced into the CHO cell. Alternatively, the host cell can be a human cell that has been genetically engineered to produce increased levels of a human polypeptide normally present only at very low levels (e.g., by replacing the endogenous promoter with a strong viral promoter).

"Growth phase," as used herein, refers to the period during which cultured cells are rapidly dividing and increasing in number. During growth phase, cells may be generally cultured in a medium and under conditions designed to maximize cell proliferation.

The term "hydrolysate" includes any enzymatic digest, particularly a specialized type of extract prepared by treating the substance to be extracted (e.g., plant components or yeast cells) with at least one enzyme capable of breaking down the components of the substance into simpler forms (e.g., into a preparation comprising mono- or disaccharides and/or mono-, di- or tripeptides). An "hydrolysate" can be further enzymatically digested, for example by papain, and/or formed by autolysis, thermolysis and/or plasmolysis. In a preferred embodiment of the invention, the hydrolysate is not prepared from an animal source, i.e., non-animal based. Examples of preferred non-animal based hydrolysates include plant-based hydrolysates, e.g., a soy-based hydrolysate, and hydrolysates which are neither derived from plant or animal sources, e.g., a yeast-based hydrolysate.

The terms "hydrolysate enrichment solution" and "hydrolysate enrichment medium" refer to a medium containing a hydrolysate or a combination of hydrolysates, i.e., hydrolysates extracted from different sources, as a main ingredient that is added to the cell culture. The hydrolysate enrichment solution may, for example, be added to the cell culture to enhance protein production. Similarly, the terms "basal enrichment solution" and "basal enrichment medium" refer to a medium containing a basal medium (or combination of basal media) as a main ingredient. In one embodiment, a hydrolysate enrichment solution or a basal enrichment solution or a combination of the two enrichment solutions, is added to a cell culture to increase productivity of a cell culture in the production of a protein.

The production of a protein is "increased" by the addition of an additional agent or the alteration of a parameter of the protein production process, if the amount the polypeptide produced in a culture containing the additional agent or altered parameter of the protein production process, is more than the amount of the polypeptide produced in an otherwise identical culture that does not contain the additional agent or altered parameter of the protein production process. Examples of alterations to the protein production process include, but are not limited to, addition of media supplements, increases in the amount of a supplemental media, variations in the culturing temperature, and the concentration of oxygen at which the cells are cultured. An additional agent may be provided to the cell culture using a supplemental solution, such as a feed solution.

The term "ingredient" refers to any compound, whether of chemical or biological origin, that can be used in cell culture media to maintain or promote the growth of proliferation of cells. The terms "component," "nutrient" and ingredient" are used interchangeably and are all meant to refer to such compounds. Typical ingredients that are used in cell culture media include amino acids, salts, metals, sugars, lipids, nucleic acids, hormones, vitamins, fatty acids, proteins and the like.

Other ingredients that promote or maintain cultivation of cells ex vivo can be selected by those of skill in the art within the scope of the invention, and in accordance with the particular need.

As used herein, the term "inoculation" refers to the addition of cells to a medium to begin the culture.

"Production phase" refers to a period during which cells are producing maximal amounts of recombinant polypeptide or protein. A production phase is characterized by less cell division than during a growth phase, and may also include the use of medium and culture conditions designed to maximize polypeptide production.

A "recombinant polypeptide" or "recombinant protein" is a polypeptide or protein resulting from the process of genetic engineering. In a preferred embodiment, recombinant proteins are obtained from culturing cells expressing said proteins in a cell culture.

Transition phase" means a period of cell culture between a "growth phase" and a "production phase." During the transition phase, the medium and environmental conditions may be shifted from those designed to maximize proliferation to those designed to maximize polypeptide production.

The present invention provides new compositions and processes for the production of proteins, preferably recombinant protein, e.g., antibodies, by mammalian, e.g, Chinese Hamster Ovary (CHO), cell cultures. Cell culture media and processes described herein have been used for recombinant protein production, particularly recombinant (fully human, humanized, or chimeric) monoclonal antibody production. The media and processes have been modified over many antibody product lines to incorporate various improvements and advances leading to increased growth and productivity of mammalian, e.g., CHO, cells. Aspects of the improved compositions and methods of the invention are provided in detail below.

II. Proteins of Interest

Generally, the methods and compositions of the invention are useful for the production of recombinant proteins. Recombinant proteins are proteins produced by the process of genetic engineering. Particularly preferred proteins for production according to the methods and compositions of the invention, are protein-based therapeutics, also known as biologics. Preferably, the proteins are secreted as extracellular products.

Proteins that can be produced using the methods and compositions of the invention include, but are not limited to, antibodies or antigen binding fragments thereof. Numerous techniques are known in the art by which DNA encoding antibody molecules can be manipulated to yield DNAs capable of encoding recombinant proteins such as single chain antibodies, antibodies with enhanced affinity, or other antibody-based polypeptides (see, for example, Larrick et al., 1989, Biotechnology 7:934-938; Reichmann et al., 1988, Nature 332:323-327; Roberts et al., 1987, Nature 328:731-734; Verhoeyen et al., 1988, Science 239:1534-1536; Chaudhary et al., 1989, Nature 339:394-397, each of which is incorporated by reference herein). Recombinant cells producing fully human antibodies (such as are prepared using transgenic animals, and optionally further modified in vitro), as well as humanized antibodies, can also be used in the invention. The term humanized antibody also encompasses single chain antibodies. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1, each of which is incorporated by reference herein. For example, the invention can be used in the production of human and/or humanized antibodies that immunospecifically recognize specific cellular targets, e.g., any of the aforementioned proteins, the human EGF receptor, the her-2/neu antigen, the CEA antigen, Prostate Specific Membrane Antigen (PSMA), CD5, CD11a, CD18, NGF, CD20, CD45, CD52, Ep-cam, other cancer cell surface molecules, TNF-alpha, TGF-b1, VEGF, other cytokines, alpha 4 beta 7 integrin, IgEs, viral proteins (for example, cytomegalovirus). Examples of antibodies which can be produced using the compositions and methods of the invention include, but are not limited to, anti-TNFα antibody, an anti-IL-12 antibody, an anti-IL-18 antibody, and an anti-EPO receptor (EPO-R) antibody. In one embodiment, the anti-TNFα antibody is a fully human anti-TNFα antibody, e.g, adalimumab/D2E7 (see U.S. Pat. No. 6,090,382, incorporated by reference herein; Humira®; Abbott Laboratories). In one embodiment, the anti-IL-12 antibody is a fully human, anti-IL-12 antibody, e.g, ABT-874 (Abbott Laboratories; see U.S. Pat. No. 6,914,128, incorporated by reference herein). In one embodiment, the anti-IL-18 antibody is a fully human IL-18 antibody (e.g., ABT-325), e.g. see also antibodies described in US20050147610 A1. In one embodiment, the anti-EPO/R (also referred to as ABT-007) antibody is a fully human antibody, like that described in US Patent Publication No. US 20060018902 A1, hereby incorporated by reference.

Another example of the type of protein that may be produced using the methods and compositions of the invention include fusion proteins. A fusion protein is a protein, or domain or a protein (e.g. a soluble extracellular domain) fused to a heterologous protein or peptide. Examples of such fusion proteins include proteins expressed as a fusion with a portion of an immunoglobulin molecule, proteins expressed as fusion proteins with a zipper moiety, and novel polyfunctional proteins such as a fusion proteins of a cytokine and a growth factor (i.e., GM-CSF and IL-3, MGF and IL-3). WO 93/08207 and WO 96/40918 describe the preparation of various soluble oligomeric forms of a molecule referred to as CD40L, including an immunoglobulin fusion protein and a zipper fusion protein, respectively; the techniques discussed therein are applicable to other proteins. Another fusion protein is a recombinant TNFR:Fc, also known as entanercept. Entanercept (or Enbrel®; Amgen/Wyeth) is a dimer of two molecules of the extracellular portion of the p75 TNF alpha receptor, each molecule consisting of a 235 amino acid TNFR-derived polypeptide that is fused to a 232 amino acid Fc portion of human IgG1. In fact, any molecule can be expressed as a fusion protein including, but not limited to, the extracellular domain of a cellular receptor molecule, an enzyme, a hormone, a cytokine, a portion of an immunoglobulin molecule, a zipper domain, and an epitope.

III. Cell Culture Media of the Invention

The present invention provides cell culture media for use in mammalian cell culture for the production or expression of recombinant proteins, e.g., antibodies or antigen-binding portions thereof. The various cell culture media described herein may be used separately or collectively for improved cell culturing, including increased protein production and extended cell longevity.

In a preferred embodiment, the cell culture media of the invention is serum-free, meaning that the medium contains no serum (e.g., fetal bovine serum (FBS), horse serum, goat serum, or any other animal-derived serum known to one skilled in the art).

In a first aspect, the invention provides a mammalian cell culture medium which includes, in whole or in part, a modified basal medium. Modified basal cell media may be derived from standard basal cell media known in the art. Suitable basal media include, but are not limited to Dulbecco's Modified Eagle's Medium (DMEM), DME/F12, Minimal Essential Medium (MEM), Basal Medium Eagle (BME), RPMI 1640, F-10, F-12, α-Minimal Essential Medium (α-MEM), Glasgow's Minimal Essential Medium (G-MEM), PF CHO (see, e.g., CHO protein free medium (Sigma) or EX-CELL™ 325 PF CHO Serum-Free Medium for CHO Cells Protein-Free (SAFC Bioscience), and Iscove's Modified Dulbecco's Medium. Other examples of basal media which may be used in the invention include BME Basal Medium (Gibco-Invitrogen; see also Eagle, H (1965) Proc. Soc. Exp. Biol. Med. 89, 36); Dulbecco's Modified Eagle Medium (DMEM, powder) (Gibco-Invitrogen (#31600); see also Dulbecco and Freeman (1959) Virology 8, 396; Smith et al. (1960) Virology 12, 185. Tissue Culture Standards Commitee, In Vitro 6:2, 93); CMRL 1066 Medium (Gibco-Invitrogen (#11530); see also Parker R. C. et al (1957) Special Publications, N.Y. Academy of Sciences, 5, 303).

Basal medium may be modified in order to remove certain non-nutritional components found in standard basal medium, such as various inorganic and organic buffers, surfactant(s), and sodium chloride. Removing such components from basal cell medium allows an increased concentration of the remaining nutritional components, and improves overall cell growth and protein expression, as described herein. In addition, omitted components may be added back into the cell culture medium containing the modified basal cell medium according to the requirements of the cell culture conditions. As described below, it has been found that separating certain ingredients from the basal cell medium, i.e., adding modified basal cell medium as an ingredient in a cell culture medium, and subsequently adding the ingredient back into to the cell culture medium as a separate ingredient provides advantageous properties to the growth of the cell culture and protein production.

The modified basal medium of the invention excludes any, if not all, of the following ingredients: sodium bicarbonate, a buffer, mono-basic sodium phosphate, di-basic sodium phosphate, an osmolarity regulator, a surfactant, and monosaccharide glucose. These ingredients are commonly found in commercial basal cell media.

Exclusion of components, e.g., sodium bicarbonate, a buffer, mono-basic sodium phosphate, di-basic sodium phosphate, an osmolarity regulator, a surfactant, and/or monosaccharide glucose, may be done by commercial media services, e.g., SAFC Pharma™. One of skill in the art will appreciate that modified basal media may be obtained, in one embodiment, using a commercial cell culture media service, i.e., custom media service. Examples of custom media services are provided by companies such as SAFC (formerly JRH Bioscience), Invitrogen®, Atlanta Biologicals®, and Lonza.

Alternatively, one of ordinary skill in the art can prepare the modified basal cell medium of the invention according to standard methods for making basal cell media, wherein the specific ingredients described herein are omitted (see, e.g., Freshney (2005) Culture of Animal Cells: A Manual of Basic Technique; BD Bionutrients Technical Manual, (2006), Third edition; Jenkins, ed. (1999), *Animal Cell Biotechnology, Methods and Protocols*, Humana Press; Doyle and Griffiths, eds., (1997) *Essential Techniques: Mammalian Cell Culture*, John Wiley and Sons; Butler, ed. (1991) *Mammalian Cell Biotechnology: A Practical Approach* Oxford University Press; Darling and Morgan (1994) *Animal Cells: Culture and Media*, John Wiley and Sons; Freshney, ed. (1992), *Animal Cell Culture: A Practical Approach* (2nd ed), Oxford University Press; Pollard and Walker (1997), *Basic Cell Culture Protocols* (2nd Ed), Humana Press, (Part of the Methods in Molecular Biology series, Volume 75), each of which is incorporated by reference herein).

In one embodiment, the cell culture medium of the invention contains a modified basal cell medium, an iron source (preferably inorganic, e.g., ferric citrate), a recombinant growth factor; a buffer; a surfactant; an osmolarity regulator; an energy source; and at least two different non-animal hydrolysates. In addition, the modified basal cell medium may optionally contain amino acids, vitamins, or a combination of both amino acids and vitamins.

As used herein, the term "iron" means a non-animal derived source of iron used to supplement the medium. The iron source in the cell culture medium is preferably inorganic. The iron source is preferably inorganic, and includes, for example, ferric and ferrous salts such as ferric citrate or ferrous sulphate. The chelated salts such as ferric citrate and ferric ammonium citrate are preferred. However, other iron sources may be used which are not isolated from an animal source, for example, chemical iron chelators or recombinant protein iron carriers that provide equivalent amounts of iron. Iron chelate compounds which may be used include but are not limited to iron chelates of ethylenediaminetetraacetic acid (EDTA), ethylene glycol-bis(.beta.-aminoethyl ether)-N,N,N',N'-tetraacetic acid (EGTA), deferoxamine mesylate, dimercaptopropanol, diethylenetriamine-pentaacetic acid (DPTA), and trans-1,2-diaminocyclohexane-N,N,N',N'-tetraacetic acid (CDTA), as well as a ferric citrate chelate and a ferrous sulfate chelate. A particularly preferred source of iron is ferric citrate, which is preferably present in the final volume of the cell culture medium in a concentration of 0.1-1 mM. In one embodiment, the concentration of ferric citrate is about 0.5 mM. In another embodiment, the concentration of ferric citrate is 100-150 mg/L, e.g., 122 mg/L Numbers intermediate to the above recited mM, e.g., 0.1, 0.2, 0.3, 0.4, 0.5, 0.6, 0.7, 0.8, 0.9, and 1.0 mM, and mg/L, e.g., 100, 110, 120, 130, 140, and 150, are also intended to be part of this invention Non limiting examples of growth factors that may be included in the cell culture medium, are insulin, or a recombinant analog thereof, IGF-1, and a combination of insulin and IGF-1. A particularly preferred recombinant growth factor is insulin, or a recombinant analog thereof, which is preferably present in the final volume of the cell culture medium in a concentration of between about 4 mg/L to 13 mg/L. Numbers intermediate to the above recited concentration of insulin is also intended to be part of the invention, e.g., 4, 4.5, 5, 5.5, 6, 6.5, 7, 7.5, 8, 8.5, 9, 9.5, 10, 10.5, 11, 11.5, 12, 12.5, and 13.

The cell culture medium may also include a buffer. In a preferred embodiment, a buffer is excluded from the modified basal cell medium but added as a separate component to the cell culture medium (to which the modified basal cell medium is also added). Buffers for use in cell culture medium are known in the art. Nonlimiting examples of buffers which may be included the cell culture medium are phosphate buffer, HEPES, and sodium bicarbonate. In one embodiment, sodium bicarbonate is added as a buffer to the cell culture medium at a final concentration of about 0.1-3 g/L. In one embodiment, sodium bicarbonate is added as a buffer to the cell culture medium at a final concentration of about 1.6 g/L. In one embodiment, HEPES is added as a buffer to the cell culture medium at a final concentration of about 0.1-3 g/L. In another embodiment, HEPES is added as a buffer to the cell culture medium at a final concentration of 1.8 g/L. In one embodiment a phosphate buffer, e.g., mono- and di-basic sodium phosphates, is added to the cell culture medium at a final concentration of between 0.01 and 0.5 g/L. Numbers intermediate to the above recited concentrations are also intended to be part of the invention, e.g., concentration of sodium bicarbonate or HEPES 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, and 3.0 or the concentration of phosphate buffer 0.01, 0.02, 0.03, 0.04, 0.05, 0.06, 0.07, 0.08, 0.09, 0.1, 0.12, 0.14, 0.16, 0.18, 0.2, 0.22, 0.24, 0.26, 0.28, 0.3, 0.32, 0.34, 0.36, 0.38, 0.4, 0.42, 0.44, 0.46, 0.48, and 0.5 g/L.

The buffer is included to help maintain the cell culture medium at a desired pH. In one embodiment, the pH of the cell culture medium ranges from 6.0 to 8.0; 6.5 to 7.5; or 7.1 to 7.2. Numbers intermediate to these pH values, e.g., 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, and 8.0, as well as all other numbers recited herein, are also intended to be part of this invention. Ranges of values using a combination of any of the above recited values as upper and/or lower limits are intended to be included in the scope of the invention.

The cell culture medium may also include an osmolarity regulator, such as NaCl. In one embodiment, NaCl is added to the cell culture medium at a final concentration of between about 1.0 to 6.5 g/L. In one embodiment, the osmolarity of the cell culture medium ranges from 260 to 450 mOsm/kg. In one embodiment, the osmolarity of the cell culture medium ranges from 320 to 450 mOsm/kg. Numbers intermediate to the recited NaCl concentrations and mOsm/kg values. e.g, NaCl concentration of 1, 1.5, 2, 2.5, 3, 3.5, 4, 4.5, 5, 5.5, 6, and 6.5 or an mOsm/kg range of 260, 270, 280, 290, 300, 310, 320, 330, 340, 350, 360, 370, 380, 390, 400, 410, 420, 430, 440, 450, as well as numbers intermediate thereto, are also intended to be part of this invention. Ranges of values using a combination of any of the above recited values as upper and/or lower limits are intended to be included in the scope of the invention.

An energy source may also be added to the cell culture medium of the invention. Preferably, the energy source is a monosaccharide. Examples of monosaccharides which may be used in the cell culture medium include glucose (e.g., D-glucose), maltose, mannose, galactose and fructose. In one embodiment, glucose is added to the cell culture medium at a final concentration ranging from 3.5-7.0 g/L. In one embodiment, glucose is added to the cell culture medium at a final concentration of no greater than 7.0 g/L. In one embodiment, glucose is added to the cell culture medium at a final concentration of about 7.0 g/L. Numbers intermediate to the recited glucose concentrations, e.g., 3.5, 3.6, 3.7, 3.8, 3.9, 4, 4.2, 4.4, 4.6, 4.8, 5, 5.2, 5.4, 5.6, 5.8, 6, 6.2, 6.4, 6.6, 6.8, and 7, as well as numbers intermediate thereto, are also intended to be part of this invention. Ranges of values using a combination of any of the above recited values as upper and/or lower limits are also intended to be included in the scope of the invention.

An important ingredient in the cell culture medium of the invention is the addition of a hydrolysate. Cell culture medium of the invention may include a hydrolysate derived from a single source, e.g., yeast or soy, or may include a combination of hydrolysates, e.g, yeast and soy-based hydrolysates. Preferably, hydrolysates used in cell culture media of the invention are non-animal based. Examples of non-animal based hydrolysates include plant-based hydrolysates and non-plant-based hydrolysates, e.g., yeast-based hydrolysates, Tryprone, casein hydrolysate, yeast extract, or papain digested soy peptone. Hydrolysates used in the media of the invention are commercially available, including, for example, HyPep 1510®, Hy-Soy®, Hy-Yeast 412® and Hi-Yeast 444®, from sources such as Quest International, Norwich, N.Y., OrganoTechnie, S.A. France, Deutsche Hefewerke GmbH, Germany, or DMV Intl. Delhi, N.Y. Sources of yeast extracts and soy hydrolysates are also disclosed in WO 98/15614, WO 00/03000, WO 01/23527 and U.S. Pat. No. 5,741,705. Examples of a yeast-based hydrolysate which also may be used in the invention include TC Yeastolate (BD Diagnostic) and Yeastolate UF (SAFC Biosciences), while examples of plant-based hydrolysates include Soy Hydrolysate UF (SAFC Biosciences) and HyQ® Soy Hydrolysate (HyClone Media).

In one embodiment, the cell culture medium of the invention further includes glutamine, e.g, L-glutamine. Suitable sources of L-glutamine are available from various commercial sources, such as Gibco (Cat. No. 25030-081).

Optionally, the cell culture medium of the invention, including those described below in the Examples section, may include methotrexate. Examples of amounts of methotrexate used in the cell culture media for culturing CHO cells include about 100 nM to 5000 nM methotrexate. Numbers intermediate to the recited methotrexate molarity, e.g., 100, 200, 300, 400, 500, 600, 700, 800, 900, 1000, 1200, 1400, 1600, 1800, 2000, 2200, 2400, 2600, 2800, 3000, 3200, 3400, 3600, 3800, 4000, 4200, 4400, 4600, 4800, and 5000 nM, as well as numbers intermediate thereto, are also intended to be part of this invention. Ranges of values using a combination of any of the above recited values as upper and/or lower limits are also intended to be included in the scope of the invention.

In large scale bioreactors, CHO cells are particularly susceptible to sheer forces arising from the sparging of the vessel with gases and the mixing with the impeller. Thus, cell culture media of the invention may also optionally include a cell protectant. The term "cell protectant" as used herein means a substance that protects eukaryotic cells from damage. Such damage may be caused, for example, by shear forces or the effects of gas bubble sparging in a bioreactor vessel. To minimize the occurrence of cellular damage it is advantageous for the medium to contain a cell protectant, such as methyl cellulose, polyethylene glycol, polyvinyl alcohols or pluronic polyols. Of these, Pluronic® (polyol, BASF Wyandotte Corp.) polyol F68 is preferred since unlike polyvinyl alcohols this is a non-toxic substance and unlike polyethylene glycols does not interfere with downstream purification.

The cell culture medium of the invention may also include non-ferrous metal ions. Examples of non-ferrous metal ions include, but are not limited to, chloride and sulfate salts, potassium, magnesium, cupric, selenium, zinc, nickel, manganese, tin, cadmium, molybdate, vanadate, and silicate.

The cell culture medium of the invention may also include vitamins and enzyme co-factors. Examples of such vitamins and enzyme co-factors include, but are not limited to, PABA (p-Aminobenzoic Acid), Vitamin K (Biotin), Vitamin B5 (D-Calcium Pantothenate), Folic Acid, I-Inositol, Niacinamide (Niccotinic Acid Amide), Vitamin B6 (PyrdoxineHCl) (and Pyrodoxal HCl), Vitamin B2 (Riboflavin), Vitamin B1 (Thiamine), and Vitamin B12 (Cyanocobalamin). Alternatively, vitamin C (L-Ascorbic Acid) may be added to the media. Choline Chloride may also be added, it is usually considered a vitamin but it may also be considered a lipid factor.

Additionally, the cell culture medium of the invention may also include lipid like factors. Examples of lipid factors include choline chloride and phosphatidylcholine. An aid in lipid production, e.g., an alcohol amine like ethanolamine, may also be included.

In the methods and compositions of the invention, cells are preferably cultured in serum-free media. The term "serum-free" as applied to media includes any mammalian cell culture medium that does not contain serum, such as fetal bovine serum.

Also included within the scope of the invention are mammalian cells, e.g., CHO cells, in any of the improved cell culture media described herein.

In one aspect of the invention, formulations for cell culture media optimized for the production of a certain antibody are provided. Examples of optimized formulations include cell culture media for the growth or protein production of CHO cells which express an anti-TNFα antibody, an anti-IL-12 antibody, an anti-IL-18 antibody, and an anti-EPO receptor (EPO-R) antibody.

Included in the invention are cell culture media for mammalian cells, e.g., CHO cells, which express anti-TNFα antibodies, including fully human anti-TNFα antibodies. In a preferred embodiment, the fully human anti-TNFα antibody is adalimumab (also referred to as D2E7 and Humira®: Abbott Laboratories). Characteristics of adalimumab, including nucleic acid and amino acid sequences, are described in U.S. Pat. No. 6,090,382, incorporated by reference herein. Adalimumab may be produced by culturing mammalian cells, e.g., CHO cells, comprising a nucleic acid encoding the protein, e.g., adalimumab, in a cell culture growth medium, transferring the cell culture into a cell culture production medium, and isolating the protein from the cell culture production medium.

In one embodiment, the invention provides a cell culture growth medium optimized for CHO cells comprising a nucleic acid encoding adalimumab. The formulation of serum-free cell culture growth medium optimized for CHO cells expressing adalimumab includes a basal medium; ferric citrate (e.g., about 8-12 ml/kg, about 10.0 ml/kg, or 122 mg/L); recombinant human insulin (e.g., about 2-6 mg/kg, or 4.0 mg/kg); anhydrous glucose (e.g., 2-5 g/kg, about 3.5 g/kg); L-glutamine (e.g., about 0.29 g/kg); sodium bicarbonate (e.g., about 1.6 g/kg); $NaH_2PO_4 \cdot H_2O$ (e.g., about 0.03 g/kg); $Na_2HPO_4 \cdot 7H_2O$ (e.g., about 0.43 to 0.44 g/kg); and yeast-based hydrolysate (e.g., about 2.0 g/kg). Another example of a serum-free cell culture growth medium optimized for CHO cells expressing adalimumab includes the following ingredients: a modified basal medium, which excludes the following components sodium bicarbonate, buffer, mono-basic sodium phosphate, di-basic sodium phosphate, an osmolarity regulator, a surfactant, and monosaccharide glucose; ferric citrate (e.g., about 10.0 ml/kg or 122.45 mg/kg); recombinant human insulin (e.g., about 3.8 to 3.9 mL/kg or 7.8 mg/kg); anhydrous glucose (e.g., about 7.0 g/kg); L-glutamine (e.g., about 0.8 to 0.9 g/kg); sodium bicarbonate (e.g., about 1.6 g/kg); HEPES (e.g., about 1.8 g/kg); NaCl (e.g., about 2.6 to 2.7 g/kg); Pluronic F-68 (e.g., about 1.0 g/kg); $NaH_2PO_4 \cdot H_2O$ (e.g., about 0.03 to 0.04 g/kg); $Na_2HPO_4 \cdot 7H_2O$ (e.g., about 0.43 to 0.44 g/kg); L-asparagine monohydrate (e.g., about 0.45 g/kg); yeast-based hydrolysate (e.g., about 4.0 g/kg); and plant-based hydrolysate (e.g., about 2.6 g/kg). The cell culture growth medium for expressing adalimumab may further include methotrexate, e.g., about 1-5 mL/kg, or about 2.50 mL/kg.

In one embodiment, the invention provides a cell culture production medium optimized for CHO cells expressing an antibody, including, for example, a human anti-TNFα antibody (e.g., adalimumab) or an erythropoietin receptor (EPO/R) antibody. Examples of anti-EPO/R antibodies are described in US Patent Publication No. 20040071694, hereby incorporated by reference. The formulation of serum-free cell culture production medium optimized for CHO cells expressing antibodies, such as adalimumab or an anti-EPO/R antibody, includes a modified basal medium which excludes the following components sodium bicarbonate, buffer, mono-basic sodium phosphate, di-basic sodium phosphate, an osmolarity regulator, a surfactant, and monosaccharide glucose; ferric citrate (e.g., about 10.0 ml/kg or 122.45 mg/L); recombinant human insulin (e.g., about 6.0 mL/kg or 12 mg/kg); anhydrous glucose (e.g., about 7.0 g/kg); L-glutamine (e.g., about 0.58 to 0.59 g/kg); sodium bicarbonate (e.g., about 1.6 g/kg); HEPES (e.g., about 1.8 g/kg); NaCl (e.g., about 2.4 to 2.5 g/kg); Pluronic F-68 (e.g., about 1.0 g/kg); $NaH_2PO_4 \cdot H_2O$ (e.g., about 0.03 to 0.04 g/kg); $Na_2HPO_4 \cdot 7H_2O$ (e.g., about 0.43 to 0.44 g/kg); a yeast-based hydrolysate (e.g., bout 10.7 g/kg); and plant-based hydrolysate (e.g., about 6.9 to 7.0 g/kg). In one embodiment, the cell culture production medium has a pH ranging from about 7.1 to 7.2 and an osmolality ranging from 373 to 403 mOsm/kg. Numbers intermediate to the above values, e.g., recited insulin, pH, or osmolality values, are also intended to be part of this invention.

Another aspect of the invention relates to cell culture media which is optimized the production anti-interleukin-12 (IL-12) antibodies, e.g., fully human IL-12 antibodies, produced by CHO cells. In a preferred embodiment, the fully human anti-IL12 antibody is ABT-874. Characteristics of ABT-874, including the nucleic acid and amino acid sequences, are described in U.S. Pat. No. 6,914,128, incorporated by reference herein.

In one embodiment, a serum-free cell culture growth medium optimized for growth of CHO cells expressing ABT-874 includes the following: a modified basal medium, which excludes the following components sodium bicarbonate, buffer, mono-basic sodium phosphate, di-basic sodium phosphate, an osmolarity regulator, a surfactant, and monosaccharide glucose; ferric citrate (e.g., about 10 ml/kg or 122.45 mg/L); recombinant human insulin (e.g., about 3.8 to 3.9 mL/kg or 7.8 mg/kg); anhydrous glucose (e.g., about 7.0 g/kg); L-glutamine (e.g., about 0.87 to 0.88 g/kg); L-asparagine monohydrate (e.g., about 0.45 g/kg); sodium bicarbonate (e.g., about 1.6 g/kg); HEPES (e.g., about 1.8 g/kg); NaCl (e.g., about 2.67 to 2.68 g/kg); about Pluronic F-68 (e.g., 1.0 g/kg); $NaH_2PO_4 \cdot H_2O$ (e.g., about 0.03 to 0.04 g/kg); $Na_2HPO_4 \cdot 7H_2O$ (e.g., about 0.43 to 0.44 g/kg); yeast-based hydrolysate (e.g., about 4.0 g/kg); and plant-based hydrolysate (e.g., about 2.6 g/kg).

In one embodiment, a serum-free cell culture production medium for expression of ABT-874 includes the following: a modified basal medium having reduced vitamin content and excluding the following components sodium bicarbonate, buffer, mono-basic sodium phosphate, di-basic sodium phosphate, an osmolarity regulator, a surfactant, and monosaccharide glucose; ferric citrate (e.g., about 10 ml/kg or 122.45 mg/L); recombinant human insulin (e.g., about 6.5 mL/kg or 13 mg/kg); anhydrous glucose (e.g., about 7.0 g/kg); L-glutamine (e.g., about 0.58 to 0.59 g/kg); sodium bicarbonate (e.g., about 1.6 g/kg); HEPES (e.g., about 1.8 g/kg); NaCl (e.g., about 2.45 g/kg); Pluronic F-68 (e.g., about 1.0 g/kg); $NaH_2PO_4 \cdot H_2O$ (e.g., about 0.03 to 0.04 g/kg); $Na_2HPO_4 \cdot 7H_2O$ (e.g., about 0.43 to 0.44 g/kg); yeast-based hydrolysate (e.g., about 10.7 g/kg); and a plant-based hydrolysate (e.g., about 6.9 to 7.0 g/kg).

In one embodiment, the invention provides a serum free cell culture growth medium for CHO cells expressing antibodies, e.g., anti-IL12 and anti-EPO/R antibodies, comprising the following: a basal medium; ferric citrate (e.g., about 10 ml/kg or 122.45 mg/L); recombinant human insulin (e.g., about 4 mg/kg); anhydrous glucose (e.g., about 1.5 g/kg); L-glutamine (e.g., about 0.29 to 0.30 g/kg); sodium bicarbonate ((e.g., about 1.6 g/kg); and yeast-based hydrolysate (e.g., at least about 2 g/kg). In one embodiment, the cell culture growth medium for CHO cells expressing antibodies, e.g., anti-IL12 and anti-EPO/R antibodies, has a pH of about 7.10 to 7.30 and an osmolality of about 300 to 340 mOsmo/kg. The cell culture medium may also contain a yeast-based hydrolysate (e.g, at least about 8 g/kg).

Another aspect of the invention relates to cell culture media optimized for the production of anti-interleukin-18 (IL-18) antibodies, e.g., fully human IL-18 antibodies, produced by CHO cells. Examples of fully human IL-18 antibodies which may be produced using the methods and compositions of the invention are described in PCT publication WO 01/058956, incorporated by reference herein.

In one embodiment, a cell culture growth medium optimized for IL-18 antibody production in CHO cells includes the following ingredients: a modified basal medium which excludes the following components sodium bicarbonate, buffer, mono-basic sodium phosphate, di-basic sodium phosphate, an osmolarity regulator, a surfactant, and monosaccharide glucose; ferric citrate (e.g., about 10 ml/kg or 122.45 mg/L); recombinant human insulin (e.g., about 3.8 to 3.9 mL/kg or 7.8 mg/kg); anhydrous glucose (e.g., about 7.0 g/kg); L-glutamine (e.g., about 0.87 to 0.88 g/kg); L-asparagine monohydrate (e.g., about 0.45 g/kg); sodium bicarbonate (e.g., about 1.6 g/kg); HEPES (e.g., about 1.8 g/kg); NaCl (e.g., about 2.67 g/kg); Pluronic F-68 (e.g., about 1.0 g/kg); $NaH_2PO_4.H_2O$ (e.g., about 0.03 to 0.04 g/kg); $Na_2HPO_4.7H_2O$ (e.g., about 0.43 to 0.44 g/kg); yeast-based hydrolysate (e.g., about 4.0 g/kg); and a plant-based hydrolysate (e.g., about 2.6 g/kg). The cell culture medium for growth of cells expressing fully human IL-18 antibodies may have a pH of 7.10 to 7.20 and an osmolality of 373 to 403 mOsm/kg. Numbers intermediate to the above values, e.g., recited insulin, pH, or osmolality values, are also intended to be part of this invention.

An example of a cell culture production medium optimized for IL-18 antibody production in CHO cells includes the following ingredients: a modified basal medium, which is modified to remove the following components sodium bicarbonate, HEPES buffer, mono-basic sodium phosphate, di-basic sodium phosphate, an osmolarity regulator, a surfactant, and monosaccharide glucose; ferric citrate (e.g., about 10 ml/kg or 122.45 mg/L); recombinant human insulin (e.g., about 6.0 mL/kg or 12 mg/kg); anhydrous glucose (e.g., about 7.0 g/kg); L-glutamine (e.g., about 0.58 to 0.59 g/kg); sodium bicarbonate (e.g., about 1.6 g/kg); HEPES (e.g., about 1.8 g/kg); NaCl (e.g., about 2.45 g/kg); Pluronic F-68 (e.g., about 1.0 g/kg); $NaH_2PO_4.H_2O$ (e.g., about 0.03 to 0.04 g/kg); $Na_2HPO_4.7H_2O$ (e.g., about 0.43 to 0.44 g/kg); yeast-based hydrolysate (e.g., about 10.7 g/kg); and a plant-based hydrolysate (e.g., about 6.9 to 7.0 g/kg). Another example of a cell culture production medium for producing fully human anti-IL-18 antibodies includes a modified basal medium which excludes the following components sodium bicarbonate, buffer, mono-basic sodium phosphate, di-basic sodium phosphate, an osmolarity regulator, a surfactant, and monosaccharide glucose; ferric citrate (e.g., about 10 ml/kg or 122.45 mg/L); recombinant human insulin (e.g., a about 6.5 mL/kg or 13 mg/kg); anhydrous glucose (e.g., about 7.0 g/kg); L-glutamine (e.g., about 0.58 to 0.59 g/kg); sodium bicarbonate (e.g., about 1.6 g/kg); HEPES (e.g., about 1.8 g/kg); NaCl (e.g., about 2.45 g/kg); Pluronic F-68 (e.g., about 1.0 g/kg); $NaH_2PO_4.H_2O$ (e.g., about 0.03 to 0.04 g/kg); $Na_2HPO_4.7H_2O$ (e.g., about 0.43 to 0.44 g/kg); yeast-based hydrolysate (e.g., about 14.2 to 14.3 g/kg); and a plant-based hydrolysate (e.g., about 9.2 to 9.3 g/kg). The cell culture medium for CHO cells producing fully human IL-18 antibodies may have a pH of 7.10 to 7.20 and an osmolality of 373 to 403 mOsm/kg. Numbers intermediate to the above values, e.g., recited insulin, pH, or osmolality values, are also intended to be part of this invention.

Other examples of media within the scope of the invention are described below relating to fed batch methods and supplemental media which improve antibody production, in addition to the exemplary media described in the Examples section.

The media of the present invention may be used to effect appropriate culture of cells by bringing the media or its components into contact with all or part of the cell population. The media may be brought into contact with the cells by mixing, adding, combining, seeding, or stirring of one or more cells with one or more compounds, solutions, media, etc. Media may also be brought into contact with the cells all at once, incrementally, or in a step-wise manner by, for example, "feeding" to replace or supplement the medium in which cells are cultured, described in more detail below.

IV. Methods and Compositions for Improved Protein Production

The methods of compositions of the invention are directed toward mammalian cell culture. In one embodiment, the mammalian cell used is the CHO cell.

Established methods for introducing DNA into mammalian cells have been described. Kaufman, R. J., Large Scale Mammalian Cell Culture, 1990, pp. 15-69. Additional protocols using commercially available reagents, such as the cationic lipid reagents Lipofectamine™ Lipofectamine™-2000, or Lipofectamine™-plus (which can be purchased from Invitrogen), can be used to transfect cells. Feigner et al. (1987), Proc. Natl. Acad. Sci. USA 84:7413-7417. In addition, electroporation or bombardment with microprojectiles coated with nucleic acids can be used to transfect mammalian cells using procedures, such as those in Sambrook et al., Molecular Cloning: A Laboratory Manual, 2nd ed. Vol. 1-3, Cold Spring Harbor Laboratory Press (1989) and Fitzpatrick-McElligott (1992), Biotechnology (NY) 10(9): 1036-40. Selection of stable transformants can be performed using methods known in the art, such as, for example, resistance to cytotoxic drugs. Kaufman et al. ((1990), Meth. in Enzymology 185:487-511), describes several selection schemes, such as dihydrofolate reductase (DHFR) resistance. A suitable host strain for DHFR selection can be CHO strain DX-B11, which is deficient in DHFR. Urlaub and Chasin (1980), Proc. Natl. Acad. Sci. USA 77:4216-4220. A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Additional control sequences shown to improve expression of heterologous genes from mammalian expression vectors include such elements as the expression augmenting sequence element (EASE) derived from CHO cells (Morris et al., in Animal Cell Technology, pp. 529-534 (1997); U.S. Pat. Nos. 6,312,951 B1, 6,027,915, and 6,309,841 B1) and the tripartite leader (TPL) and VA gene RNAs from Adenovirus 2 (Gingeras et al. (1982), J. Biol. Chem. 257:13475-13491). The internal ribosome entry site (IRES) sequences of viral origin allows dicistronic mRNAs to be translated efficiently (Oh and Sarnow (1993), Current Opinion in Genetics and Development 3:295-300; Ramesh et al. (1996), Nucleic Acids Research 24:2697-2700). Expression of a heterologous cDNA as part of a dicistronic mRNA followed by the gene for a selectable marker (e.g. DHFR) has been shown to improve transfectability of the host and expression of the heterologous cDNA (Kaufman et al. (1990), Methods in Enzymol. 185: 487-511). Exemplary expression vectors that employ dicistronic mRNAs are pTR-DC/GFP described by Mosser et al., Biotechniques 22:150-161 (1997), and p2A5I described by Morris et al., in Animal Cell Technology, pp. 529-534 (1997).

A useful high expression vector, pCAVNOT, has been described by Mosley et al. ((1989), Cell 59:335-348). Other expression vectors for use in mammalian host cells can be constructed as disclosed by Okayama and Berg ((1983), Mol. Cell. Biol. 3:280). A useful system for stable high level expression of mammalian cDNAs in C127 murine mammary epithelial cells can be constructed substantially as described by Cosman et al. ((1986), Mol. Immunol. 23:935). A useful high expression vector, PMLSV N1/N4, described by Cosman et al. ((1984), Nature 312:768), has been deposited as ATCC 39890. Additional useful mammalian expression vectors are described in EP Patent No.-A-0 367 566 and WO 01/27299 A1. The vectors can be derived from retroviruses. In place of the native signal sequence, a heterologous signal sequence can be added, such as one of the following sequences: the signal sequence for IL-7 described in U.S. Pat. No. 4,965,195; the signal sequence for IL-2 receptor described in Cosman et al. (Nature 312:768 (1984)); the IL-4 signal peptide described in EP Patent No. 0 367 566; the typed IL-1 receptor signal peptide described in U.S. Pat. No. 4,968,607; and the type II IL-1 receptor signal peptide described in EP Patent No. 0 460 846.

The polypeptides can be produced recombinantly in eukaryotic cells, and are preferably secreted by host cells adapted to grow in cell culture. Host cells for use in the invention are preferably mammalian cells. The cells can be also genetically engineered to express a gene of interest, can be mammalian production cells adapted to grow in cell culture, and/or can be homogenous cell lines. Examples of such cells commonly used in the industry are VERO, BHK, HeLa, CV1 (including Cos), MDCK, 293, 3T3, myeloma cell lines (e.g., NSO, NS1), PC12, WI38 cells, and Chinese hamster ovary (CHO) cells, which are widely used for the production of several complex recombinant polypeptides, e.g. cytokines, clotting factors, and antibodies (Brasel et al. (1996), Blood 88:2004-2012; Kaufman et al. (1988), J. Biol Chem 263: 6352-6362; McKinnon et al. (1991), J Mol Endocrinol 6:231-239; Wood et al. (1990), J. Immunol. 145:3011-3016). The dihydrofolate reductase (DHFR)-deficient mutant cell lines (Urlaub et al. (1980), Proc Natl Acad Sci USA 77: 4216-4220, which is incorporated by reference), DXB11 and DG-44, are desirable CHO host cell lines because the efficient DHFR selectable and amplifiable gene expression system allows high level recombinant polypeptide expression in these cells (Kaufman R. J. (1990), Meth Enzymol 185:537-566, which is incorporated by reference). In addition, these cells are easy to manipulate as adherent or suspension cultures and exhibit relatively good genetic stability. CHO cells and recombinant polypeptides expressed in them have been extensively characterized and have been approved for use in clinical commercial manufacturing by regulatory agencies. The methods of the invention can also be practiced using hybridoma cell lines that produce an antibody. Methods for making hybridoma lines are well known in the art. See e.g. Berzofsky et al. in Paul, ed., Fundamental Immunology, Second Edition, pp. 315-356, at 347-350, Raven Press Ltd., New York (1989). Cell lines derived from the above-mentioned lines are also suitable for practicing the invention.

Following transformation of a suitable mammalian host cell, e.g., CHO cell, with polynucleotide sequences encoding a recombinant protein, cells demonstrating stable expression of the recombinant protein are identified and isolated. Stable expression of a recombinant protein is achieved by transfection of appropriate DNA vectors into dihydrofolate reductase deficient (DHFR-) Chinese hamster ovary cells (CHO AM-1/D, U.S. Pat. No. 6,210,924) followed by isolation and testing of individual clones demonstrating highest expression of recombinant protein, in accordance with methods known in the art. Based on growth and production in small-scale spinners and larger scale bioreactors, a specific cell line is chosen as the cell line for manufacturing of the recombinant protein.

Cells producing the highest levels of recombinant protein may be cloned by methods well-known in the art, for example, by multiple rounds of limiting dilution in 96 and/or 24 well plates under serum-free conditions, using the cell culture media of the present invention. The clones are selected based on production and growth characteristics in various suspension vessels. Enzyme Immunoassays (EIAs) may be performed to select the clone that produces the highest level of recombinant protein. Growth characteristics, including doubling times and densities may be measured by growing the clones various shaker or spinner flasks and bioreactors ranging from 100 ml to up to 3 L. An optimal clone, for example a clone with the fastest doubling time that reaches the highest density in culture, is selected, and is selected as the cell line for use in recombinant protein production. In one embodiment, the recombinant protein production is for commercial purposes and is performed using a large-scale bioreactor.

Typically, cell culture is performed under sterile, controlled temperature and atmospheric conditions in tissue culture plates (e.g., 10-cm plates, 96-well plates, etc.), or other adherent culture (e.g., on microcarrier beads) or in suspension culture such as in roller bottles. Cultures can be grown in shake flasks, small scale bioreactors, and/or large-scale bioreactors. A bioreactor is a device used to culture cells in which environmental conditions such as temperature, atmosphere, agitation, and/or pH can be monitored, adjusted and controlled. The methods, including fed batch methods, and compositions of the invention may be used in large scale mammalian cell culture, e.g., 10 L, 11 L, 12 L, 13 L, 14 L, and so forth. In one embodiment, the large scale cell culture methods and compositions of the invention are suitable for CHO cell culture and antibody production.

According to the present invention, a mammalian host cell is cultured under conditions that promote the production of the polypeptide of interest, which can be an antibody or a recombinant polypeptide. The skilled artisan may choose to use one or more of cell culture media described herein that have been developed to maximize cell growth, cell viability, and/or recombinant polypeptide production in a particular cultured host cell. Alternatively, the methods and compositions according to the current invention may be used in combination with commercially available cell culture media.

Suitable culture conditions for mammalian cells are known in the art (see e.g. Animal cell culture: A Practical Approach, D. Rickwood, ed., Oxford university press, New York (1992)), and may be combined with the improved methods of the invention. Mammalian cells may be cultured in suspension or while attached to a solid substrate. Furthermore, mammalian cells may be cultured, for example, in fluidized bed bioreactors, hollow fiber bioreactors, roller bottles, shake flasks, or stirred tank bioreactors, with or without microcarriers, and operated in a batch, fed batch, continuous, semi-continuous, or perfusion mode.

The methods according to the present invention may be used to improve the production of recombinant polypeptides in both single phase and multiple phase culture processes. In a single phase process, cells are inoculated into a culture environment and the disclosed methods are employed during the single production phase. In a multiple stage process, cells are cultured in two or more distinct phases. For example cells may be cultured first in a growth phase, under environmental conditions that maximize cell proliferation and viability, then transferred to a production phase, under conditions that maximize polypeptide production. The growth and production phases may be preceded by, or separated by, one or more transition phases. In multiple phase processes the methods according to the present invention are employed at least during the production phase.

For the purposes of understanding, yet without limitation, it will be appreciated by the skilled practitioner that cell cultures and culturing runs for protein production can include three general types; namely, continuous culture, batch culture and fed-batch culture. In a continuous culture, for example, fresh culture medium supplement (i.e., feeding medium) is provided to the cells during the culturing period, while old culture medium is removed daily and the product is harvested, for example, daily or continuously. In continuous culture, feeding medium can be added daily and can be added continuously, i.e., as a drip or infusion. For continuous culturing, the cells can remain in culture as long as is desired, so long as the cells remain alive and the environmental and culturing conditions are maintained.

In batch culture, cells are initially cultured in medium and this medium is neither removed, replaced, nor supplemented, i.e., the cells are not "fed" with new medium, during or before the end of the culturing run. The desired product is harvested at the end of the culturing run.

For fed-batch cultures, the culturing run time is increased by supplementing the culture medium one or more times daily (or continuously) with nutrient solutions during the run, i.e., the cells are "fed" with feeding medium during the culturing period. Fed-batch cultures can include the various feeding regimens and times as described below, for example, daily, every other day, every two days, etc., more than once per day, or less than once per day, and so on. Further, fed-batch cultures can be fed continuously with feeding medium. The desired product is then harvested at the end of the culturing/production run. The present invention preferably embraces fed-batch cell cultures, with feeding using optimized feeding solutions which increase protein production and can extend the protein production phase.

Improved Fed Batch Culture: Hydrolysate and Basal Enrichment Solutions

One aspect of the invention features methods and compositions for increasing protein production using an improved fed batch method in combination with supplemental basal and hydrolysate solutions. The improved fed batch method, in part, is based on the addition of two enrichment solutions, i.e., a hydrolysate enrichment solution and a basal enrichment solution, which are added to the cell culture medium during a time period during protein production. The hydrolysate enrichment solution used in the fed batch method of the invention comprises a first hydrolysate which is not derived from a plant or an animal and a second plant-based hydrolysate. An example of a hydrolysate which is not derived from a plant or an animal and a plant-based hydrolysate is a yeast-based hydrolysate. An example of a plant-based hydrolysate which may be used in the hydrolysate enrichment solution is a soy-based hydrolysate. The basal enrichment solution includes a basal medium, e.g., PF CHO, asparagine, and glucose, and the hydrolysate enrichment solution includes at least two different non-animal-based hydrolysates. The hydrolysate and basal enrichment solutions are added to the cell culture at intervals during a time period, e.g., daily intervals during an 11-15 day time period, and may be added on the same day or on different days.

The invention features a fed batch method for producing an anti-TNFα antibody, e.g., adalimumab/D2E7, comprising culturing Chinese Hamster Ovary (CHO) cells comprising a nucleic acid encoding the anti-TNFα antibody in a cell culture at a culturing temperature of ranging from 32 to 38° C. In one embodiment, the culturing temperature is 35° C. The CHO cells are fed a hydrolysate enrichment solution and a basal enrichment solution in order to address, e.g., solve or correct, nutritional deficiencies to maximize productivity. The hydrolysate and basal enrichment solutions are added to the cell culture. In one embodiment, the cell culture production medium comprising between 20 and 65% dissolved oxygen, e.g., about 30% dissolved oxygen. In one embodiment, the cell culture production medium contain a level of glucose needed for protein production, e.g., at least 1-5 g/L of glucose. In one embodiment, the cell culture production medium contains about 1.5-2.5 g/L of glucose. In a further embodiment, the cell culture production medium contains about 2.0 g/L of glucose. The glucose concentration may be controlled throughout the protein production culturing process by adding glucose to the cell culture production medium as required to maintain a given concentration, e.g., at least 2.0 g/L of glucose. In one embodiment, the hydrolysate enrichment solution used in the fed batch method for an anti-TNFα antibody comprises of about 50-280 g/L of a soy-based hydrolysate (including ranges and numbers therein, e.g., 100-225, 50-225, 255-275, and 265 g/L), and about 75-300 g/L of a yeast-based hydrolysate (including ranges and numbers therein, e.g., 100-250, 150-200, 145-175, and 165 g/L).

Basal enrichment solution optimized for use in a fed batch method for the production of an anti-TNFα antibody, e.g., adalimumab/D2E7, in CHO cells has a pH of about 9.0 to 10.5 (including ranges and numbers therein, e.g., 9.1, 9.2, 9.3, 9.4, 9.5, 9.6, 9.7, 9.8, 9.9, 10, 10.1, 10.2, 10.3, 10.4, 10.5). The time period during which the hydrolysate enrichment solution and the basal enrichment solution are added is between 9 to 15 days, e.g., 12 days. In one embodiment, the basal enrichment solution is added to the cell culture medium on at least one of the following days of the time period: Day 4, Day 6, Day 9, and Day 11, and the hydrolysate enrichment solution is added to the cell culture medium on Day 4, Day 7, or Day 4 and Day 7 of the time period. Numbers intermediate to the above values are also intended to be part of this invention.

In another alternative, the fed batch method for the production of an anti-TNFα antibody, e.g., adalimumab/D2E7, may include adjusting the pH of the cell culture medium according to a pH linear ramp comprising starting from a pH of about 6.5-8, e.g., 7.1 to 7.2, and resulting in a final pH of about 6.9. In one embodiment, the pH linear ramp is adjusted over a period of at least about 24 hours, 48 hours, or 72 hours.

The invention also features a fed batch method of producing an anti-IL12 antibody, e.g., ABT-874, comprising culturing Chinese Hamster Ovary (CHO) cells comprising a nucleic acid encoding the anti-IL12 antibody in a cell culture at a culturing temperature of ranging from 32 to 38° C., e.g., 33° C. The hydrosylate enrichment solution used for IL-12 antibody production may also contain glucose. In one embodiment, the CHO cells are cultured at a pH of about 6.9. The CHO cells are fed a hydrolysate enrichment solution and a basal enrichment solution in order to maintain nutritional deficiencies to maximize productivity. The hydrolysate and basal enrichment solutions are added to the cell culture. In one embodiment, the cell culture production medium comprising between 20 and 65% dissolved oxygen, e.g., about 40% dissolved oxygen. In one embodiment, the hydrolysate enrichment solution used in the fed batch method for an anti-IL12 antibody comprises about 50-280 g/L of a soy-based hydrolysate (including ranges and numbers therein, e.g., 100-225, 50-225, 255-275, and 265 g/L), about 75-300 g/L of a yeast-based hydrolysate (including ranges and numbers therein, e.g., 100-250, 150-200, 145-175, and 165 g/L), and about 2-3 g/L of glucose, e.g., 2.4 g/L glucose. Basal enrichment solution optimized for use in a fed batch method for the expression of an anti-IL12 antibody, e.g., ABT-874, in CHO cells has a pH of about 9.7 and an osmolarity of about 1480 mOsm. The time period during which the hydrolysate enrichment solution and the basal enrichment solution are added is between 14 to 15 days, e.g., 12 days. In one embodiment, the basal enrichment solution is added to the cell culture production medium every other day beginning on day 5 of the time period, and the hydrolysate enrichment solution is added to the cell culture production medium every day beginning on day 6 of the time period. Alternatively, the basal enrichment solution and the hydrolysate enrichment solution may be added to the cell culture production medium every day beginning on day 5 of the time period. Numbers intermediate to the above range values are also intended to be part of this invention.

Stable, High Concentration Feed Solution

One aspect of the invention features methods and compositions relating to an improved, stable high concentration feed solution for improving protein productivity. The improved feed solution may be used to supplement cell culture production medium in the production of an antibody. The feed solution includes glucose (e.g., 100 to 250 g/kg); a basal medium; an amino acid other than glutamine, e.g., asparagine (e.g., 1.0 to 15.0 g/kg; 3-12.5 g/kg, or 3-5 g/kg); and at least two different non-animal based hydroslyates. In addition, the feed solution has a pH of about 6.0 to 7.5. The two different non-animal based hydrolysates may include a plant-based hydrolysate, e.g. soy-based hydrolysate, and a hydrolysate which is not animal-based or plant based, e.g., a yeast-based hydrolysate. Any basal medium known in the art may be used in the improved feed solution, including, but not limited to, PF CHO or DMEM/F12 medium. A modified basal medium may also be used. In one embodiment, the basal cell medium excludes the following components: sodium bicarbonate, buffer, mono-basic sodium phosphate, di-basic sodium phosphate, an osmolarity regulator, a surfactant, glutamine, and glucose. The improved feed solution is stable, having a turbidity of less than about 15 NTU. The invention also includes maintaining a steady glucose level of a cell culture production medium by adding the feed solution. Numbers intermediate to the above range values are also intended to be part of this invention, e.g., 3.0, 3.1, 3.2, 3.3, 3.6, 3.8, 4, 4.2, 4.4, 4.6, 4.8, and 5 g/kg asparagine.

Also included in the invention is a method for making a feed solution comprising glucose and at least two different non-animal based hydrolysates. The method for making the feed solution includes combining glucose and a basal cell medium into a combination solution, and adjusting the pH of the combination solution to about 9.5 to 10.5. At least two different non-animal based hydrolysates are then added to the solution, and the pH is adjusted again such that the resulting feed solution has a pH of about 6.5 to 7.5. Numbers intermediate to the above range values are also intended to be part of this invention, e.g., pH of 6.6, 6.7, 6.8, 6.9, 7.0, 7.1, 7.2, 7.3, 7.4, 7.5.

The feed solution of the invention may be used to achieve high levels of recombinant protein production, e.g., antibody production, from mammalian cell culture. In one embodiment, the invention features a method for producing at least 1.5 g/L of an antibody from a mammalian cell culture comprising culturing mammalian cells comprising a nucleic acid encoding the antibody in a cell culture production medium. A feed solution having a pH of about 6.7 to 7.0 is then added to the cell culture production medium. The feed solution includes glucose (e.g., about 100 to 250 g/kg); a basal cell medium; an amino acid other than glutamine; and at least two different non-animal based hydrolysates. In one embodiment, such a process results in at least 2 g/L of an antibody being produced; at least 4 g/L of an antibody being produced; at least about 5 g/L of the antibody; and at least 6 g/L of the antibody. Numbers intermediate to the above range values are also intended to be part of this invention, e.g., 1.5, 1.6, 1.7, 1.8, 1.9, 2.0, 2.1, 2.2, 2.3, 2.4, 2.5 g/L of antibody.

By using a feed solution having a pH of about 6.7 to 7.2 and including the following components: glucose; a basal cell medium; about an amino acid other than glutamine; and at least two different non-animal based hydrolysates, the titer of antibody produced from a mammalian cell culture can be increased. In one embodiment, adding the feed solution to a cell culture production medium for mammalian cells comprising a nucleic acid encoding the antibody, results in an increase of at least 50% more than a control mammalian cell culture which is cultured without addition of the feed solution. In one embodiment, addition of the feed solution results in a titer increase of at least 100% more than the control. In one embodiment, addition of the feed solution results in a titer increase of at least 150% more than the control. The supplemental feed solution may be added to the cell culture at a certain cell density, such as when the cell density reaches at least $2.0 \times 10^6$ cells/mL or when the cell density reaches at least $3.5 \times 10^6$ cells/ml. Numbers intermediate to the above range values are also intended to be part of this invention. Ranges of values using a combination of any of the above recited values as upper and/or lower limits are intended to be included in the scope of the invention.

As the fed batch methods of the invention serve to address, e.g., solve or correct, certain nutritional requirements of a cell culture for the production of a protein, e.g., an antibody, it may be advantageous to monitor certain ingredients. Ingredients that may be monitored include any metabolic indicator, i.e., an indicator of cell metabolism. In one embodiment, the fed batch method of the invention comprises monitoring the glucose level in the cell culture medium, including, monitoring the glucose level so that it is maintained at between 0.25-20 g/L. In one embodiment, the glucose level is maintained at 0.5 to 5.5 g/L or 4.0-5.5 g/L. By monitoring glucose levels, cell metabolism can be indirectly monitored. As described in Example 3 below, glucose may be used as a metabolic indicator. In one embodiment, a cell culture may be supplemented with a nutritional component(s), e.g., hydrolysate, based on the level of glucose. Methods for monitoring glucose levels are known in the art and may include monitoring using an automated sampling device. Another example of a metabolic indicator that may be used is glutamine. Numbers intermediate to the above ranges, as well as all other numbers recited herein, are also intended to be part of this invention. Ranges of values using a combination of any of the above recited values as upper and/or lower limits are intended to be included in the scope of the invention.

A feedback control system may be used to monitor a metabolic indicator level in the cell culture production medium. In one embodiment, in order to meet a desired parameter setpoint, e.g., a pre-determined glucose level, a combination feed solution is added to the cell culture production medium as determined by the feedback control system.

The feedback control system may also be used to determine a feed profile for a given mammalian cell culture and the production of a protein of interest. In one embodiment, a method of determining a feed profile for producing a protein in a mammalian cell culture comprises culturing mammalian cells comprising a nucleic acid encoding the protein and adding a feed solution, e.g., a combination feed solution, to the cell culture medium using a feedback control system to monitor a metabolic indicator. The feed solution is added to the cell culture production medium to meet a target metabolic indicator setpoint, e.g., a glucose level. Following the conclusion of the cell culture, the amount of the feed solution added to the cell culture production medium per day is determined and provides a feed profile of when a feed solution should be added to the cell culture. Once a feed profile is established, monitoring of the metabolic indicator is no longer needed for a given mammalian cell culture producing a protein of interest. A feed profile presents many advantages, including a decreased risk of contamination since frequent sampling is no longer required.

N-Acetylcysteine and Sodium Butyrate Methods and Compositions

As described above, the cell culture processes of this invention advantageously achieve an increased antibody titer. Another aspect of the invention for achieving protein productivity in mammalian cell culture is through the addition of sodium butyrate, N-acetylcysteine, or a combination thereof, to the cell culture medium. In one embodiment, the invention features a method of producing an antibody by adding sodium butyrate (e.g., 0.1 mM to 10 mM), N-acetylcysteine (e.g., 1 mM to 80 mM), or a combination thereof, to the cell culture medium. In one embodiment, the antibody titer is at least about 100 mg/L; at least about 150 mg/L; at least about 200 mg/L; at least about 250 mg/L; at least about 300 mg/L; at least about 350 mg/L; or at least about 400 mg/L.

The invention also features a method of producing an antibody in a mammalian cell culture such that the titer of the antibody is improved at least 10% over a control mammalian cell culture by adding sodium butyrate (e.g., final concentration of 0.1 mM to 10 mM), N-acetylcysteine (e.g., final concentration of 1 mM to 80 mM), or a combination thereof, to cell culture medium (control accordingly lacks sodium butyrate, N-acetylcysteine, or the combination thereof). In one embodiment, the antibody titer of the mammalian cell culture is improved at least 29% over the control mammalian cell culture; at least 40% over the control mammalian cell culture; at least 70% over the control mammalian cell culture; or at least 90% greater than the control mammalian cell culture. The sodium butyrate, N-acetylcysteine, or the combination thereof may be added to the mammalian cell culture during the growth phase of the mammalian cell culture. In one embodiment, the sodium butyrate, N-acetylcysteine, or the combination thereof, is added to the mammalian cell culture between days 4 and 7 of the culture time. In one embodiment, N-acetylcysteine is added, either alone or in combination with sodium butyrate, in an amount ranging from a final concentration of 5 mM to 80 mM, e.g., 20-60 mM, or about 10 mM.

The invention also features a method for extending longevity of a mammalian cell culture by at least about 45% in comparison to a control mammalian cell culture by adding about 0.1 mM to 10 mM of N-acetylcysteine to the cell medium (control lacks this addition). In one embodiment, the longevity of the mammalian cell culture is extended at least about 35% in comparison to the control mammalian cell culture; or at least about 55% in comparison to the control mammalian cell culture.

It should be noted that cell culture media and improved culturing methods described herein may be used separately or in combination with one another.

After culturing using the methods and compositions of the invention, the resulting expressed protein can then be recovered or collected. In addition the protein can purified, or partially purified, from such culture or component (e.g., from culture medium or cell extracts or bodily fluid) using known processes. Fractionation procedures can include but are not limited to one or more steps of filtration, centrifugation, precipitation, phase separation, affinity purification, gel filtration, ion exchange chromatography, hydrophobic interaction chromatography (HIC; using such resins as phenyl ether, butyl ether, or propyl ether), HPLC, or some combination of above.

For example, the purification of the polypeptide can include an affinity column containing agents which will bind to the polypeptide; one or more column steps over such affinity resins as concanavalin A-agarose, HEPARIN-TOYOPEARL (chromatography medium) or Cibacrom blue 3GA SEPHAROSE (agarose beads); one or more steps involving elution; and/or immunoaffinity chromatography. The polypeptide can be expressed in a form that facilitates purification. For example, it may be expressed as a fusion polypeptide, such as those of maltose binding polypeptide (MBP), glutathione-S-transferase (GST) or thioredoxin (TRX). Kits for expression and purification of such fusion polypeptides are commercially available from New England BioLab (Beverly, Mass.), Pharmacia (Piscataway, N.J.) and InVitrogen, respectively. The polypeptide can be tagged with an epitope and subsequently purified by using a specific antibody directed to such epitope. One such epitope FLAG (epitope tag) is commercially available from Kodak (New Haven, Conn.). It is also possible to utilize an affinity column comprising a polypeptide-binding polypeptide, such as a monoclonal antibody to the recombinant protein, to affinity-purify expressed polypeptides. Other types of affinity purification steps can be a Protein A or a Protein G column, which affinity agents bind to proteins that contain Fc domains. Polypeptides can be removed from an affinity column using conventional techniques, e.g., in a high salt elution buffer and then dialyzed into a lower salt buffer for use or by changing pH or other components depending on the affinity matrix utilized, or can be competitively removed using the naturally occurring substrate of the affinity moiety. In one embodiment, the antibodies produced using the methods and compositions of the invention are purified in accordance with the methods described in U.S. application Ser. No. 11/732,918, incorporated by reference herein.

The desired degree of final purity depends on the intended use of the polypeptide. The methods and compositions of the invention are suitable for therapeutic uses of the protein of interest. Thus, a relatively high degree of purity is desired when the polypeptide is to be administered in vivo. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Most preferably, the polypeptide of the invention is purified to substantial homogeneity, as indicated by a single polypeptide band upon analysis by SDS-PAGE. The polypeptide band can be visualized by silver staining, Coomassie blue staining, or (if the polypeptide is radiolabeled) by autoradiography.

The invention also optionally encompasses further formulating the proteins. By the term "formulating" is meant that the proteins can be buffer exchanged, sterilized, bulk-packaged and/or packaged for a final user. Such compositions can comprise an effective amount of the protein, in combination with other components such as a physiologically acceptable diluent, carrier, or excipient. The term "physiologically acceptable" means a non-toxic material that does not interfere with the effectiveness of the biological activity of the active ingredient(s).

It should be noted that, with respect to the numbers recited herein, numbers that are intermediate to the above ranges, as well as all other numbers recited herein, are also intended to be part of this invention. Ranges of values using a combination of any of the above recited values as upper and/or lower limits are intended to be included in the scope of the invention.

EXAMPLES

The following examples exemplify improved methods and compositions for culturing mammalian cells, including improved methods and compositions for expressing biologics in mammalian cells. An improved biochemically defined medium for culturing Chinese Hamster Ovary (CHO) cells used to express various recombinant biologics is disclosed below. Further, media for large-scale culture of cells in bioreactors run under various configurations and scales, containing the same components but with differing component balance and enriched to allow for greater cell growth and increased product expression, are also exemplified.

Example 1

Improved Media for Culturing Mammalian Cells

Typically mammalian, e.g., Chinese Hamster Ovary (CHO), cell culture media is based on commercially available media formulations, such as DMEM, Ham's F12, or combinations of these media types. For the production of proteins in mammalian cells, a cell culture medium must be sufficiently enriched to support increases in both cell growth and biologics product expression. The following example describes an improved biochemically defined medium for culturing mammalian cells, i.e., Chinese Hamster Ovary (CHO) cells to express various recombinant biologics, including antibodies.

Chinese Hamster Ovary (CHO) cells, deficient in dihydrofolate reductase [dhfr(−)] were adapted to grow in suspension in the absence of serum or any other material derived from an animal source. Cells were grown in the absence of hypoxanthine and thymidine, in defined cell culture medium obtained from a commercial source, JRH PF-CHO (Catalog #67147). Although the cell line was not deficient in glutamine synthase, additional glutamine was added to the culture medium.

CHO cell lines expressing biologics, such as antibodies to a given target, were generated using molecular biological techniques well known in the art. Briefly, an expression vector capable of expressing the antibody of interest, and capable of expressing the dhfr enzyme gene were introduced into CHO cells using methods well known in the art. Transfected cells of interest were obtained by selecting the cells in the presence of hypoxanthine and thymidine. Selected transformants were further cultured in increasing concentrations of methotrexate, to amplify the transfected genes and increase yield of expressed proteins. The improved cell culture medium used to culture the CHO cells is described below.

Example 1.1

Medium for Chinese Hamster Ovary (CHO) Cell Culture

Generally, media formulations for culturing CHO cells were made up of three parts designated Parts A, B, and C. Part A was a basal medium and comprised water, amino acids, vitamins, inorganic metal salts, trace elements, ethanolamine, putrescine, a surfactant, sodium pyruvate, glutathione, and 2-Mercaptoethanol. Part B comprised an inorganic iron source; and Part C comprised recombinant growth factors, buffers, an osmolality regulator, an energy source, various non-ferrous metal ions, a surfactant, and hydrolysates. The medium components were mostly inorganic or from a recombinant source and were highly purified. The media did not contain proteins, lipids and carbohydrates from animal sources. Complex hydrolysates were obtained from highly processed yeast and plant sources.

Part A of the medium included protein-free CHO (PF CHO) medium (JRH-SAFC Biosciences; JRH Cat #67147—also referred to as Original Part A). Thus, Part A included a basal medium, including water, amino acids and vitamins. The basal medium (PF CHO) was selected for modification and reformulation to support further increases in cell growth and expressed protein productivity. PF CHO was modified to remove certain components, including sodium bicarbonate, HEPES buffer, mono-basic sodium phosphate, di-basic sodium phosphate, an osmolarity regulator, a surfactant, and monosaccharide glucose (modified PF CHO is referred to herein as modified Part A (also referred to as JRH Catalog #67411)). These modifications were also made to facilitate improvements in cell culture process conditions in large-scale bioreactors.

The Part B component (JRH) consisted of a concentrated ferric citrate solution that was added separately. The concentration of the Part B component was held constant in all CHO cell culture projects.

Part C components included a growth factor, e.g., insulin, the amino acid glutamine, TC yeastolate and soy hydrolysate phytone, methotrexate necessary to retain selective pressure, and the base NaOH and acid HCl for adjusting the pH after the media was hydrated during preparation The improved cell culture media formulations were made as follows. First, CHO cells were originally grown in PF-CHO media (SAFC-JRH Catalog No. 67147) obtained from JRH. PF-CHO media (Catalog #67147) was further modified for use with the CHO cell lines as described below. This modified medium was designated by JRH with a new Catalog #67411. The goal of the modifications was to allow increasing concentrations of Part A of the cell culture medium, such that osmolarity and pH were unaffected. The original Part A (Cat #67147) was also declared by the manufacturer (JRH) to be without Sodium Bicarbonate, Glutamine, and Protein-free (no Insulin or other protein or peptide growth factors added). These omitted components were then added to both 67147 and 67411 Part A formulations independently, specifically for CHO cell lines when proven efficacious. These became some of the components described in more detail below as Part C.

sodium phosphates, the osmolarity regulator sodium chloride, the surfactant Pluronic F-68, and the monosaccharide Glucose from Part A. These components were added back to Part A in at various concentrations depending on the needs of the specific cell culture project. This allowed the buffer con-

TABLE 1

Comparison of original cell culture medium formulation (Part A 67147) with modified cell culture medium formulation (modified Part A 67411).

| Component | Cell culture medium containing 67147 (RM-003) (Original Part A) | Cell culture medium containing Modified 67411 (RM-230) (modified Part A) at 1X, 2X, 3X, and 4X g/L |
|---|---|---|
| Part A | | |
| Part A Original Powder: JRH Source 1X concentration only | 16.45 g/L | NA |
| Modified Part A: Special JRH Source Selected components without sodium bicarbonate, HEPES, and the mono- and di-basic sodium phoshates, the osmolarity regulator sodium chloride, the surfactant Pluronic F-68, and the monosaccharide Glucose | NA | 2.63, 5.26, 7.89, and 10.52 g/L |
| Part B | | |
| Part B: Ferric Citrate JRH Stock solution | 10 mL/L (0.5 mM) | 10 mL/L (0.5 mM) |
| Part C: | | |
| Growth Factor, monosaccharide, energy source-amino acid: multiple levels | | |
| Recombinant hu Insulin | 2-4 mg/L | 4-13 mg/L |
| Glucose | 1.5-3.5 g/L | To 7.0 g/L max |
| L-glutamine | 0.292 g/L | 0.584 g/L |
| Buffers: Held to single concentration | | |
| Sodium Bicarbonate | 1.6 g/L | 1.6 g/L |
| HEPES | NA | 1.8 g/L |
| $NaH_2PO_4$—$H_2O$ | NA | 0.031 g/L |
| $Na_2HPO_4$—$7H_2O$ | NA | 0.436 g/L |
| Osmolarity Regulator: Multiple levels per product line | | |
| NaCl | NA | 0-6.5 g/L |
| Hydrolysates: Multiple levels per product line | | |
| Bacto TC Yeastolate | NA | 2.0-10.7 g/L |
| BD Phytone (Soy) Peptone | NA | 0-6.92 g/L |
| Primatone | NA | 2-8 g/L |
| Other/Additional Agents | | |
| Selective pressure (dhfr system): Multiple levels per product line | | |
| Methotrexate | To required Amplification level | To required Amplification level |
| Surfactant-Shear protectant: Single level | | |
| Pleuronic F-68 | 1.0 g/L | 1.0 g/L |
| Acid-Base for pH adjustment | | |
| NaOH | As needed | As needed |
| HCl | As needed | As needed |
| Solution targets | | |
| Final pH | 7.2-7.4 | 7.1-7.3 |
| Final Osmolarity | 280-320 | 320-450 |

Part A of Cell Culture Medium for CHO Cell Culture

As described above, Part A of the improved cell culture medium contained a modified version of a basal medium, i.e., PF-CHO media. PF-CHO media, (Catalog No. 67147) obtained from JRH, was modified by removing the buffers sodium bicarbonate, HEPES, and the mono- and di-basic centration to be held steady, and the surfactant concentration to be kept below levels toxic to the cells, while allowing the osmolarity and the carbon substrate levels to be manipulated for increased growth of cells and increased antibody production. Once these components were separated from the original JRH Part A formulation, it facilitated increases in the concentration of the remaining components in JRH Part A as seen in the modified cell culture medium (modified PF CHO—referred to as #67411 in Table 1), thus allowing for increased cell growth, and expression of antibody as determined by antibody titer. Individual components of the modified Part A powder (67411) formulation, including amino acids, vitamins, trace elements and other miscellaneous component fractions were increased up to four times the concentration of the original formulation without having to change the volume of the media. A comparison of the original Part A formulation using 67147 and the modified formulation using 67411 is described above in Table 1.

By definition, the original JRH PF CHO basal medium (catalog #67147) was a PF CHO basal medium without glutamine and without sodium bicarbonate. The original concentration of glucose in Part 1 was 1.5 mg/L.

Part B of Cell Culture Medium for CHO Cell Culture

The Part B component of the cell culture medium comprised a concentrated ferric citrate solution, which was the same as the Part B component in PF-CHO media, (Catalog Nos. 67147) obtained from JRH, and was added separately.

Inorganic iron sources such as the ferric and ferrous salts, particularly ferric citrate and ferrous sulfate were added to the basal medium, i.e., Part A or modified Part A. Though a small amount of ferrous sulfate (0.2-0.8 mg/L) and ferric Nitrate Nonhydrate (0.025-0.11 mg/L) was added, chelated salts, such as ferric citrate, were preferred. Ferric citrate was added in greater concentration as a liquid supplement, and was included in the cell culture medium as PF-CHO Part B. Though the concentration of the other medium components could change, and have a greater range of concentration, ferric citrate was held to a single concentration of 122 mg/L. This was due to the formation of superoxides and free radicals causing cell damage, and the formation of undesired compounds in the basal medium.

Part C of Cell Culture Medium for CHO Cell Culture

Part C of the cell culture medium comprised primarily of recombinant growth factors, buffers, an osmolarity regulator, an energy source, and hydrolysates. Additional compounds added to the cell culture medium that are not included in the usual groupings of amino acids, vitamins and co-factors, inorganic salts and buffers, trace elements or minerals, in the course of development are described in Table 1 above as "Part C". With respect to Part C mentioned below in Table 1, it should be noted that the ingredients identified in Part C may be added separately or in combination.

Recombinant Growth Factors

The peptide hormone Insulin, or alternatively a recombinant analog, was added to the cell culture medium in a concentration range of 4-13 mg/L. IGF-1 can also be substituted or supplemented to the Insulin added to the cell culture medium at a concentration of 50-100 ng/L.

Osmolarity Regulator

The osmolarity in the various cell culture media was in the range of 260 mOsm to 460 mOsm. Regulation of osmolarity was through salts especially NaCl, KCl, and $KNO_3$, though all of the amino acids and the hydrolysates contribute considerably to changing osmolarity.

Energy Source

The most abundant monosaccharide in the medium was glucose (D-glucose) and was supplemented as needed. The starting concentration in the cell culture medium ranged from 3.5 to 7.0 g/L. Other sugars can also be supplemented as a metabolite or as a shear protectant, these can include maltose, mannose, galactose, or fructose.

Hydrolysates

The hydrolysates are considered an additional source of free amino acids along with di- and tri-peptides.

pH Maintenance (Buffer)

Various buffers were used to maintain pH in the cell culture medium in a range of 6.5 to 7.5. The inorganic buffers (or buffer system) used in the media included carbonates ($NaHCO_3$), chlorides ($CaCl_2$), sulphates ($MgSO_4$), and phosphates ($NaH_2PO_4$ and $Na_2HPO_4$). Organic buffers also includes Sodium Pyruvate ($C_3H_3O_3Na$) and N-[2-hydroxyethyl]piperazine-N'-[2-ethanesul-phonic acid] also known as HEPES.

Glutamine

Glutamine was also included in Part C, as it was omitted from both original Part A and modified Part A. Glutamine was included in Part C, e.g., 0.2 to 0.4 (0.29) g/L in the cell culture medium containing original Part A and 0.3 to 0.7, e.g., 0.58, in the cell culture medium containing modified Part A (see Table 1 above).

Other Components of Cell Culture Medium for CHO Cell Culture

The following provides additional components that may be added to the cell culture medium. It should be noted that additional components that may be added are not limited to the examples provided below.

Additional Peptides

Putrescine HCl salt, which aids in maintaining Endoplasmic reticulum structure and growth specific to CHO cell lines, was added from 0.4 to 1.65 mg/L to the Basal medium.

Glutathione (a tripeptide) was added in amounts ranging from 0.5 to 2.0 mg/L. 2-Mercaptoethanol was also added to 3.6 mg/L, act as reducing agents in maintaining sulfhydryls and binds and transport various metals like copper. It reduces dehydroascorbate and cystine and regenerates ascorbate and cysteine.

Methotrexate:

Methotrexate concentrations differed between product lines depending on the final amplification levels to be achieved. Using a stock solution of 2 mM concentration, the addition volumes and final concentrations are: 0.250 mL/kg yields 500 nM final for both anti-IL-12 and anti-EPO-R, 0.5 mL/kg yields 100 nM final for anti-IL-18, and finally 2.5 mL/kg yields 5000 nM final for anti-TNF alpha.

Cell Protectant/Surfactant

The media described in this example was used to grow CHO cells in suspension in all scale reactors, flasks, and spinner flasks under both agitation and sparging, which created larger shear forces. To minimize cellular damage a cell protectorant like a pluronic polyols, specifically Pluronic F-68 at a concentration of approximately 1 g/L of medium was added. Other shear mitigators including methyl cellulose at less than and equal to 1 g/L, and certain hydrolysates and plant extracts at varying concentrations up to gram quantities per liter were also used.

Amino Acids

The cell culture medium had amount ranges of amino acids as described herein. Two amino acids, Asparagine and glutamine, were added in greater starting concentrations than the other amino acids as they quickly become limiting nutrients during the course of CHO cell culture. Asparagine in particular is about 0.4 to 0.5 g/kg in the basal medium.

While asparagine was a component in Part A (including both original and modified PF CHO), the concentration of asparagine was increased by supplementing it into the cell culture medium.

The cell culture medium was capable of supporting CHO growth from very low initial densities to over $1.0 \times 10^7$ cells/ mL for a number of days depending on the concentration of the components with purpose and cellular effect of the media desired. The CHO process additionally included a growth phase and a production phase as described in later sections, and required different ranges of components. However the cell culture medium formulation proportions and identities remained the same.

Final Preparation of CHO Cell Media

Preparation of the improved cell culture medium required addition of various components in a particular order with pH adjustments using a base or acid at particular times. Base in the form of NaOH was added as the Part A basal concentration increased to aid in the dissolution of the amino acids in the formulation to a maximum pH of 10. The pH was brought down to minimum of 7.0 as the Hydrolysates were added using acid in the form of HCl. Further adjustments up to a particular pH were achieved using either the NaOH or HCl solutions as needed.

The following examples describe cell culture media based on the above for the expression of various specific antibodies.

Example 1.2

Cell Culture Medium for Culturing CHO Cells Expressing Anti-TNF Alpha Antibody

CHO cell lines expressing a fully human antibody to TNFα (i.e., adalimumab; D2E7) were cultured in the cell culture media described in Table 2.

TABLE 2

Cell culture media for culturing CHO cells expressing fully human anti-TNF alpha antibody

| Media Components | Raw Material Specification # | AF-D2E7-1XP | AF-D2E7-1XP | AF and AY-D2E7 | AY-D2E7-2XP | AY-D2E7-2XP |
|---|---|---|---|---|---|---|
| Component list: JRH Part A and Part B | Raw Material Specification # | SR-248 growth | SR-250 growth + MTX | SR-286 production prod_3XP | SR-332 growth 1 | SR-333 growth 2 |
| ABC Components Added | Final pH: | 7.2 ± 0.1 | 7.2 ± 0.1 | 7.2 ± 0.1 | 7.2 ± 0.1 | 7.2 ± 0.1 |
| | Final Osmolarity: | 280-320 | 280-320 | 370-390 | 320-360 | 320-360 |
| Part A-: unmodified-original-commercially available | RM-003 | 16.45 | 16.45 | NA | NA | NA |
| Special (Modified) Part A: salt-free | RM-230 | NA | NA | 7.89 g/kg | 5.26 g/kg | 5.26 g/kg |
| Part B: Ferric citrate: Chelated Iron source | RM-004 | 10 ml/kg | 10 mL/kg | 10 mL/kg | 10 mL/kg | 10 mL/kg |
| Part C: | | | | | | |
| rHu Insulin: Recombinant Protein Glucose regulator | SR-055 | 2.0 mL/kg (4 mg/kg) | 2.0 mL/kg (4 mg/kg) | 6.0 mL/kg (12 mg/kg) | 3.88 mL/kg (8 mg/kg) | 3.88 mL/kg (8 mg/kg) |
| Glucose, anhydrous: Carbon source | RM-011 | 3.5 g/kg | 3.5 g/kg | 7.0 g/kg | 7.0 g/kg | 7.0 g/kg |
| L-Glutamine: Amino Acid and energy source | RM-071 | 0.292 g/kg | 0.292 g/kg | 0.584 g/kg | 0.876 g/kg | 0.876 g/kg |
| NaH2PO4•H2O: Phosphate buffer | RM-200 | Part A: 0.031 g/kg | Part A: 0.031 g/kg | 0.031 g/kg | 0.031 g/kg | 0.031 g/kg |
| Na2HPO4•7H2O: Phosphate buffer | RM-233 | Part A: 0.436 g/kg | Part A: 0.436 g/kg | 0.436 g/kg | 0.436 g/kg | 0.436 g/kg |
| Bacto TC Yeastolate: Yeast source hydrolysate | RM-216 | 2.0 g/kg | 2.0 g/kg | 10.7 g/kg | 4.0 g/kg | 4.0 g/kg |
| Phytone Peptone: Plant-Soy Source hydrolysate | RM-238 | NA | NA | 6.92 g/kg | 2.6 g/kg | 2.6 g/kg |
| Sodium Bicarbonate: Buffer: CO2-pH regulator | RM-077 | 1.6 g/kg | 1.6 g/kg | 1.6 g/kg | 1.6 g/kg | 1.6 g/kg |
| HEPES: Organic buffer | RM-090 | NA | NA | 1.8 g/kg | 1.8 g/kg | 1.8 g/kg |
| NaCl (Salt): Osmolarity regulator | RM-174 | Part A: 6.5 g/kg | Part A: 6.5 g/kg | 2.45 g/kg | 2.67 g/kg | 2.67 g/kg |
| Other components: | | | | | | |
| L-Asparagine monohydrate: Amino Acid | RM-284 | NA | NA | NA | 0.45 g/kg | 0.45 g/kg |
| Pluronic F-68 (Poloxamer 188, NF): Surfactant, Carrier | RM-188 | NA | NA | 1.0 g/kg | 1.0 g/kg | 1.0 g/kg |
| Methotrexate: Selective in the CHO amplification DHFR system | SR-133 | 2.50 mL/kg | 2.50 mL/kg | 2.50 mL/kg | 2.50 mL/kg | 2.50 mL/kg |
| NaOH, 2N: Base | SR-288 | As needed | As needed | 5.67 mL/kg | 3.5 mL/kg | 3.5 mL/kg |
| HCl, 2N: Acid | SR-287 | As needed | As needed | 2.5 mL/kg | 2.91 mL/kg | 2.91 mL/kg |

Example 1.3

Media Composition for Culturing CHO Cells Expressing IL-12 Antibody

The CHO cell line, expressing a fully human, anti IL-12 antibody was cultivated in a growth medium, described in Table 3.

TABLE 3

Media for culturing CHO cells expressing fully human anti-IL12 antibody (ABT-874)

| Media Name, | Raw Material Specification # | ABT-874 SR-383 growth | ABT-874 SR-352 Production | ABT-874 SR-468 Feed | ABT-874 SR-351 Glu feed | ABT-874 SR-274 | ABT-874 SR-273 | ABT-874 SR-272 |
|---|---|---|---|---|---|---|---|---|
| Final pH:, | | | | | | 6.5-6.9 | 6.5-6.9 | 6.5-6.9 |
| Final Osmolarity: | | | | | | 265-282 | 265-282 | 265-282 |
| Part A-: unmodified-original-commercially available | RM-003 | NA | NA | NA | NA | 16.45 g/kg | 16.45 g/kg | 16.45 g/kg |
| Part A (Modified): salt-free | RM-230 | 5.26 g/kg | NA | NA | NA | NA | NA | NA |
| Part A (Modified): salt-free & reduced vitamins | RM-322 | NA | 7.89 g/kg | 21.0 g/kg | 7.89 g/kg | NA | NA | NA |
| Part B: Ferric citrate: Chelated Iron source | RM-004 | 10 mL/kg | 10 mL/kg | NA | 10 mL/kg | 10 mL/kg | 10 mL/kg | 10 mL/kg |
| Part C: | | | | | | | | |
| Bovine Transferrin: Animal source Fe carrier | SR-057 | NA | NA | NA | NA | NA | NA | NA |
| rHu Insulin: Recombinant Protein Glucose regulator | SR-055 | 3.88 mL/kg | 6.5 mL/kg | NA | 6.5 mL/kg (13 mg/kg) | 2 mL/kg (4 mg/L) | 2 mL/kg (4 mg/L) | 2 mL/kg (4 mg/L) |
| Glucose, anhydrous: Carbon source | RM-011 | 7.0 g/kg | 7.0 g/kg | 150 g/kg | 200 g/kg | 3.5 + 1.5 g/kg | 3.5 + 1.5 g/kg | 200 g/L |
| L-Glutamine: Amino Acid and energy source | RM-071 | 0.876 g/kg | 0.584 g/kg | NA | 0.584 g/kg | 0.292 g/kg | 0.292 g/kg | 0.292 g/kg |
| Sodium Bicarbonate: Buffer: $CO_2$-pH regulator | RM-077 | 1.60 g/kg | 1.60 g/kg | NA | 1.6 g/kg | 1.6 g/kg | 1.6 g/kg | 1.6 g/kg |
| HEPES: Organic buffer | RM-090 | 1.80 g/kg | 1.80 g/kg | NA | 1.8 g/kg | NA | NA | NA |
| NaCl (Salt): Osmolarity regulator | RM-174 | 2.675 g/kg | 2.45 g/kg | NA | 2.45 g/kg | NA | NA | NA |
| $NaH_2PO_4 \cdot H_2O$: Phosphate buffer | RM-200 | 0.031 g/kg | 0.031 g/kg | NA | 0.031 g/kg | NA | NA | NA |
| $Na_2HPO_4 \cdot 7H_2O$: Phosphate buffer | RM-233 | 0.436 g/kg | 0.436 g/kg | NA | 0.436 g/kg | NA | NA | NA |
| Bacto TC Yeastolate: Yeast source hydrolysate | RM-216 | 4.0 g/kg | 10.7 g/kg | 65.0 g/kg | 10.7 g/kg | 2 g/kg | 11 g/kg | 8 g/kg |
| Phytone Peptone: Plant-Soy Source hydrolysate | RM-238 | 2.579 g/kg | 6.92 g/kg | 41.0 g/kg | 6.92 g/kg | NA | NA | NA |
| Other components | | | | | | | | |
| Pluronic F-68 (Poloxamer 188, NF): Surfactant, Carrier | RM-188 | 1.00 g/kg | 1.00 g/kg | NA | 1.0 mL/kg | NA | NA | NA |
| L-Asparagine monohydrate: Amino Acid | RM-284 | 0.450 g/kg | NA | 5.0 g/kg | NA | NA | NA | NA |
| Primatone: Beef-Animal Source hydrolysate | RM-149 | NA | NA | NA | NA | NA | NA | NA |
| Methotrexate: Selective in the CHO amplification DHFR system | SR-133 | 0.250 mL/kg | NA | NA | NA | 0.250 mL/kg | 0.250 mL/kg | 0.250 mL/kg |
| NaOH, 2N: Base | SR-288 | 3.50 mL/kg | 5.67 mL/kg | As needed | 5.67 mL/kg | As needed | As needed | As needed |
| HCl, 2N: Acid | SR-287 | 2.91 mL/kg | 2.5 mL/kg | As needed | 2.5 mL/kg | As needed | As needed | As needed |

With respect to the modified basal medium which is salt-free and has reduced vitamins, referenced above, the vitamin amount is reduced one third relative to unmodified basal medium, described above as RM-003, or modified salt-free basal medium, described above as RM-230. Thus, a reduced vitamin basal medium, as described above, has one third the amount of vitamins as RM-003 and RM-230. When used in amounts given in the above table, the final concentration of vitamins in the media is reduced to a third, in contrast to having used RM-003 or RM-230. It should be noted, however, that if needed, production and feed medium using RM-230 may also be used.

Example 1.4

Media Composition for Culturing CHO Cells Expressing IL-18 and EPO/R Antibodies

Table 4 provides a summary of the growth and production media used to express anti-IL18 and anti-EPO/R antibodies. Additional details regarding the media for expressing these antibodies can be found in Table 5 (anti-IL-18) and Table 6 (anti-EPO/R).

The IL-18 expressing CHO cell line was cultivated in a growth medium 2×P(SR-371), and later produced antibody in a production medium 3×P(SR-372) for a final titer of approximately 1 g/L. The high titer process used 4×P(SR-382) as the production medium to reach a final titer of approximately 2 g/L. The production medium used for anti-EPO/R production was identical to SR-286, but a 1×P medium (SR-274) was used for cell growth. All media are described in Tables 4 and 5.

Example 1.5

Cell Culture Processes for Producing Antibodies in Mammalian Cells

The medium disclosed above was also developed into two production platforms used in two projects for culturing mammalian, i.e., CHO, cells. The first platform was developed using the similar medium composition as described in the modified production medium described in Tables 2-4 above, with the only difference being in the temperature used for cell culture. This platform was used for the production of anti-IL18 antibody as well as the production of anti-erythropoietin receptor (anti-EPO/R). The second medium platform further

TABLE 4

Medium for culturing CHO cells expressing fully human anti-IL18 and anti-EPO/R antibodies

| Media Components | | Anti-IL18-2XP | Anti-IL18 3xP | Anti-IL18 4XP | Anti-EPO/R 1XP | Anti-EPO/R 3xP |
|---|---|---|---|---|---|---|
| Component list: JRH Part A and Part B<br>ABC Components Added | Raw Material Specification #<br>Final pH:<br>Final Osmolarity: | SR-371<br>growth<br>7.0 ± 0.1<br>280-300 | SR-372<br>production<br>6.9 ± 0.05<br>373-403 | SR-382<br>production<br>7.0 ± 1.0<br>360-400 | SR-274<br>growth<br>7.2 ± 0.1<br>280-320 | SR-286<br>production<br>7.2 ± 0.1<br>370-390 |
| Part A-: unmodified-original-commercially available | RM-003 | NA | NA | NA | 16.45 | NA |
| Special (Modified) Part A: salt-free | RM-230 | 5.26 g/kg | 7.89 g/kg | 10.52 g/kg | NA | 7.89 g/kg |
| Part B: Ferric citrate: Chelated Iron source | RM-004 | 10 mL/kg | 10 mL/kg | 10 mL/kg | 10 mL/kg | 10 mL/kg |
| Part C: | | | | | | |
| rHu Insulin: Recombinant Protein Glucose regulator | SR-055 | 3.88 mL/kg (8 mg/kg) | 6.0 mL/kg (12 mg/kg) | 6.5 mL/kg (12 mg/kg) | 2.0 mL/kg (4 mg/kg) | 6.0 mL/kg (12 mg/kg) |
| Glucose, anhydrous: Carbon source | RM-011 | 7.0 g/kg | 7.0 g/kg | 7.0 g/kg | 1.5 g/kg | 7.0 g/kg |
| L-Glutamine: Amino Acid and energy source | RM-071 | 0.876 g/kg | 0.584 g/kg | 0.584 g/kg | 0.292 g/kg | 0.584 g/kg |
| Sodium Bicarbonate: Buffer: $CO_2$-pH regulator | RM-077 | 1.6 g/kg | 1.6 g/kg | 1.6 g/kg | 1.6 g/kg | 1.6 g/kg |
| HEPES: Organic buffer | RM-090 | 1.8 g/kg | 1.8 g/kg | 1.8 g/kg | NA | 1.8 g/kg |
| NaCl (Salt): Osmolarity regulator | RM-174 | 2.67 g/kg | 2.45 g/kg | 2.45 g/kg | Part A: 6.5 g/kg | 2.45 g/kg |
| $NaH_2PO_4 \cdot H_2O$: Phosphate buffer | RM-200 | 0.031 g/kg | 0.031 g/kg | 0.031 g/kg | Part A: 0.031 g/kg | 0.031 g/kg |
| $Na_2HPO_4 \cdot 7H_2O$: Phosphate buffer | RM-233 | 0.436 g/kg | 0.436 g/kg | 0.436 g/kg | Part A: 0.436 g/kg | 0.436 g/kg |
| Bacto TC Yeastolate: Yeast source hydrolysate | RM-216 | 4.0 g/kg | 10.7 g/kg | 14.27 g/kg | 2.0 g/kg | 10.7 g/kg |
| Phytone Peptone: Plant-Soy Source hydrolysate | RM-238 | 2.6 g/kg | 6.92 g/kg | 9.23 g/kg | NA | 6.92 g/kg |
| Other: | | | | | | |
| L-Asparagine monohydrate: Amino Acid | RM-284 | 0.45 g/kg | NA | NA | NA | NA |
| Pluronic F-68 (Poloxamer 188, NF): Surfactant, Carrier | RM-188 | 1.0 g/kg | 1.0 g/kg | 1.0 g/kg | NA | 1.0 g/kg |
| Methotrexate: Selective in the CHO amplification DHFR system | SR-133 | 0.05 mL/kg | 0.05 mL/kg | 0.05 mL/kg | 0.25 mL/kg | 2.50 mL/kg |
| NaOH, 2N: Base | SR-288 | As needed | As needed | As needed | As needed | 5.67 mL/kg |
| HCl, 2N: Acid | SR-287 | As needed | As needed | As needed | As needed | 2.5 mL/kg | strengthening the nutritional components, was used for high-titer anti-IL18 production, to achieve higher volumetric antibody productivity.

All antibodies, including anti-IL-12, anti-IL-18 and anti-EPO/R antibodies were fully human IgG1 antibodies expressed by transfected dhfr(−) CHO cell lines as described previously. These cell lines were cultivated in suspension and without the aid of bovine source serum or other animal source materials.

To produce anti-IL 18 antibodies, the anti-IL 18 expressing CHO cell line, was cultivated in a growth medium, herein referred to as SR-371. Medium SR-371 was used to support higher cell productivity with moderate cell growth. Once the cell density reached the transfer criteria, the cells were transferred into the production medium (SR-372) to start the production stage.

TABLE 5

Compositions of culture media in Anti-IL18 Process A. Growth medium SR-371 was used in see train and seed reactors. Production medium SR-372 was used in 3000-liter production bioreactor.

| Component | Growth medium SR-371 | Production Medium SR-372 |
|---|---|---|
| PFCHO Part A, special salt-free formulation | 5.26 g/L | 7.89 g/L |
| PFCHO Part B (ferric citrate stock solution) | 10 mL/L | 10 mL/L |
| Recombinant human insulin | 7.76 mg/L | 13 mg/L |
| Dextrose, anhydrous | 7.0 g/L | 7.0 g/L |
| L-glutamine | 0.876 g/L | 0.584 g/L |
| Sodium bicarbonate | 1.6 g/L | 1.6 g/L |
| HEPES | 1.8 g/L | 1.8 g/L |
| NaCl | 2.67 g/L | 2.45 g/L |
| Pluronic F-68 (Poloxamer 188, NF) | 1.0 g/L | 1.0 g/L |
| $NaH_2PO_4 \cdot H_2O$ | 0.031 g/L | 0.031 g/L |
| $Na_2HPO_4 \cdot 7H_2O$ | 0.436 g/L | 0.436 g/L |
| Bacto TC Yeastolate | 4.0 g/L | 10.7 g/L |
| Phytone Peptone | 2.579 g/L | 6.92 g/L |
| Methotrexate, 2 mM | 0.05 mL/L | 0.05 mL/L |
| NaOH, 2N | — | 3.5 mL/L | 5.67 mL/L |
| HCl, 2N | 2.91 g/L | 2.5 mL/L |
| Final pH | 7.10-7.20 | 7.10-7.20 |
| Final osmolality (mOsmo/kg) | 373-403 | 373-403 |

The temperature was maintained at 35° C. throughout the culture. Additional 4 g/L of glucose was added when the cell culture glucose level was below 2 g/L.

A similar process was also employed for the anti-EPO/R antibody production. However, a leaner medium (SR-274) was used for cell growth in the seed train. Medium SR-286, the same medium used for Humira production, was used at the production stage for anti-EPO/R antibody (Table 6). Growth medium SR-274 was used in seed train and seed reactors. Production medium SR-286 was used in 3000-liter production bioreactor.

TABLE 6

Compositions of culture media in Anti-EPO/R Process

| Component | Growth medium SR-274 | Production medium SR-286 |
|---|---|---|
| PFCHO Part A, RM-003 | 16.45 g/Kg | N/A |
| PFCHO Part A, RM-230 (salt-free) | N/A | 7.89 g/Kg |
| PFCHO Part B (ferric citrate stock solution) | 10 mL/Kg | 10 mL/Kg |
| Recombinant human insulin | 4 mg/Kg | 13 mg/Kg |
| Dextrose, anhydrous | 1.5 g/Kg | 7.0 g/Kg |
| L-glutamine | 0.292 g/Kg | 0.584 g/Kg |
| Sodium bicarbonate | 1.6 g/Kg | 1.6 g/Kg |
| HEPES | N/A | 1.8 g/Kg |

TABLE 6-continued

Compositions of culture media in Anti-EPO/R Process

| Component | Growth medium SR-274 | Production medium SR-286 |
|---|---|---|
| NaCl | N/A | 2.45 g/Kg |
| Pluronic F-68 (Poloxamer 188, NF) | N/A | 1.0 g/Kg |
| $NaH_2PO_4 \cdot H_2O$ | N/A | 0.031 g/Kg |
| $Na_2HPO4 \cdot 7H_2O$ | N/A | 0.436 g/Kg |
| Bacto TC yeastolate | 2.0 g/Kg | 10.7 g/Kg |
| Phytone peptone | N/A | 6.92 g/Kg |
| Methotrexate, 2 mM | 0.25 mL/Kg | N/A |
| NaOH, 2N | As needed | 5.67 mL/Kg |
| HCl, 2N | As needed | 2.5 mL/Kg |
| Final pH | 7.20 ± 0.10 | 7.15 ± 0.05 |
| Final osmolality (mOsmo/kg) | 320 ± 20 | 388 ± 15 |

Growth medium SR-274 was used in spinner flasks, Wave bag, 100 L seed bioreactor Z-4605 and the initial stage of 575 L culture in the 3000 L production bioreactor Z-3600. Production medium SR-286 was used in 3000 L production bioreactor Z-3600 only.

The production media SR-286 and SR-372 consisted of similar medium components as listed in Tables 5 and 6 but with different level of MTX (0 nM for SR-286 and 100 nM for SR-372).

An improved process was developed for anti-IL18 production to obtain higher productivity. This new process, Process B, introduced a new medium for extending cell culture longevity and increasing antibody volumetric productivity. The production medium (SR-382) was different from the previous production media on the amount of nutrients used at the production stage. The full composition of SR-382 is described in Table 7. In the new process for anti-IL18 production, although cells were still cultivated in medium SR-371 during the seed train, medium SR-372 was used in the seed bioreactor one-step before the production stage. Cells were then cultivated in medium SR-382 at the production stage with a temperature shift from 35° C. to 33° C. to prolong the cell culture longevity therefore extending the effects of medium SR-382 to the cells.

Growth medium SR-371 was used in spinner flasks, Wave bag, and 100 liter seed bioreactor. Short-fill medium SR-372 was used in the initial stage of 575-liter culture in the 3000-liter production bioreactor. Production medium SR-382 was used in the 3000-liter production bioreactor only.

TABLE 7

Compositions of culture media in Anti-IL18 Process B

| Component | Growth medium SR-371 | Short-fill medium SR-372 | Production medium SR-382 |
|---|---|---|---|
| PFCHO Part A, special salt-free formulation | 5.26 g/L | 7.89 g/L | 10.52 g/L |
| PFCHO Part B (ferric citrate stock solution) | 10 mL/L | 10 mL/L | 10 mL/L |
| Recombinant human insulin | 7.76 mg/L | 13 mg/L | 13 mL/L |
| Dextrose, anhydrous | 7.0 g/L | 7.0 g/L | 7.0 g/L |
| L-glutamine | 0.876 g/L | 0.584 g/L | 0.584 g/L |
| Sodium bicarbonate | 1.6 g/L | 1.6 g/L | 1.6 g/L |
| HEPES | 1.8 g/L | 1.8 g/L | 1.8 g/L |
| NaCl | 2.67 g/L | 2.45 g/L | 0 g/L |
| Pluronic F-68 (Poloxamer 188, NF) | 1.0 g/L | 1.0 g/L | 1.0 g/L |
| $NaH_2PO_4 \cdot H_2O$ | 0.031 g/L | 0.031 g/L | 0.031 g/L |
| $Na_2HPO4 \cdot 7H_2O$ | 0.436 g/L | 0.436 g/L | 0.436 g/L |
| Bacto TC Yeastolate | 4.0 g/L | 10.7 g/L | 14.27 g/L |
| Phytone Peptone | 2.579 g/L | 6.92 g/L | 9.23 g/L |
| Methotrexate, 2 mM | 0.05 mL/L | 0.05 mL/L | 0.05 mL/L |
| NaOH, 2N | 3.5 mL/L | 5.67 mL/L | 8.95 mL/L |
| HCl, 2N | 2.91 g/L | 2.5 mL/L | 4.1 mL/kg |

TABLE 7-continued

Compositions of culture media in Anti-IL18 Process B

| Component | Growth medium SR-371 | Short-fill medium SR-372 | Production medium SR-382 |
|---|---|---|---|
| Final pH | 7.1-7.2 | 7.1-7.2 | 7.1-7.2 |
| Final osmolality (mOsm/kg) | 373-403 | 373-403 | 373-403 |

Nutrients were enriched in this medium to further provide the energy sources and building components for CHO cell growth and antibody production. In the process B, although cells were still cultivated in medium SR-371 during the seed train, medium SR-372 was used in the seed bioreactor one-step before the production stage. Cells were then cultivated in medium SR-382 at the production stage with a temperature shift from 35° C. to 32° C. to prolong the cell culture longevity therefore extending the effects of medium SR-382 to the cells.

Process A: Performance of Anti-IL 18 Cells and Anti-EPO/R cells in Medium SR-372 and Medium SR-286

Anti-IL18 expressing cells were cultivated in medium SR-371 with 100 nM MTX to accumulate cell mass for the production stage. Medium SR-371 was used to support higher cell productivity with moderate cell growth. Table 8 shows a representative production growth profile of Anti-IL18 producing CHO cells in the 3000 L production bioreactor. Using this process (Process A) with medium SR-372, a final titer up to 1 g/L can be obtained.

TABLE 8

Production of Anti-IL18 antibody in Medium 372 (Process A)

| Measurable Results | Bench-scale process (n = 5) Temp = 35° C. | 3000 L Process (n = 6) Temp = 35° C. |
|---|---|---|
| Maximum Cell Density [$10^6$ viable cells/ml] | 8.68 | 9.2 |
| Duration to 50% Viability [Days] | 11 | 11 |
| Cell Specific Productivity [pg/cell-day] | 20.5 | 17.6 |
| Volumetric Productivity to Harvest @ 50% Viable [mg/L-day] | 98.8 | 81.8 |
| Titer @ 50% Viable [mg/L] | 1004 | 900 |

Medium 286, which shares same formulation as Medium 372 except for the MTX level, was used for anti-EPO/R production. Although usually a lower cell density is obtained at the production stage, a higher productivity was reached to enable the cells producing up to 1.8 g/L of antibody at 3000 L scale by using medium SR-286 as the production medium. Reasonable cell growth was observed as summarized in Table 9. Bench-scale results as well as results from 3000 L run demonstrated that this medium increased cell specific productivity and a final titer up to 1.9 g/L was observed. These results show that media with the similar formulation (SR-372 and SR-286 in Tables 1 and 2) support good cell growth and high antibody production rates in large scale CHO cell culture.

TABLE 9

Production of Anti-EPO/R antibody in Medium 286

| Measurable Results | Bench-scale process (n = 2) Temp = 35° C. | 3000 L Process (n = 1) Temp = 35° C. |
|---|---|---|
| Maximum Cell Density [$10^6$ viable cells/ml] | 4.50 | 4.80 |
| Duration to 50% Viability [Days] | 13 | 13 |
| Cell Specific Productivity [pg/cell-day] | 38.0 | 53.2 |
| Volumetric Productivity to Harvest @ 50% Viable [mg/L-day] | 114.4 | 146.1 |
| Titer @ 50% Viable [mg/L] | 1487 | 1900 |

Process B: Performance of Anti-IL 18 cells in Process B with Medium SR-382

Medium SR-382 was the most enriched medium used in the extended batch process for anti-IL-18 antibody production. Process B includes using medium SR-371 in the seed train and SR-372 in the seed bioreactor before the production stage, or the short-fill stage. The cell growth was moderate compared to the cell growth in medium SR-372 at the production stage. However, with the temperature shift, a final titer up to 2.5 g/L was obtained using Medium SR-382.

Medium SR-382 was developed based on the study showing that the cell specific productivity of anti-IL18 expressing cells proportionally increased with increasing nutrients in the production media. Medium SR-382 was the optimal medium which provided the balance between cell growth and final titer increase. Although the maximum cell density only reached $5.9 \times 10^6$ cells/mL, the cell specific productivity increased two-fold. Combining with temperature shift to prolong the cell culture duration, a final titer up to 2.2 g/L was achieved as shown in Table 10.

TABLE 10

Production of Anti-IL18 antibody in Medium SR-382 (Process B)

| Measurable Results | Bench-scale process (n = 2) Temp = 35-33° C. | 3000 L Process (n = 1) Temp = 35-33° C. |
|---|---|---|
| Maximum Cell Density [$10^6$ viable cells/ml] | 7.85 | 5.90 |
| Duration to 50% Viability [Days] | 12 | 13 |
| Cell Specific Productivity [pg/cell-day] | 32.0 | 42.1 |
| Volumetric Productivity to Harvest @ 50% Viable [mg/L-day] | 181.1 | 191.8 |
| Titer @ 50% Viable [mg/L] | 2173 | 2110 |

Example 2

Improved Fed Batch Process and Feed Solutions for Expressing Antibodies

Spent medium analysis of bioreactors run in batch mode showed depletion of certain amino acids. This finding also suggested depletion of other medium components, even if not measured, which could lead to additional nutritional deficiencies. In other to compensate for these potential deficiencies, solutions of nutrients were added. In the engineering field, this approach is generally referred to as fed-batch.

For an operational point of view it is convenient to use concentrated feed solutions. The following examples describe the addition of highly concentrated solutions of the chemically defined basal medium (PFCHO, Catalog #67411-50L) and of complex hydrolyzates, e.g., yeastolate and phytone. It was determine that this pair of hydrolyzates exhibited a productivity increase synergistic effect related to their concentration ratio.

Example 2.1

Adalimumab Fed Batch Process

The initial adalimumab (Humira/D2E7) process consisted of a 3 day process in which media was removed and replenished eight consecutive times. An improved fed batch process was developed by replacing in the medium the hydrolyzate Primatone with the hydrolyzate Yeastolate and by using new reactor parameters. The improved fed batch process lasted approximately 12 days.

The productivity of the initial batch process was further improved by re-formulating the basal medium, PFCHO, and adding a new hydrolyzate, i.e., Phytone. This hydrolyzate containing media formulation was used in the process referred to above as SR-286 (see Table 2). Reactor operating parameters were also investigated which resulted in the identification of an optimal temperature to run the entire adalimumab production process.

Analysis of samples taken daily from the reactor experiments highlighted some potential nutritional deficiencies. For the case of the adalimumab batch process, the potential nutritional deficiency was addressed by feeding a 25× concentrated PFCHO solution and a 33× solution of the hydrolyzates yeastolate and phytone. The hydrolyzates are complex components that exhibit a synergistic effect related to their concentration ratio. This ratio was maintained in a highly concentrated 33× version.

Experimental Plan

The goal of the experiment was to compare the new fed batch process to two batch control processes (temperature shift 37→33° C. vs. constant temperature 35° C.).

The fed-batch modifications were:
1. 25× basal media enrichment (PFCHO solution) fed based on amino acid deficiencies.
2. 33× hydrolyzate enrichment solution fed at intervals so that the osmolarity of the media never exceeded 440 mOsm (a condition that results in reduced cell growth and viability)
3. The reactor temperature set-point to be 35° C. throughout.

The controls for this experiment were:
a) An identical reactor operating with the current media (SR-286) and under control batch process parameters (control conditions included reactors running SR-286 medium with a temperature shift and linear pH ramp), designated as control #1; and
b) An identical reactor operating with the current media (SR-286) and under all the current batch process parameters except for an operating temperature of 35° C. throughout, designated as control #2.

Materials
Braun ED reactors with a working volume of 13 L
Pilot Plant Inoculum AFI915A using Working Cell Bank WCB970513-6
3XP11Y7P Basal media solution (SR-286)
Basal Media Enrichment Solution (25×) (PF CHO solution)
Hydrolysate Enrichment Solution (33×)
Glucose Feed Shot (200 g/L) (Glucose solution)
0.5N Sodium Hydroxide Solution for pH control Solution Preparation:
1. Production Medium (see SR-286 Solution Record described above in Table 2)
2. 2 kg of PFCHO Enrichment Solution (25×) (Basal enrichment solution):
   Prepared in the following order, under constant stirring and allowing mixing for 10 minutes after each addition step:

| Component | Mass [g] | Notes |
|---|---|---|
| MilliQ $H_2O$ | 1500 | |
| PFCHO | 131.5 | |
| 10N NaOH | 49 mL | Until pH 10 |
| Asparagine | 15 | pH will drop to ~9.73 |
| Glucose | 100 | pH will drop to ~9.71 |
| MilliQ $H_2O$ | As required | Bring weight to 2000 g, pH ~9.70, osmolarity ~1480 mOsm |
| Filter with 0.2µ PES filter membrane | | |
| Store at 4° C. | | |

Every addition of 1% of initial volume of the above solution will increase:
a) PFCHO concentration by 0.25x compared to original 3x concentration
b) Asparagine by 75 mg·$L^{-1}$
c) Glucose concentration by 0.5 g·$L^{-1}$
d) Osmolarity by 10 mOsm
e) pH by ~0.10 pH units 3. 1 Kg Hydrolysate Enrichment Solution (33×):
   Prepared in the following order, under constant stirring and allowing mixing for 10 minutes after each addition step:

| Component | Mass [g] | Notes |
|---|---|---|
| MilliQ $H_2O$ | 500 | |
| TC Yeastolate | 265 | |
| Phytone Peptone | 165 | |
| MilliQ $H_2O$ | As required | Bring weight to 1000 g |
| Filter with 0.2µ PES filter membrane | | |
| Store at 4° C. | | |

Note:
Every addition of 1% of initial volume of the above solution will increase:
a) TC Yeastolate concentration by 2.65 g/L (0.33x) compared to original batch concentration.
b) Phytone Peptone concentration by 1.65 g/L (0.33x) compared to original batch concentration.

Methods:
Reactor Operation:
To inoculate the reactor, a vial was thawed and expanded following the Humira seed train process description. After growing in the reactor, the reactor was drained down to 3.62 L to simulate the shortfill stage. Then reactor was topped off to 13 L level with production media (SR-286).

Reactors were operated with the following parameters:
a) Agitation 70 RPM
b) Temperature 35° C.
c) pH linear ramp started from pH 7.16 to pH 6.90 over a 72 hour period
d) Dissolved oxygen 30%
e) Reactors were fed 195 g of a 200 g/L glucose solution when glucose level was under 2.0 g·$L^{-1}$ Feeding Schedule:
The following represents the feeding schedule for adding the additional nutrients, i.e., supplemental basal medium, and hydrolyzates to the adalimumab batch.

TABLE 11

Feed schedule adalimumab fed batch process

| Day | Feed Amounts [g] 25x PFCHO | 33x Hydrolyzates |
|---|---|---|
| 0-3 | | |
| 4 | 130 | 130 |
| 5 | | |
| 6 | 260 | |
| 7 | | 130, glucose |
| 8 | | |
| 9 | 260, glucose | |
| 10 | | |
| 11 | 130 | |
| 12-13 | | |

Results:

Results (as well as projected improvements) comparing control processes #1 and #2 to the improved fed batch process are described in Tables 12 and 13. As shown in Table 12, adalimumab productivity increased with the addition of enhanced enriched basal media and hydrolyzate enrichment solution using the improved fed batch process under constant temperature.

TABLE 12

Comparison of adalimumab fed batch processes

| Measurable Results | Control #1 (3000 L Process) Temp = 37° C. ↓ 33° C. | Control #2 (3000 L Process) Temp = 35° C. | Fed-Batch Experiment Temp = 35° C. |
|---|---|---|---|
| Maximum Cell Density [$10^6$ viable cells/ml] | 3.63 | 4.45 | 4.41 |
| Duration to 50% Viability [Days] | 13 | 10 | 12 |
| Cell Specific Productivity [pg/cell-day] | 42.5 | 46.7 | 61.4 |
| Volumetric Productivity to Harvest @ 50% Viable [mg/L-day] | 98 | 114 | 163 |
| Titer @ 50% Viable [mg/L] | 1322 | 1178 | 1979 |

TABLE 13

Comparison of projected results using adalimumab fed batch processes

| Projected outcome | Control #1 (3000 L Process) Temp = 37° C. ↓ 33° C. | Control #2 (3000 L Process) Temp = 35° C. | Fed-Batch Experiment Temp = 35° C. |
|---|---|---|---|
| Harvests per Year [Allowing 3 day turn around] | 22 | 28 | 24 |
| Yearly Product Yield (Based on 2600 L Harvest) [Kg/year] | 75.6 | 85.7 | 123.4 |
| Increased Yearly Yield (control = 100%) | 100% | 114% | 163% |

Example 2.2

ABT-874 Fed Batch Process

As for the case of the improved fed batch process for adalimumab mentioned above, analysis of samples taken daily from the reactor running ABT-874 in batch mode highlighted amino acid depletion. Again, this deficiency was addressed by using a 25×PFCHO solution and the concentrated 33× hydrolyzate solution.

The batch process for ABT-874 was originally developed for D2E7 (adalimumab) by replacing the hydrolyzate in the media and by introducing new reactor parameters. Furthermore, as in the case of D2E7 (adalimumab), the basal media was reformulated and a new hydrolyzate was added. This media formulation is used in the current D2E7 process as SR-286 (see Table 2 above).

Experimental Plan:

The goal of the experiment was to compare a control batch process to the following fed-batch conditions, both beginning on the time when amino acid depletion had been previously identified:

a) Feed alternatively basal media enrichment 25×PFCHO and 33× hydrolyzate enrichment solutions
b) Feed daily both basal media enrichment 25×PFCHO and 33× hydrolyzate enrichment solutions The control for this experiment included an identical reactor operating with the current media (SR-286) and under the control batch process parameters (SR-286 medium, with a temperature shift and linear pH ramp).

Materials:
Braun ED reactors with a working volume of 13 L
Working Cell Bank W990107-J695
3XP11Y7P Basal media solution (SR-286-111899-1)
PFCHO-0-500-HG2Y Growth Media
Basal Media Enrichment Solution (25×)
Hydrolysate Enrichment Solution (33×)
0.5N Sodium Hydroxide Solution Solution Preparation:
1. Production medium (see SR-286 Solution Record)
2. 25×PFCHO Solution (basal enrichment solution: described in previous example; with the exception that 462 g of glucose solution were used instead of glucose powder, thus the final weight was 2170 g).
Note: Every addition of 1% of initial volume of the above solution will increase:
a) PFCHO concentration by 0.25× compared to original 3× concentration
b) Asparagine by 75 mg·L$^{-1}$
c) Glucose concentration by 2.1 g·L$^{-1}$
pH by ~0.10 pH units
3. 33× Hydrolysate Solution (Described in the previous example with the addition of 2.40 g·L$^{-1}$ of glucose)
Note: addition of 1% of initial volume of the above solution will increase:
a) TC Yeastolate concentration by 2.65 g/L (0.33×) compared to original batch concentration.
b) Phytone Peptone concentration by 1.65 g/L (0.33×) compared to original batch concentration.

Method:

To inoculate the reactor, a vial was thawed and expanded following the ABT-874 seed train process description. After growing in the reactor, the reactor was drained down to 4.06 Liters (run designation B9013-ED2 and B9014-ED3, as described in Table 13) to simulate shortfill. The reactor was then topped off to 13 L level with regular production media (SR-286)

Reactors were operated according to the following parameters:
a) Agitation 70 RPM
b) Temperature 33° C.
c) pH 6.90
d) Dissolved oxygen 40%

TABLE 13

Feeding Schedule for ABT-874

Feed Amounts [g]

| | Alternate Feeding Schedule Run Designation B9013-ED2 | | Daily Feeding Schedule Run Designation B9014-ED3 | |
|---|---|---|---|---|
| | 25x PFCHO | 33x Hydrolyzates | 25x PFCHO | 33x Hydrolyzates |
| 0-4 | | | | |
| 5 | 130 | | 65 | 65 |
| 6 | | 130 | 65 | 65 |
| 7 | 130 | | 65 | 65 |
| 8 | | 130 | 65 | 65 |
| 9 | 130 | | 65 | 65 |
| 10 | | 130 | 65 | 65 |
| 11 | 130 | | 65 | 65 |
| 12 | | 130 | 65 | 65 |
| 13 | 130 | | 65 | 65 |
| 14-15 | | | | |

Results

Results comparing the improved fed batch processes are described below in Tables 14 and 15.

TABLE 14

Fed batch process results

| Parameter | Control (1000 L Process) Temp = 33° C. | Alternate Fed-Batch Experiment Temp = 33° C. | Daily Fed-Batch Experiment Temp = 33° C. |
|---|---|---|---|
| Maximum Cell Density [$10^6$ cell/ml] | 3.79 | 5.39 | 4.15 |
| Duration to 50% Viability [Days] | 14 to 76% | 15 | 15 |
| Cell Specific Productivity [pg/cell-day] | 71 | 83 | 82 |
| Volumetric Productivity to Harvest @ 50% Viable [mg/L-day] | 188 | 281 | 212 |
| Titer @ 50% Viable [mg/L] | 2505 @ 76% | 3995 | 3033 |

TABLE 15

Fed batch process results

| Projected Outcome | Control (1000 L Process) Temp = 33° C. | Alternate Fed-Batch Experiment Temp = 33° C. | Daily Fed-Batch Experiment Temp = 33° C. |
|---|---|---|---|
| Harvests per Year (Allowing 3 day turnaround) | 21 | 20 | 20 |
| Yearly Product Yield (Based on 2600 L Harvest) [Kg/year] | 137 | 208 | 158 |

TABLE 15-continued

Fed batch process results

| Projected Outcome | Control (1000 L Process) Temp = 33° C. | Alternate Fed-Batch Experiment Temp = 33° C. | Daily Fed-Batch Experiment Temp = 33° C. |
|---|---|---|---|
| Increased Yearly Yield (control = 100%) | 100% | 152% | 115% |

Example 3

Stable Combination Feed Solutions for Increasing the Volumetric Productivity Of Fed-Batch Culture The following examples describe a novel approach to formulate stable high concentration feed solutions that include two hydrolyzates, at least one amino acid other than glutamine, a sugar, and a chemically defined medium base. The resulting feed solutions are capable of increasing the volumetric production of mammalian cell lines producing recombinant proteins. Finally, an accelerated method for fed-batch process development based on feedback control of the glucose concentration is proposed.

Materials and Methods

Combination feeds contained the hydrolyzates Bacto TC yeastolate, (RM-216) (BD Difco 255771) and phytone peptone, (BD Difco 2922450) plus glucose, L-asparagine monohydrate (Sigma-Aldrich) a reduced version of DMEM/F12 (NaCl, phosphate salts, pH indicators and other non-essential components were removed; Invitrogen 12500) or Ex-Cell PFCHO (A)-S1 (modified deficient) w/o glutamine, w/o NaHCO, (JRH Biosciences 67411-500L35470).

For the preparation of solutions, water was filtered using a Millipore Milli-Q PF with a PMQ004D2 filtration pack. Materials were dissolved in the specified mass of water using a bench top magnetic stirrer. After each component was added, complete dissolution was visually verified before the next component was incorporated.

When applicable, turbidity was quantified using a HACH 2100P portable turbidimeter (Hach Co. Loveland, Colo.). The human eye threshold for detecting turbidity is around 15 NTUs (Nephelometric Turbidity Units).

Bioreactor experiments were carried in 3 L Applikon bioreactors at an operating volume of 1.5 L with pH, temperature, agitation and oxygen control via cascading air and oxygen flow. Cell counting was done with a Cedex (Innovatis AG, Bielefeld, Germany). Glucose, lactate were determined using a YSI 2700 (YSI Inc., Yellow Springs, Ohio) and in some cases also additional metabolites with a Nova Bioprofile 400 (Nova Biomedical Corp., Waltham, Mass.). The equilibrium partial pressure of oxygen ($pO_2$), carbon dioxide ($pCO_2$), and pH was verified using an ABL 5 Blood Gas Analyzer (Radiometer A/S, Copenhagen, Brønshøj, Denmark).

Example 3.1

Preparation of Stable Combination Feeds Using PFCHO as Basal Medium

A single, high concentration feed facilitates cell culture fed-batch manufacturing, because it reduces the volume and the number of additions required. This is however, complicated due to the fact that PFCHO powder must be dissolved at pH values above 9.00. Furthermore, hydrolyzates are soluble under neutral pH conditions. Thus, trying to simply mix both components at neutral or high pH values will lead to (non dissolved) powder suspensions. As reported in the literature, "Fully optimized feeds often exist as two or more separate solutions that support more than one rate of introduction and feed pH (e.g., for reasons of solubility)" [1].

Combination Feed Stability Experiment

It was determined that the addition of hydrolysates allowed PFCHO concentrations to remain stable for longer periods, as described in the following table. The component amounts of 20 g Kg$^{-1}$ PFCHO, 7.5 g Kg$^{-1}$ asparagine, 21 g Kg$^{-1}$ glucose, 22 g Kg$^{-8-1}$ yeastolate, and 14 g Kg$^{-1}$ phytone were added in order to about 700 g of water and water was added at the end to achieve a final weight of 1 Kg. Solutions were mixed and then brought down to target pH with HCL 2.0 N. In the following table, turbidity was determined by visual observation with the naked eye.

TABLE 16

Effect of final pH on different combination feed formulations

| | Final solution pH | | | | |
|---|---|---|---|---|---|
| Formulation | 6.75 | 7.00 | 7.25 | 7.50 | 7.75 |
| 1 PFCHO, Asparagine and glucose dissolved at pH 10.0 | N/A | N/A | N/A | Completely precipitated before 4 hrs | |
| 2 Same as above (1) to pH 7.75, then add phytone and yeastolate | N/A | N/A | Final pH 7.3 | N/A | N/A |
| 3 Same as above (2), then pH to 6.75, 7.00, 7.25, 7.50, 7.75 | Slight degree of turbidity within 30-60 min; yet resulting solution remains stable | | | | |

As seen in Table 16, the least turbid were 2) and 3) pH 6.75 and 7.25. Note that both 2) and 3) did not become turbid even after almost 24 hrs. Based on these results, it was clear that the hydrolyzates stabilize PFCHO in solution, as low turbidity was achieved.

Given that the hydrolyzates stabilize the resulting mixture, phytone and yeastolate could be added to the PFCHO solution at pH 10.0; then the whole mixture be brought down to target pH. This order of addition would remove the unstable step of holding the PFCHO solution at pH values under 8.0, particularly vulnerable when mixing larger volumes.

To test the previous hypothesis we tested this new order of addition with a formulation containing 20 and 7.5 g·Kg$^{-1}$ of PFCHO and asparagine, respectively. The resulting solution, X-1, was divided and brought down to pH 7.0, 6.75, 6.5 and 6.25. These solutions proved stable, as can be observed in the following graph:

TABLE 17

Turbidity profiles (NTU) of formulation X-1 at different pH values

| | pH | | | |
|---|---|---|---|---|
| Time [hrs] | 6.25 | 6.50 | 6.75 | 7.00 |
| 2.25 | n/a | 8.44 | 9.86 | 11.32 |
| 4.00 | 8.77 | 7.8 | 9.25 | 10.70 |
| 6.00 | 7.02 | 5.71 | 6.28 | 4.25 |

After three hours, the least turbid solution was pH 6.50. The apparent decrease in turbidity, in particular for pH 7.0, was due to settling of some minute particles.

Glucose as a Stabilizer

A formulation (see Table 18) with 200 g Kg$^{-1}$ glucose added as a stabilizer was tested.

TABLE 18

Diluted D2E7 feed solution

| $_{MilliQ}H_2O$ | 750.0 | g · Kg$^{-1}$ | Water was in excess |
|---|---|---|---|
| Glucose | 200.0 | | As potential stabilizer |
| PFCHO | 20.0 | | |
| + NaOH 10N | | → | pH 10.00 |
| Asparagine | 2.29 | | |
| Yeastolate | 15.7 | | |
| Phytone | 10.0 | | |
| + HCl 5N | | → | pH 6.75-7.50 |

Components were weighted and added in order. Initial mass of water should be reduced to achieve 1 Kg final mass.

This solution proved to be stable for several hours for a range of pH values, as can be observed in the following table:

TABLE 19

Turbidity readings (NTU) of combination feed as a function of time and pH.

| | pH | | | |
|---|---|---|---|---|
| Time [hrs] | 6.72 | 7.00 | 7.22 | 7.50 |
| 0.25 | 3.48 | 3.75 | 3.95 | 5.83 |
| 2.50 | 3.07 | 3.13 | 3.42 | 3.74 |
| 8.50 | 2.98 | 2.95 | 2.99 | 3.15 |

The modified combination feed solutions comprising glucose were used to express two different antibodies, i.e., adalimumab (D2E7) and anti-IL-18 antibody ABT-325.

Combination Feed Solution for Stable D2E7 Production

If the volume of formulation added to the bioreactor is based on the lowest concentrated component (i.e. PFCHO), very large amounts of feed would need to be added to match what has been evaluated individually. Therefore, higher concentrations were the next step in developing an effective feeding formulation. This solution is referred to as the D2E7 combination feed solution and is described in the following table.

TABLE 20

D2E7 combination feed solution

| $_{MilliQ}H_2O$ | 750.0 | g · Kg$^{-1}$ |
|---|---|---|
| Glucose | 150.0 | |
| PFCHO | 27.0 | |
| +NaOH 10N | | → pH 10.00 |
| Asparagine | 3.1 | |
| Yeastolate | 21.2 | |
| Phytone | 13.5 | |
| +HCl 5N | | → pH 6.75 |

Components were weighted and added in order. Initial mass of water should be reduced to achieve 1 Kg final mass.

Formulations with 200, 150 and 100 g Kg$^{-1}$ glucose were tested. As can be seen in the following table, these solutions also had a stable turbidity for several hours. Table 21 shows that the addition of glucose reduced the turbidity of the solution.

TABLE 21

Turbidity time profiles for the D2E7 combination feed
solution as a function of glucose concentration.

| | Glucose [g/Kg combination feed] | | |
|---|---|---|---|
| Time [hrs] | 100 | 150 | 200 |
| 0 | n/a | 9.23 | 7.31 |
| 1 | 13.80 | 8.77 | n/a |
| 2 | 13.20 | 9.33 | n/a |
| 3 | 12.80 | 10.30 | n/a |
| 4 | 12.80 | 10.70 | 5.98 |
| 7 | n/a | n/a | 6.80 |

As shown in Table 21, increasing the glucose level decreased turbidity of the solution. These different formulations, based on their turbidity levels were regarded as acceptable for filtration experiments.

Combination Feed Solution for Stable ABT-325 Production

To obtain a stable ABT-325 combination feed, 50 L of the current formulation was prepared according to the method used for the D2E7 combination feed, as shown in Table 22.

TABLE 22

ABT-325 combination feed solution

| $_{MilliQ}H_2O$ | 750.0 | $g \cdot Kg^{-1}$ |
|---|---|---|
| Glucose | 150.0 | |
| PFCHO | 21.0 | |
| +NaOH 10N | → | pH 10.00 |
| Asparagine | 5.0 | |
| Yeastolate | 65.0 | |
| Phytone | 40.0 | |
| +HCl 5N | → | pH 6.75 |

Components were weighted and added in order. Initial mass of water should be reduced to achieve 1 Kg final mass.

Upon preparation, the solution maintained a turbidity level of approximately 20-30 NTUs, as can be observed in the following table:

TABLE 23

Turbidity of ABT-325 Combination feed

| Time [hrs[ | Turbidity [NTUs] |
|---|---|
| 0.00 | 41.8 |
| 1.00 | 28.7 |
| 1.50 | 19.8 |
| 2.00 | 20.0 |
| 3.50 | 14.5 |

50 L of an ABT-325 formulation combination feed solution was prepared according to the D2E7 method to test both the scalability and applicability of the preparation method. As shown above, the solution remained stable for four hours.

It should be noted that the PF CHO medium referred to in the above example corresponds to the modified PF CHO (modified Part A) referred to in the cell culture medium of Example 1.

Example 3.2

Preparation of Stable Combination Feeds Using DMEM-F12 as Basal Medium

As described in the previous example, it was possible to manufacture a stable combination feed solution with PFCHO and two hydrolyzates, as well as glucose. The following example demonstrates that this methodology may be applied to any basal feed formulation and leads to a stable combination feed solution.

DMEM-F12, a medium formulation that is publicly available, was modified to make it compatible with combination feed preparation, denominated here as DMEM-F12m. The following components were removed: NaCl, NaHCO$_3$, NaH$_2$PO$_4$.H$_2$O, Na$_2$HPO$_4$, D-Glucose, HEPES, Na-Hypoxanthine, Phenol red, L-glutamine and thymidine. Combinations feeds matching the D2E7 and ABT-325 feed formulations were prepared according to the methodology described in examples 3.0 and 3.1. The final components and formulation sequence is shown in the following table:

TABLE 24

DMEM-F12 combination feeds

| | Feed I | Feed II | |
|---|---|---|---|
| $_{MilliQ}H_2O$ | 600.0 | 600.0 | $g \cdot Kg^{-1}$ |
| Glucose | 150.0 | 150.0 | |
| DMEM-F12m | 27.0 | 21.0 | |
| +NaOH 10N | | → | pH 10.00 |
| Asparagine | 3.1 | 5.0 | |
| Yeastolate | 21.2 | 65.0 | |
| Phytone | 13.5 | 40.0 | |
| +HCl 5N | | → | pH 6.75 |
| $_{MilliQ}H_2O$ | To 1000 g | | |

Components were weighted and added in order to achieve 1 Kg final mass.

Once prepared, both feeds I and II maintained a turbidity of 12 NTUs or less for more than 4 hrs.

Example 3.3

Cell Growth and Productivity Enhancement Due to Combination Feed Addition

To evaluate the growth and titer promoting characteristics of the above combination feeds, ABT-874 cells (which express an anti IL-12 fully-human IgG1 antibody) were used. This CHO cell line is normally cultivated in cell culture medium SR-383 (2× with 500 nM mtx).

For these experiments, cells were passaged into DMEM/F12 for at least 5 generations until adaptation was observed by constant growth rate. Spinner cultures were stirred on a Thermolyne stir plate at 70 rpm in an incubator at 35° C. and 5% CO$_2$ Immediately before inoculation the required amount of cell suspension was taken from the maintenance culture. The cells were centrifuged, the supernatant was discarded and the pellets were resuspended in fresh, pre-warmed medium to obtain a seed density of 4×10$^5$/mL.

Cell culture was expanded in spinners until sufficient volume was generated for bioreactor inoculation to achieve a split ratio of 1:5 in 1.5 L Applikon bioreactors. Reactor running conditions were pH 6.9, 35° C., 150 rpm and a dissolved oxygen level of 40% of saturation. All bioreactor experiments were performed in duplicates. Cells were given three 1% of initial reactor volume bolus shots of combination feed every other day during the course of a run.

The use of both combination feeds greatly enhances cell culture growth. For the case of CF I, double the peak cell density was achieved, although the culture lasted only 10 days, as compared to 13 for the control. For the case of CF II, the peak cell density was almost tripled compared to the control and the culture lasted a similar time. In terms of final titer a more dramatic effect was observed. Titers for the DMEM/F12 medium were approximately 41 mg/L, vs 188 for CF 1 and 434 for CFII. The effect of different feed solutions on the maximum cell density, culture length, titer and specific productivity is summarized the following table:

TABLE 25

Performance of DMEM-F12m combination feeds

| Description | Peak Cell Density [10⁶ viable cells/mL] | Final IVC [×10⁶ cell·d/mL] | Culture Length [d] | Final Titer [mg/L] | qp [pg/cell-d] |
|---|---|---|---|---|---|
| Control (n = 2) | 1.07 +/− 0.018 | 9.53 +/− 0.005 | 13 | 41 +/− 1.9 | 4.7 +/− 0.29 |
| CFI (n = 2) | 1.92 +/− 0.031 | 11.27 +/− 0.004 | 10 | 188 +/− 0.1 | 16.4 +/− 12.03 |
| CFII (n = 2) | 2.72 +/− 0.009 | 20.74 +/− 0.177 | 13 | 434 +/− 16.5 | 25.1 +/− 1.17 |

Example 3.4

High-Titer Cell Culture Processes Via Addition of Combination Feed

Higher titers allow for fewer manufacturing runs to be needed to satisfy a given total yield. The following example describes a fed-batch large-scale process for ABT-874 which yielded an average titer of around 4 g/L during a fed-batch process. Additionally, further improvement of the media and combination feed allowed titer levels of over 6 g/L to be achieved.

Materials and Methods.

As a model system, the ABT-874 antibody product line was used.

Feed Solution Preparation

The feed solution was made according to the procedures previously described. Two asparagine concentrations were used, i.e., 5.0 or 7.5 g·Kg$^{-1}$. The method of preparation is shown in the following table:

TABLE 26

ABT-874 combo feed preparation

| | | | |
|---|---|---|---|
| 1 | $_{MilliQ}H_2O$ | 600.0 | g·Kg$^{-1}$ |
| 2 | Glucose | 150.0 | |
| 3 | PFCHO | 21.0 | |
| +4 | NaOH 10N | → | pH 10.00 |
| 5 | Asparagine | 5.0 or 7.5 | |
| 6 | Yeastolate | 65.0 | |
| 7 | Phytone | 40.0 | |
| +8 | HCl 5N | → | pH 6.75 |

Components were weighted and added in order to achieve 1 Kg final mass.

Materials were dissolved in the specified mass of water using a bench top magnetic stirrer under intense vortexing. Up to step 5, after each component was added, complete dissolution was visually verified before the next component was incorporated. However, this was not possible with steps 6 and 7. For these two steps, incorporation of the powder into the solution was considered sufficient to proceed to the final HCl addition.

Process Medium Screening

In order to obtain baseline performance data, an experiment featuring a 3× Fed-Batch (FB) 3000 L as a control, the prototype 4×FB process and non-fed (extended batch: EB) 3× and 4× conditions was run. In particular, it had been suggested that higher medium concentrations created an initial lag in the culture growth profile; however, no significant lag was observed for the extended batch (EB) 3× or 4× processes.

As expected, feed supplementation led to higher titers for both the 3× and 4× process. Nevertheless, significant growth suppression was observed for the 4× process if fed (i.e. fed-batch). Amino acid analysis of the small-scale experiments showed that, even after being fed, full depletion of the amino acids asparagine and glutamine still existed. For this reason, total feeding time and amount of asparagine in the combination feed were both increased. In conclusion, it was determined that the 4×FB process had potential to reach higher final titers than the EB processes or the 3×FB control. Therefore, it was chosen as a starting point for further development.

Differences between the 3× fed batch process (control) and the 4× fed batch process are described in Table 27 and described in further detail below.

Viable Cell Density at Feed Start

It was observed that initiating the feed at very low cell densities tended to suppress cell growth and eventually final titer. Thus, it was expected that an excessively delayed feed would cause loss of volumetric productivity due to cell starvation.

In order to investigate the above hypothesis, several experiments were carried out to determine the significance of feeding at different viable cell densities. The combined results of those experiments are plotted in the graph described in FIG. 1. As can be seen in FIG. 1, the titer at day 15 shows a strong dependence with the viable cell density at the day that feeding starts. A third-degree polynomial fitted to the data points shows that the maximum titer on day 15 can be expected at a feeding density of 3.5·10⁶ cells·ml$^{-1}$.

Reproducibility

20$^{-1}$ Process conditions for the 6 g·L process are described below in Table 27 and were defined as inoculation as a 1:4 split from a short fill run in SR-383, pH 7.0, DO=30%, 37° C. up to a cell density of 5.0·10⁶ viable cells/ml. Reactor running conditions were pH 6.9, T=35° C., DO=40%. Feeding was initiated when cells reached a viable density of 3.5·10⁶ cells/ml, lasting 10 days, via bolus additions of combination feed consisting of 1% of initial reactor weight each day.

Process conditions for the 4 g·L$^{-1}$ process are described below in Table 27.

TABLE 27

Highlights of 4 and 6 g·L−1 ABT-874 cell culture processes

| | Process | |
|---|---|---|
| Parameter | 3X FB | 4X FB |
| Medium | SR-286 (3XPFCHO) | SR-382 (4XPFCHO) |
| Split ratio | 1:5 | 1:4 |
| Seed density [10⁶ viable cells·ml$^{-1}$] | 0.5-1.0 | 1.0-1.25 |

TABLE 27-continued

Highlights of 4 and 6 g · L−1 ABT-874 cell culture processes

| Parameter | Process | |
|---|---|---|
| | 3X FB | 4X FB |
| Feed Start Criterion | Day 3 | $3.5 \cdot 10^6$ cells · ml$^{-1}$ |
| Feeding amount [%] | 1 | 1 |
| Feeding Length [days] | 7 | 10 |
| Asparagine in feed [g · l$^{-1}$] | 5.0 | 7.5 |
| Temperature shift | 33° C. @ $3.5 \cdot 10^6$ cells · ml$^-$ | none |
| Final Titer | 4 g · L$^{-1}$ | 6 g · L$^{-1}$ ± 0.24 (n = 9) |

Example 3.5

Fed-Batch Using Combination Feed Via Glucose Feedback Control

Feedback control allows targeting a set point for a given parameter with very limited understanding of the system intrinsic behavior. In this manner, a targeted set point can be maintained independently of any disturbances or alterations that the system might have undergone. Due to the complexity of mammalian cell culture metabolism, it is labor intensive to derive comprehensive models that could allow for prediction of a culture given trajectory. Nevertheless, it is desirable to develop a sampling method, e.g., by using an automated sampling, to be able to supply glucose in order to maintain a target glucose level. This allows decoupling of the effect of a given glucose concentration (or other metabolites) and also provides a means to study the effect that different ratios of glucose in the combination feed have on different cultures. The decoupling of the effect refers to the effect of maintaining a given glucose level, versus the effect of using a different amount of glucose in a combination feed.

Materials and Methods.

As model system, the product lines for two different anti-IL-12 antibodies, ABT-874 and 1D4.7 were used.

Automated sampling, i.e., YSI 2700 Bioprocess Analyzer, was chosen as the means for monitoring glucose levels in the cell culture medium. The online automated sampling device was established by attaching a YSI 2730 Monitor and Control Accessory to a YSI 2700 Bioprocess Analyzer (see YSI Life Sciences; Yellow Springs, Ohio). This sampling device consisted of a pump that held two tubes. The first tube had two branches, one that collected the sample from the bioreactor, and a second one that pumped antiseptic to maintain sterility. Once the sample was taken, it was pumped into an external chamber, from which the sipper took the sample for the actual analysis. The second tube through the pump was used to collect the discharge into a waste container. Several parameters of the online sampling accessory were controlled, such as sampling interval and TPU (Time per Unit Error, which corresponds to the time the fee pump runs based on the measured offset from a set point).

The pump was connected to the YSI using a 15-pin connector. The pin corresponding to the glucose probe (White-7, Black-11) in the YSI was connected to the TTL on/off pin (8) in the pump, and one of the ground pins from the YSI (1-5) was connected to the chassis of the 15-pin connector for the pump. The connection was tested by turning the pump on and off from the YSI Setup Menu. The pump tubing used was Masterflex CFLEX 082.

TABLE 28

Feedback initial experiment setup

| Cells | ABT-874 |
|---|---|
| Media | 3XPFCHO (SR-286) |
| Glucose Feed | 400 g/L |
| YSI TPU | 16 |
| Reactor Volume Tested | 1.5 L |
| YSI Purge Time | 60 sec |
| Pump Speed | 50 (half, ~16 RPM) |
| YSI Sampling Interval | 4 hrs/2 hrs (explained below) |
| YSI Output Signal | X2 (for YSI1-A25) |
| Antiseptic | 0.1N NaOH |

YSI1-A25 reactor was controlled at 4.9 g/L of glucose. The glucose control at 4.9 g/L started at about day 2 using a sampling interval of 4 hours until day 8. At day 8, the sampling interval was reduced to 2 hours, and the set point in the YSI automated device was reset to erase the PID memory. The fluctuations due to overshoot from the set-point were significantly reduced after day 8. Hence, it was established that a sampling interval of 2 hours was optimal for these conditions. The average overshoot from day 2 to 8 was 0.43 g/L and the average undershoot was 0.31 g/L, with a fluctuation error of about 8% from the set point. On the other hand, the average overshoot from day 8 to 13 was 0.08 g/L and the average undershoot was 0.09 g/L, with a fluctuation error of about 2%.

Control of Glucose Concentration Using Combination Feed

The schedule for feeding combination feed solutions to a culture in a bioreactor was defined via an empirical approach. Different feeding amounts were tested, as were different feeding times until a viable fed-batch scheme was found. Ideally, the feeding schedule of a combination feed should meet the specific requirements of a given culture.

In view of the above considerations, it was advantageous to provide the combination feed based on the cell culture needs, for example, by using glucose as an indicator of nutritional requirements. In this manner, a feedback control system may be used to 1) Test different feeds with varying glucose concentrations and 2) Use the generated feeding profile to manually feed at the larger scale culture.

The following table summarizes two different reactor operation modes using a cell line that produces the 1D4.7 mAb. The reference experiment (referred to as baseline in Table 29) illustrates typical titer performance for an extended batch process in SR-372 medium, running at pH 6.9, T=35° C., DO=40% in 1.5 L Applikon bioreactors. YSI experiments were run under the same conditions plus feedback control to supply combination feeds containing 100, 150 or 200 g·L$^{-1}$ of glucose.

TABLE 29

Performance of feedback control using combination feed

| Experiment | final Titer [mg/L] |
|---|---|
| Baseline (n = 2) | 1312+/−33 |
| YSI 100 (n = 1) | 1974 |
| YSI 150 (n = 2) | 2044+/−164 |
| YSI 200 (n = 2) | 1837+/−163 |

As it can be seen from Table 29, the feedback system using a variety of combination feeds greatly improved final titer of the antibody.

Feeding profiles from experiments like the previous one were obtained by weighing the amount of combination feed supplied per day. A typical feeding profile is presented in the following table:

TABLE 30

Typical feed profile generated via feedback control
(profile for 1D4.7 antibody)

| Day | Feed [%] |
|---|---|
| 1 | 0.00 |
| 2 | 0.00 |
| 3 | 0.00 |
| 4 | 0.00 |
| 5 | 1.12 |
| 6 | 1.56 |
| 7 | 1.79 |
| 8 | 1.23 |
| 9 | 0.89 |
| 10 | 0.75 |
| 11 | 0.46 |
| 12 | 0.32 |

The above scheme can also be done to manually to feed a reactor even without a feedback control system. In this manner, the feeding schedule can be up scaled.

Summary of Results.

Fed-batch processes utilizing both a mixture of hydrolyzates and a chemically defined basal medium were shown to increase the final titer of secreted mAb in mammalian cell culture.

Furthermore, a method capable of generating the following stable combination feeds was demonstrated:

TABLE 31

Stable combination feeds

| | X-1 | D2E7 diluted | D2E7 | ABT-325, ABT-874 | Feed I | Feed II | |
|---|---|---|---|---|---|---|---|
| Glucose | 21 | 200 | 100, 150, 250 | 150 | 150 | 150 | $g \cdot Kg^{-1}$ |
| PFCHO (p), DMEM-F12m (d), +NaOH 10N | 20 (p) | 20 (p) | 27 (p) | 21 (d) | 27 (d) | 21 (d) | → pH 10.00 |
| Asparagine | 7.5 | 2.29 | 3.1 | 5, 7.5 | 3.1 | 5 | |
| Yeastolate | 22 | 15.7 | 21.2 | 65.0 | 21.2 | 65.0 | |
| Phytone +HCl 5N | 14 | 10.0 | 13.5 | 40.0 | 13.5 | 40.0 | → pH 6.75 |
| $_{MilliQ}H_2O$ | | | | To 1000 g | | | |

The combination feed described in Table 31 was made starting with $_{MilliQ}H_2O$ (up to 750 g). As indicated above, ingredients were added to the water to a final weight (overall weight of combination feed) of 1000 g. Additionally, combination feed solutions were shown to increase cell culture longevity, peak viable cell density, and specific productivity. Cell culture fed-batch processes using combination feeds capable of reaching titer levels up to 6 g·L$^{-1}$ of secreted monoclonal antibody were demonstrated. The above combination feeds were also shown to increase the cell density of the cell cultures.

Finally, a method employing a feedback control system and different combination feeds was also shown to be capable of increasing titer levels. This approach could be used to accelerate cell culture process development by quickly generating feeding schedules.

REFERENCES

1. Whitford, W. G., *Fed-Batch Mammalian Cell Culture in Bioproduction*. BioProcess International, 2006.30-40.
2. YSI Incorporated. (1998) YSI 2700 Select Biochemistry Analyzer User's Manual.
3, YSI Incorporated. (1998) YSI 2730 Monitor and Control Accessory User's Manual.
4. Watson Marlow Pumps. 101F, 101U User's Manual.

Example 4

Application of Sodium Butyrate and
N-Acetylcysteine to Increase the Productivity of an
Anti IL-18-Producing CHO Cell Line The present invention encompasses a novel approach to increase the productivity of an antibody, e.g., an anti IL-18-producing CHO cell line. More specifically, the following example relates to a final antibody, e.g., anti IL-18, titer increase via addition of chemicals to the cell culture medium. Improvements in cell viability and antibody titer are described below using an exemplary antibody, i.e., IL-18 antibody.

Cell Line and Culture Media

The anti IL-18 antibody used in the following example is a fully human IgG1 antibody (Ab) to IL-18. The CHO cell line expressing anti IL-18 is cultivated in a growth medium, described above in Table 4 of Example 1, SR-371. The production media for the cell line are as also described above in Example 1, SR-372 (used for culture in spinner flasks) and SR-382 (used for culture in bioreactors).

Culture Conditions for Experiments Carried Out in Spinner Flasks

All spinner flask experiments were performed in duplicates. The spinner cultures were stirred on a Thermolyne stir plate at 80 rpm in an incubator at 35° C. and 5% $CO_2$. Immediately before inoculation the required amount of cell suspension was taken from the maintenance culture. The cells were centrifuged, the supernatant was discarded and the pellets were resuspended in fresh, pre-warmed culture medium to obtain a seed density of $4 \times 10^5$/mL.

Example 4.1

Effect of Sodium Butyrate on Growth and Productivity of an Anti IL-18-Producing CHO Cell Line Cultivated in Growth Medium To determine the concentration range of sodium butyrate, the first experiment was carried out in SR-371 containing various concentrations of sodium butyrate. The experiment was carried out in 100 mL spinner flasks with 70 mL working volume. Sodium butyrate was added from a 1 M stock solution that was prepared by dissolving 1.101 g sodium butyrate in 10 mL MilliQ water and sterilized by filtration through a 0.2 µm filter. The solution was stored at −20° C.

Sodium Butyrate was added in the beginning of the culture (Day 0) in concentrations of 0 mM, 0.125 mM, 0.5 mM and 1 mM. Cell density and viability were determined with an automatic cell counter (Cedex, Innovatis, Germany) in this example and all following examples. Table 32 shows the viable cell density over culture time, and Table 33 describes the viability over culture time. The experiment was carried out for 12 days.

TABLE 32

Viable Cell Density over Culture Time
Viable Cell Density [$10^5$/ml]

| Day | Flask 1: 0 mM Butyrate | Flask 2: 0 mM Butyrate | Flask 3: 0.125 mM Butyrate | Flask 4: 0.125 mM Butyrate | Flask 5: 0.5 mM Butyrate | Flask 6: 0.5 mM Butyrate | Flask 7: 1 mM Butyrate | Flask 8: 1 mM Butyrate |
|---|---|---|---|---|---|---|---|---|
| 0 | 3.2 | 3.85 | 4.46 | 3.01 | 3.66 | 3.98 | 3.83 | 4.07 |
| 3 | 36.38 | 33.18 | 27.12 | 29.96 | 16.97 | 11.71 | 7.68 | 5.74 |
| 5 | 84.48 | 70.37 | 62.56 | 66.1 | 21.79 | 9.77 | 3.25 | 2.35 |
| 7 | 65.98 | 64.19 | 59.15 | 68.65 | 17.72 | 5.41 | 1.04 | 0.7 |
| 10 | 7.83 | 11.17 | 8.63 | 11.85 | 4.53 | 6.93 | 0.8 | 0.61 |
| 12 | 1.36 | 2.28 | 3.68 | 3.81 | 2.08 | 1.89 | 0.22 | 0.41 |

TABLE 33

Viability over Culture Time
Viability [%]

| Day | Flask 1: 0 mM Butyrate | Flask 2: 0 mM Butyrate | Flask 3: 0.125 mM Butyrate | Flask 4: 0.125 mM Butyrate | Flask 5: 0.5 mM Butyrate | Flask 6: 0.5 mM Butyrate | Flask 7: 1 mM Butyrate | Flask 8: 1 mM Butyrate |
|---|---|---|---|---|---|---|---|---|
| 0 | 98.5 | 97.5 | 98.9 | 100 | 97.4 | 98.2 | 98.8 | 98.8 |
| 3 | 98.3 | 98.1 | 97.3 | 97.9 | 95.4 | 92.2 | 88.3 | 73.8 |
| 5 | 96.7 | 96.7 | 96 | 96.7 | 88.8 | 72.9 | 54 | 40.1 |
| 7 | 73.4 | 75.5 | 78.1 | 83.3 | 69 | 43.1 | 24.2 | 16.4 |
| 10 | 7.9 | 13.1 | 13.1 | 14.3 | 21 | 25.9 | 11.3 | 14.5 |
| 12 | 1.4 | 2.8 | 5.9 | 4.9 | 7.6 | 14.9 | 3.2 | 8.9 |

It can be clearly seen that sodium butyrate affected cell growth and viability. While there was no obvious effect on cell growth and viability at a butyrate concentration of 0.125 mM, there was a clear impact on cell growth at 0.5 mM butyrate leading to a lower maximum cell density. At 0.5 mM sodium butyrate affected viability after 5 days of culture time. Sodium butyrate inhibited cell growth completely at a concentration of 1 mM, and the viability decreased continuously from Day 0 on.

Table 34 shows the anti IL-18 titer over culture time. The concentration of anti IL-18 was determined by a Poros A HPLC assay in this example and all following examples.

TABLE 34

Anti IL-18 titer over culture time
Titer [mg/L]

| Day | Flask 1: 0 mM Butyrate | Flask 2: 0 mM Butyrate | Flask 3: 0.125 mM Butyrate | Flask 4: 0.125 mM Butyrate | Flask 5: 0.5 mM Butyrate | Flask 6: 0.5 mM Butyrate | Flask 7: 1 mM Butyrate | Flask 8: 1 mM Butyrate |
|---|---|---|---|---|---|---|---|---|
| 0 | 5.4 | 2.4 | 1.8 | 1.6 | 1.3 | 1.3 | 1.1 | 1.3 |
| 3 | 68.9 | 58.1 | 67.7 | 65.7 | 52.1 | 41.9 | 36.3 | 26.2 |
| 5 | 173.2 | 150.4 | 169.4 | 174.3 | 132.6 | 84.2 | 68.6 | 46.4 |
| 7 | 235.5 | 211.9 | 253.6 | 278.5 | 217.7 | 110.7 | 85 | 60.9 |
| 10 | 265.5 | 241.8 | 304.3 | 365.9 | 278.2 | 163.3 | 91.8 | 70.3 |
| 12 | 269.7 | 244.4 | 318.7 | 385.8 | 282.7 | 175.9 | 94 | 75.4 |

The average final titer of the cultures with 0.125 mM butyrate was 352 mg/L, the average final titer of the untreated control 257 mg/L. At this concentration butyrate treatment led to a 40% increase in final titer.

Example 4.2

Effect of Sodium Butyrate on Growth and Productivity of an Anti IL-18-Producing CHO Cell Line Cultivated in SR-372

The anti IL-18-expressing CHO cell line was adapted to growth in SR-372 in order to exclude any possible effect of the culture split from SR-371 to SR-372. All experiments with cells adapted to growth in SR-372 were carried out in 250 mL spinner flasks with 180 mL working volume. The cultures were carried out applying the conditions outlined above in the section entitled "Culture Conditions for Experiments Carried out in Spinner Flasks."

An experiment was designed to add butyrate when the cells were in the mid and late exponential growth phase. The later addition of butyrate will likely cause less stress to the cells and result in improved cell growth and higher IVC compared to addition on Day 0 because the butyrate concentration per cell is lower (IVC (Integral of Viable Cells) is defined as the integral of the viable cell density versus culture time). Butyrate was added on Day 4 and Day 5 in concentrations of 0.5 mM and 2 mM. The experiment was carried out for 12 days. Table 35 shows the viable cell density over culture time, Table 36 the viability over culture time. Only 2 mM sodium butyrate added on Day 4 resulted in reduced viability compared to the control, the other conditions did not affect viability.

TABLE 35

Viable cell density over culture time
Viable Cell Density [$10^5$/mL]

| Day | Flask 1: 0 mM Butyrate | Flask 2: 0 mM Butyrate | Flask 3: 0.5 mM Butyrate @ Day 4 | Flask 4: 0.5 mM Butyrate @ Day 4 | Flask 5: 2 mM Butyrate @ Day 4 | Flask 6: 2 mM Butyrate @ Day 4 | Flask 7: 0.5 mM Butyrate @ Day 5 | Flask 8: 0.5 mM Butyrate @ Day 5 | Flask 9: 2 mM Butyrate @ Day 5 | Flask 10: 2 mM Butyrate @ Day 5 |
|---|---|---|---|---|---|---|---|---|---|---|
| 0 | 2.35 | 3.37 | 3.08 | 2.61 | 2.27 | 2.41 | 3.2 | 2.27 | 2.49 | 2.2 |
| 3 | 14.51 | 15.79 | 12.79 | 13.69 | 14.04 | 9.42 | 11.41 | 11.36 | 10.42 | 10.93 |
| 4 | 28.88 | 20.91 | 18.88 | 26.11 | 25.48 | 16.09 | 18.78 | 23.16 | 16.57 | 22.16 |
| 5 | 28.58 | 32.17 | 36.01 | 33.03 | 27.82 | 21.98 | 30.76 | 35.8 | 28.38 | 30.71 |
| 6 | 61.91 | 54.31 | 45.2 | 43.08 | 37.02 | 34.28 | 47.82 | 55.66 | 48.28 | 49.27 |
| 7 | 56.23 | 51.59 | 40.09 | 36.19 | 33.34 | 27.21 | 42.97 | 52.08 | 41.45 | 48.75 |
| 10 | 43.06 | 51.89 | 29.2 | 23.33 | 14.07 | 13.05 | 29.58 | 28.61 | 25.07 | 26.62 |
| 12 | 24.8 | 33.38 | 19.38 | 14.32 | 9.66 | 8.22 | 18.25 | 16.18 | 16.01 | 18.93 |

TABLE 36

Viability over culture time
Viability [%]

| Day | Flask 1: 0 mM Butyrate | Flask 2: 0 mM Butyrate | Flask 3: 0.5 mM Butyrate @ Day 4 | Flask 4: 0.5 mM Butyrate @ Day 4 | Flask 5: 2 mM Butyrate @ Day 4 | Flask 6: 2 mM Butyrate @ Day 4 | Flask 7: 0.5 mM Butyrate @ Day 5 | Flask 8: 0.5 mM Butyrate @ Day 5 | Flask 9: 2 mM Butyrate @ Day 5 | Flask 10: 2 mM Butyrate @ Day 5 |
|---|---|---|---|---|---|---|---|---|---|---|
| 0 | 98.4 | 94.6 | 92.7 | 99 | 95.2 | 94.9 | 98.8 | 97.7 | 96.5 | 98.9 |
| 3 | 96.6 | 97.2 | 98.8 | 99 | 97.2 | 98 | 97.8 | 97.8 | 96.8 | 97.8 |
| 4 | 97 | 98.5 | 99 | 98.6 | 98.5 | 98 | 98.9 | 97.8 | 98.7 | 98.2 |
| 5 | 96.6 | 97.7 | 97.5 | 97.3 | 96.6 | 97.9 | 98 | 97.2 | 98.1 | 98.3 |
| 6 | 96.5 | 96.4 | 96.2 | 96 | 93.6 | 92.4 | 96.3 | 96 | 95.9 | 95.8 |
| 7 | 95.6 | 95.7 | 93.8 | 92.9 | 87.8 | 87.5 | 94.2 | 94 | 92.6 | 91.8 |
| 10 | 62.6 | 69.4 | 61.9 | 53.9 | 40.8 | 39.2 | 63.7 | 56.9 | 57.7 | 57.1 |
| 12 | 38.3 | 46.2 | 40.4 | 33.6 | 24.5 | 25.2 | 36.7 | 32.7 | 34.1 | 34.4 |

Table 37 reveals the anti IL-18 titer over culture time. 2 mM sodium butyrate added on Day 5 resulted in an increase of 29% compared to the control (317 mg/L versus 245 mg/L, respectively). Cell growth was not significantly inhibited under these conditions (see Table 35).

TABLE 37

Anti IL-18 titer over culture time
Titer [mg/L]

| Day | Flask 1: 0 mM Butyrate | Flask 2: 0 mM Butyrate | Flask 3: 0.5 mM Butyrate @ Day 4 | Flask 4: 0.5 mM Butyrate @ Day 4 | Flask 5: 2 mM Butyrate @ Day 4 | Flask 6: 2 mM Butyrate @ Day 4 | Flask 7: 0.5 mM Butyrate @ Day 5 | Flask 8: 0.5 mM Butyrate @ Day 5 | Flask 9: 2 mM Butyrate @ Day 5 | Flask 10: 2 mM Butyrate @ Day 5 |
|---|---|---|---|---|---|---|---|---|---|---|
| 7 | 138.5 | 141.1 | 147.7 | 139.2 | 183.4 | 182 | 129.5 | 137.5 | 152.8 | 149.5 |
| 10 | 192.2 | 208.7 | 226.9 | 203.3 | 269.6 | 259.5 | 202.5 | 205.4 | 266.1 | 260.6 |
| 12 | 232.2 | 258.7 | 269.4 | 235.3 | 307.8 | 286.2 | 237.4 | 236.9 | 319.3 | 315 |

Example 4.3

Effect of Sodium Butyrate on Growth and Productivity of an Anti IL-18-Producing CHO Cell Line Cultivated in SR-382 in a 3 L Bioreactor The following example demonstrates an increase in final anti IL-18 titer by application of sodium butyrate to the anti IL-18 Process B (see Section 1.5) in a large scale, i.e., 3 L bioreactors. This process was developed in 3 L Applikon bioreactors. The seed train was carried out in SR-371 until the short-fill stage (SR-372). The short-fill stage was simulated in a 20 L Biowave Bag with 10 L working volume. The experiment investigating the effect of sodium butyrate on growth and productivity of the anti IL-18 Process B was carried out in 3 L Applikon bioreactors with 1.5 L working volume. Each bioreactor was filled with 1125 mL SR-382 and inoculated by adding 375 mL of cell suspension from the Biowave Bag containing anti IL-18 cells in SR-372.

In example 4.2 the titer increase was achieved by adding butyrate when the cells were in the mid- to late log phase, which was day 5 in spinner flasks. Historically, the mid- to late log phase of the anti IL-18 production process in a 3 L bioreactor is on day 7 of culture time. In this example, day 7 was chosen for addition of sodium butyrate to the culture to ensure that butyrate is added in the mid- to late log phase.

A sodium butyrate stock solution at a concentration of 200 mM was prepared on day 7 immediately before addition to the culture by dissolving 4.404 g sodium butyrate in 200 mL MilliQ water. This solution was sterilized by filtration through a 0.22 μm filter.

The experiment was carried out with 5 bioreactors. Each bioreactor run was terminated when the respective viability was lower than 50%. Two bioreactors served as the control (anti IL-18 Process B). Sodium butyrate was added on day 7 of culture time to the other 3 bioreactors in concentrations of 0.3 mM, 1 mM and 3 mM, respectively. Table 38 shows the viable cell concentration over culture time, and Table 39 shows the viability over culture time.

TABLE 38

Viable cell density over culture time
Viable Cell Density [10$^5$/ml]

| Day | Reactor 1: 1 mM Butyrate | Reactor 2: No Butyrate | Reactor 3: 0.3 mM Butyrate | Reactor 4: 3 mM Butyrate | Reactor 5: No Butyrate |
|---|---|---|---|---|---|
| 0 | 5.53 | 5.22 | 4.89 | 5.28 | 5.41 |
| 1 | 8.21 | 7.68 | 7.66 | 9.66 | 6.81 |
| 2 | 11.35 | 13.53 | 10.39 | 11.12 | 10.07 |
| 3 | 15.62 | 17.37 | 12.58 | 14.3 | 13.07 |
| 4 | 20.69 | 22.4 | 18.39 | 22.46 | 16.49 |
| 5 | 29.58 | 31.55 | 31.15 | 34.03 | 23.43 |
| 6 | 41.27 | 44.42 | 43.32 | 46.81 | 32.3 |
| 7 | 59.07 | 62.09 | 56.91 | 60.46 | 33.95 |
| 8 | 67.07 | 76.26 | 51.82 | 76.4 | 45.43 |
| 9 | 68.68 | 73.23 | 63.11 | 61.52 | 57.6 |
| 10 | 65.55 | 70.17 | 64.53 | 55.52 | 62.45 |
| 11 | 66.55 | 72.98 | 66.23 | 47.27 | 63.42 |
| 12 | 60.98 | 56.33 | 45.87 | 30.99 | 44.65 |
| 13 | 49.67 | 52.03 | 40.39 | 21.34 | 39.1 |
| 14 | 38.46 | 30.51 | 21.93 | | 18.38 |
| 15 | 33.23 | 38.37 | 41.34 | | 35.97 |
| 16 | 27.97 | 29.31 | 33.89 | | 24.58 |
| 17 | | | 30.13 | | 17.51 |
| 18 | | | 20.98 | | |

TABLE 39

Viability over culture time
Viability [%]

| Day | Reactor 1: 1 mM Butyrate | Reactor 2: No Butyrate | Reactor 3: 0.3 mM Butyrate | Reactor 4: 3 mM Butyrate | Reactor 5: No Butyrate |
|---|---|---|---|---|---|
| 0 | 95.3 | 96 | 92.9 | 94.3 | 96.4 |
| 1 | 96.4 | 95.4 | 96.4 | 96.3 | 95.9 |
| 2 | 96.3 | 95.9 | 95.9 | 96.1 | 96.7 |
| 3 | 96.6 | 95.6 | 97.7 | 96.6 | 95.3 |
| 4 | 97.3 | 97.2 | 96.4 | 95.8 | 95.2 |
| 5 | 97.1 | 96.4 | 96.2 | 96.4 | 95.3 |
| 6 | 96.4 | 96.5 | 96.2 | 96.8 | 95.9 |
| 7 | 96.3 | 95.2 | 95.8 | 94.3 | 95.1 |
| 8 | 96.2 | 95.2 | 94.2 | 95.1 | 94.8 |
| 9 | 95.6 | 95.2 | 95.4 | 93.6 | 94.2 |
| 10 | 94.3 | 94.5 | 94.6 | 87.4 | 93.4 |
| 11 | 92.2 | 93.9 | 93.8 | 78.9 | 93 |
| 12 | 88.1 | 91.7 | 92.4 | 51.9 | 92 |
| 13 | 80.6 | 86.9 | 90.2 | 33.7 | 89.2 |
| 14 | 66.7 | 76.2 | 88.9 | | 84.1 |
| 15 | 57 | 60.7 | 85.2 | | 73.4 |
| 16 | 45.9 | 42.7 | 69.5 | | 50.7 |
| 17 | | | 58.1 | | 34.2 |
| 18 | | | 41 | | |

The control culture grew slower in reactor 5 than in the replicate (reactor 2) due to high initial $CO_2$ concentrations in reactor 5. Reactor 2 was terminated on day 16 of culture time (historically observed in the anti IL-18 production process), reactor 5 was terminated on day 17. Sodium butyrate at a concentration of 3 mM (reactor 4) affected cell growth and viability. Two days after butyrate addition cells started to die. Butyrate at 1 mM did not affect cell growth and viability (reactor 1), the reactor run was terminated on day 16. Cell growth was very similar compared to the control in reactor 2. Butyrate at 0.3 mM prolonged the culture time for 2 days (reactor 3). Table 40 shows the anti IL-18 titer over culture time.

TABLE 40

Anti IL-18 titer over culture time
Titer [mg/L]

| Day | Reactor 1: 1 mM Butyrate | Reactor 2: No Butyrate | Reactor 3: 0.3 mM Butyrate | Reactor 4: 3 mM Butyrate | Reactor 5: No Butyrate |
|---|---|---|---|---|---|
| 9 | 1033 | 1074.2 | 905.8 | 966.9 | 747.4 |
| 10 | 1218.4 | 1223.9 | 1096.4 | 1184.9 | 877.5 |
| 11 | 1410.4 | 1460 | 1261.1 | 1242.9 | 1053.5 |
| 12 | 1663.5 | 1538.1 | 1485.1 | 1269.5 | 1216.7 |
| 13 | 1700.2 | 1912.5 | 1750.9 | 1304.6 | 1303 |
| 14 | 1852.7 | 2136.9 | 1923.4 | | 1429.3 |
| 15 | 1909.4 | 2223.2 | 2280.4 | | 1672.3 |
| 16 | 1933.7 | 2324.7 | 2108.6 | | 1540.5 |
| 17 | | | 2561.3 | | 1589.4 |
| 18 | | | 2448.6 | | |

The final titer (day 16) of the culture in reactor 2 (representing anti IL-18 Process B) was 2325 g/L. The final titer in reactor 5 was 1589 g/L. This lower titer is likely due to the worse cell growth caused by the high initial $CO_2$ concentration in the culture medium. Butyrate at 1 mM and 3 mM added on day 7 resulted in lower final titer than the control (reactor 2). Butyrate at 0.3 mM added on day 7 resulted in a titer of 2561 g/L on day 17 which is an increase of 10% compared to the control. This titer was the highest titer achieved in the anti IL-18 process.

Example 4.4

Effect of N-Acetylcysteine (10 mM, 20 mM, 40 mM, 80 mM) on Growth and Productivity of an Anti-IL-18-Producing CHO Cell Line Cultivated in SR-372

N-Acetylcysteine can protect mammalian cells from cell death. As an antioxidant it can directly reduce reactive oxygen species. By deacetylation it can be converted to cysteine and increase intracellular glutathione levels. Glutathione can scavenge reactive oxygen species and serves as a substrate in the reduction of hydrogen peroxide to water.

This example demonstrates the anti IL-18 titer-increasing effect of N-acetylcysteine. The experiments were carried out in 250 mL spinner flasks with 180 mL working volume. The culture medium was SR-372. Before the experiment cells were pre-adapted to growth in SR-372 as described in example 4.2. The spinner culture conditions were applied as described above in "Culture Conditions for Experiments Carried out in Spinner Flasks."

An N-acetylcysteine stock solution of 1 M was prepared by dissolving 16.32 g N-acetylcysteine in 100 mL MilliQ water on a heated stir plate. The stock solution was sterilized by filtration through a 0.22 µm filter. One day prior to start of the experiment N-acetylcysteine was added to SR-372 to obtain concentrations of 0 mM, 10 mM, 20 mM, 40 mM and 80 mM. The experiment was started by centrifugation of cells from the CHO anti IL-18 maintenance culture as described above in "Culture Conditions for Experiments Carried out in Spinner Flasks." Each spinner culture was terminated when the respective viability was lower than 50%.

Cell growth was not possible in N-acetylcysteine concentrations of 20 mM, 40 mM and 80 mM. Table 41 and Table 42 show the comparison of viable cell density and viability, respectively, over culture time with cells grown in 0 mM N-acetylcysteine and 10 mM N-acetylcysteine.

TABLE 41

Viable cell density over culture time
Viable Cell Density [$10^5$/mL]

| Day | Flask 1: No N-acetylcysteine | Flask 2: No N-acetylcysteine | Flask 3: 10 mM N-acetylcysteine | Flask 4: 10 mM N-acetylcysteine |
|---|---|---|---|---|
| 0 | 3.60 | 3.44 | 2.73 | 2.73 |
| 3 | 18.34 | 17.72 | 3.58 | 3.02 |
| 4 | 29.39 | 29.71 | 4.47 | 4.24 |
| 5 | 33.54 | 31.05 | 6.46 | 6.40 |
| 6 | 37.38 | 32.92 | 9.84 | 7.27 |
| 7 | 34.26 | 31.00 | 12.36 | 12.00 |
| 8 | 17.49 | 17.68 | 24.20 | 22.42 |
| 9 | 25.34 | 21.54 | 20.14 | 19.48 |
| 10 | 17.49 | 17.68 | 24.20 | 22.42 |
| 11 | 10.75 | 13.84 | 25.02 | 26.00 |
| 12 | | | 27.44 | 27.56 |
| 13 | | | 25.77 | 27.86 |
| 14 | | | 22.77 | 24.17 |
| 15 | | | 18.40 | 19.22 |
| 16 | | | 14.60 | 16.30 |

TABLE 42

Viability over culture time
Viability [%]

| Day | Flask 1: No N-acetylcysteine | Flask 2: No N-acetylcysteine | Flask 3: 10 mM N-acetylcysteine | Flask 4: 10 mM N-acetylcysteine |
|---|---|---|---|---|
| 0 | 97.4 | 96.9 | 96.2 | 95.3 |
| 3 | 98.8 | 98.6 | 57.2 | 52.1 |
| 4 | 99.0 | 98.8 | 61.9 | 62.2 |
| 5 | 98.7 | 98.5 | 69.5 | 72.1 |
| 6 | 95.4 | 92.8 | 76.0 | 73.5 |
| 7 | 87.8 | 84.0 | 81.5 | 80.9 |
| 8 | 73.3 | 69.6 | 85.5 | 82.7 |
| 9 | 64.9 | 60.8 | 82.7 | 86.5 |
| 10 | 52.5 | 49.0 | 82.5 | 86.9 |
| 11 | 38.6 | 38.1 | 81.7 | 87.2 |
| 12 | | | 79.2 | 83.1 |
| 13 | | | 74.8 | 78.9 |
| 14 | | | 67.2 | 68.7 |
| 15 | | | 56.7 | 56.9 |
| 16 | | | 49.3 | 47.2 |

The control culture (no N-acetylcysteine) was terminated on day 11 of culture time whereas the culture with 10 mM N-acetylcysteine could be prolonged until day 16. Initially, 10 mM N-acetylcysteine affected cell growth and viability and lead to a decrease in viability until day 3. Then the viability started to increase. The maximum cell density of cultures grown in 10 mM N-acetylcysteine was lower compared to the control. Table 43 demonstrates the increase in final anti IL-18 titer by N-acetylcysteine.

TABLE 43

Anti IL-18 titer over culture time
Titer [mg/L]

| Day | Flask 1: No N-acetylcysteine | Flask 2: No N-acetylcysteine | Flask 3: 10 mM N-acetylcysteine | Flask 4: 10 mM N-acetylcysteine |
|---|---|---|---|---|
| 4 | 102.0 | 94.9 | 23.9 | 21.9 |
| 5 | 130.5 | 122.4 | 35.3 | 32.5 |
| 6 | 168.5 | 154.3 | 60.6 | 55.9 |
| 7 | 190.4 | 171.8 | 84.2 | 78.0 |
| 8 | 216.4 | 194.3 | 125.3 | 119.3 |
| 9 | 233.0 | 206.9 | 156.6 | 153.1 |
| 10 | 243.2 | 216.4 | 185.9 | 187.7 |
| 11 | 258.6 | 227.8 | 224.1 | 230.9 |
| 12 | | | 264.1 | 272.6 |
| 13 | | | 300.2 | 311.2 |
| 14 | | | 334.0 | 314.6 |
| 15 | | | 393.0 | 384.4 |
| 16 | | | 414.6 | 421.4 |

The average final titer of the control cultures is 243.2 mg/L, the average final titer of the cultures grown in 10 mM N-acetylcysteine was 418 mg/L. This was an increase of 72% compared to the control.

Example 4.5

Effect of N-Acetylcysteine (1 mM, 2 mM, 4 mM, 8 mM) on Growth and Productivity of an Anti-IL-18-Producing CHO Cell Line Cultivated in SR-372

As described in example 4.4, N-acetylcysteine at a concentration of 10 mM added on day 0 could prolong the culture time and lead to an increase in final titer. However, at this concentration cell viability initially decreased. Based on the results in example 4.4 an experiment was designed using one tenth of the N-acetylcysteine concentrations tested in example 4.4. The conditions for this spinner flask experiment were the same as in example 4.4. N-acetylcysteine was added in concentrations of 0 mM (control), 1 mM, 2 mM, 4 mM and 8 mM.

Table 44 shows the viable cell density over culture time, and Table 45 shows the viability over culture time.

TABLE 44

Viable cell density over culture time

| Day | Flask 1: 0 mM N-acetylcysteine | Flask 2: 0 mM N-acetylcysteine | Flask 3: 1 mM N-acetylcysteine | Flask 4: 1 mM N-acetylcysteine | Flask 5: 2 mM N-acetylcysteine |
|---|---|---|---|---|---|
| 0  | 2.75  | 3.45  | 3.64  | 3.22  | 4.10 |
| 3  | 25.05 | 22.42 | 19.25 | 19.32 | 17.42 |
| 4  | 35.98 | 31.42 | 25.45 | 24.56 | 24.96 |
| 5  | 45.43 | 37.56 | 31.16 | 29.23 | 27.28 |
| 6  | 40.04 | 39.41 | 29.67 | 28.35 | 28.45 |
| 7  | 35.55 | 33.25 | 27.71 | 27.03 | 26.65 |
| 8  | 31.56 | 26.22 | 24.63 | 22.33 | 22.49 |
| 9  | 27.15 | 23.04 | 22.23 | 20.23 | 19.11 |
| 10 | 23.26 | 19.88 | 21.06 | 17.74 | 18.07 |
| 11 |       |       |       |       | 15.48 |
| 12 |       |       |       |       |       |
| 13 |       |       |       |       |       |
| 14 |       |       |       |       |       |

| Day | Flask 6: 2 mM N-acetylcysteine | Flask 7: 4 mM N-acetylcysteine | Flask 8: 4 mM N-acetylcysteine | Flask 9: 8 mM N-acetylcysteine | Flask 10: 8 mM N-acetylcysteine |
|---|---|---|---|---|---|
| 0  | 2.96  | 3.13  | 2.80  | 2.97  | 3.54 |
| 3  | 19.03 | 17.39 | 16.39 | 11.24 | 10.17 |
| 4  | 28.40 | 24.80 | 23.71 | 14.47 | 13.88 |
| 5  | 34.21 | 28.06 | 26.92 | 20.68 | 18.64 |
| 6  | 37.05 | 30.62 | 29.54 | 25.59 | 23.13 |
| 7  | 32.55 | 30.66 | 26.94 | 28.22 | 26.12 |
| 8  | 28.99 | 24.75 | 23.84 | 30.00 | 30.77 |
| 9  | 27.75 | 22.25 | 21.71 | 27.45 | 28.63 |
| 10 | 23.05 | 20.06 | 19.67 | 27.14 | 27.90 |
| 11 | 20.75 | 16.79 | 16.70 | 26.42 | 29.60 |
| 12 |       |       |       | 26.39 | 25.62 |
| 13 |       |       |       | 21.46 | 22.29 |
| 14 |       |       |       | 30.47 | 32.41 |

TABLE 45

Viability over culture time

| Day | 0 mM N-acetylcysteine | 0 mM N-acetylcysteine | 1 mM N-acetylcysteine | 1 mM N-acetylcysteine | 2 mM N-acetylcysteine |
|---|---|---|---|---|---|
| 0  | 94.6 | 97.6 | 96.2 | 93.3 | 94.9 |
| 3  | 98.3 | 97.6 | 99.1 | 98.1 | 98.6 |
| 4  | 98.0 | 96.8 | 98.2 | 97.6 | 97.2 |
| 5  | 97.1 | 96.0 | 96.3 | 95.0 | 96.1 |
| 6  | 90.2 | 89.6 | 89.3 | 89.3 | 89.9 |
| 7  | 79.0 | 80.1 | 79.8 | 77.3 | 79.6 |
| 8  | 60.6 | 62.2 | 64.8 | 62.2 | 62.2 |
| 9  | 52.7 | 53.4 | 56.9 | 52.6 | 54.8 |
| 10 | 46.2 | 45.5 | 51.3 | 45.9 | 50.2 |
| 11 |      |      |      |      | 40.3 |
| 12 |      |      |      |      |      |
| 13 |      |      |      |      |      |
| 14 |      |      |      |      |      |

| Day | Flask 6: 2 mM N-acetylcysteine | Flask 7: 4 mM N-acetylcysteine | Flask 8: 4 mM N-acetylcysteine | Flask 9: 8 mM N-acetylcysteine | Flask 10: 8 mM N-acetylcysteine |
|---|---|---|---|---|---|
| 0  | 93.8 | 94.9 | 91.7 | 92.1 | 93.6 |
| 3  | 97.5 | 97.1 | 98.4 | 96.4 | 94.3 |
| 4  | 98.2 | 97.4 | 97.6 | 96.4 | 94.4 |
| 5  | 97.1 | 97.1 | 96.9 | 96.5 | 94.4 |
| 6  | 93.0 | 92.4 | 93.1 | 95.8 | 92.0 |
| 7  | 86.1 | 84.5 | 85.0 | 93.4 | 89.6 |
| 8  | 71.9 | 68.4 | 70.6 | 85.6 | 84.7 |
| 9  | 65.2 | 58.5 | 60.3 | 79.7 | 79.5 |
| 10 | 54.9 | 52.0 | 55.0 | 76.3 | 75.0 |
| 11 | 45.1 | 42.5 | 45.7 | 68.4 | 69.0 |
| 12 |      |      |      | 61.3 | 61.2 |
| 13 |      |      |      | 51.1 | 52.2 |
| 14 |      |      |      | 39.4 | 42.6 |

The control cultures (0 mM N-acetylcysteine) were terminated after 10 days of culture time. N-acetylcysteine could prolong culture longevity. The cultures grown in 8 mM N-acetylcysteine were terminated after 14 days of culture. Cultures grown in N-acetylcysteine had a lower maximum cell density compared to the control.

Table 46 shows the effect of N-acetylcysteine on final anti IL-18 titer.

TABLE 46

Anti IL-18 titer over culture time
Titer [mg/L]

| Day | Flask 1: 0 mM N-acetylcysteine | Flask 2: 0 mM N-acetylcysteine | Flask 3: 1 mM N-acetylcysteine | Flask 4: 1 mM aN-cetylcysteine | Flask 5: 2 mM N-acetylcysteine |
|---|---|---|---|---|---|
| 7  | 193.1 | 168.3 | 210.1 | 202.5 | 198.0 |
| 8  | 230.3 | 199.9 | 241.6 | 232.2 | 227.5 |
| 9  | 244.7 | 216.2 | 256.6 | 245.4 | 242.0 |
| 10 | 262.7 | 227.2 | 268.9 | 258.3 | 253.2 |
| 11 |       |       |       |       | 268.3 |
| 12 |       |       |       |       |       |
| 13 |       |       |       |       |       |
| 14 |       |       |       |       |       |

| Day | Flask 6: 2 mM N-acetylcysteine | Flask 7: 4 mM N-acetylcysteine | Flask 8: 4 mM N-acetylcysteine | Flask 9: 8 mM N-acetylcysteine | Flask 10: 8 mM N-acetylcysteine |
|---|---|---|---|---|---|
| 7  | 274.0 | 210.9 | 202.0 | 181.9 | 175.1 |
| 8  | 323.9 | 251.6 | 240.2 | 237.6 | 232.2 |
| 9  | 374.7 | 271.7 | 259.3 | 267.7 | 263.9 |
| 10 | 428.8 | 288.9 | 276.3 | 295.3 | 292.2 |
| 11 | 444.1 | 315.5 | 304.3 | 349.1 | 367.9 |
| 12 |       |       |       | 369.5 | 401.4 |
| 13 |       |       |       | 429.5 | 432.0 |
| 14 |       |       |       | 477.6 | 484.4 |

The average final anti IL-18 titer of the control cultures was 245 mg/L (very similar to 243 mg/L in example 4.4). The final anti IL-18 titer of the cultures grown in 8 mM N-acetylcysteine was 481 mg/L. This is an increase of 96% compared to the control.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference.

What is claimed is:

1. A fed-batch production method of making a human anti-TNFα antibody which comprises (1) a light chain variable region (LCVR) comprising the amino acid sequence of SEQ ID NO:1 and (2) a heavy chain variable region comprising the amino acid sequence of SEQ ID NO:2, said method comprising culturing Chinese Hamster Ovary (CHO) cells comprising a nucleic acid encoding said anti-TNFα antibody in a cell culture production medium in large-scale, wherein the glucose concentration in said medium is monitored, the glucose concentration in said medium decreases to below 2 g/L, and glucose is added to said medium when the glucose concentration in said medium decreases to below 2 g/L, or the glucose concentration in said medium is monitored and glucose is added to said medium to maintain the glucose concentration in said medium at a concentration of at least 2 g/L but no greater than 7 g/L, such that said anti-TNFα antibody is produced at a titer of at least 2 g/L in said cell culture production medium.

2. The method of claim 1, wherein said anti-TNFα antibody is produced at a titer of at least 2.5 g/L in said cell culture production medium.

3. The method of claim 1, wherein said anti-TNFα antibody is produced at a titer of at least 4 g/L in said cell culture production medium.

4. The method of claim 1, wherein said culturing lasts 9-15 days.

5. The method of claim 1, wherein said cell culture production medium is a serum-free medium.

6. The method of claim 5, wherein said serum-free medium comprises at least one non-animal-based hydrolysate.

7. The method of claim 6, wherein said serum-free medium comprises a recombinant growth factor, an osmolarity regulator, a pH buffer agent, glutamine, methotrexate, and a cell protectant.

8. The method of claim 5, wherein said serum-free medium comprises galactose and manganese.

9. The method of claim 1, wherein said CHO cells are cultured at a temperature ranging from 32° C. to 38° C.

10. The method of claim 9, wherein said temperature is maintained as a constant temperature throughout said production method, said temperature being selected from a temperature range of 32° C. to 38° C.

11. A fed-batch production method of making adalimumab, comprising culturing Chinese Hamster Ovary (CHO) cells comprising a nucleic acid encoding adalimumab in a cell culture production medium in large-scale, wherein glucose concentration in said medium is monitored, the glucose concentration in said medium decreases to below 2 g/L, and glucose is added to said medium when the glucose concentration in said medium decreases to below 2 g/L, or the glucose concentration in said medium is monitored and glucose is added to said medium to maintain the glucose concentration in said medium at a concentration of at least 2 g/L but no greater than 7 g/L, such that adalimumab is produced at a titer of at least 2 g/L in said cell culture production medium.

12. The method of claim 11, wherein adalimumab is produced at a titer of at least 2.5 g/L in said cell culture production medium.

13. The method of claim 11, wherein adalimumab is produced at a titer of at least 4 g/L in said cell culture production medium.

14. The method of claim 13, wherein said culturing lasts 9-15 days.

15. The method of claim 13, wherein during said culturing, said CHO cells reach a cell density of at least $2 \times 10^6$ cells/ml in said cell culture production medium.

16. The method of claim 13, wherein said culture production medium is a serum-free medium.

17. The method of claim 16, wherein said serum-free medium comprises at least one non-animal-based hydrolysate selected from a yeast-based hydrolysate, a soy-based hydrolysate, or a combination thereof.

18. The method of claim 17, wherein said serum-free medium comprises a recombinant growth factor, an osmolarity regulator, a pH buffer agent, glutamine, methotrexate, and a cell protectant.

19. The method of claim 16, wherein said serum-free medium comprises galactose and manganese.

20. The method of claim 13, wherein said CHO cells are cultured at a temperature ranging from 32° C. to 38° C.

21. The method of claim 20, wherein said temperature is maintained as a constant temperature throughout said production method, said temperature being selected from a temperature range of 32° C. to 38° C.

22. The method of claim 13, wherein said culturing lasts 9-15 days, and wherein said culture production medium is a serum-free medium and comprises at least one non-animal-based hydrolysate.

23. A fed-batch method of producing adalimumab, comprising expressing adalimumab in large-scale in Chinese Hamster Ovary (CHO) cells in a cell culture production medium, wherein said CHO cells comprise an expression vector encoding adalimumab, wherein glucose concentration in said medium is monitored, the glucose concentration in said medium drops to a level between 1 and 5 g/L, and then glucose is added to said medium to maintain the glucose concentration in said medium at no less than 1-5 g/L, and wherein adalimumab is produced at a titer of at least 2 g/L in said cell culture production medium.

24. The method of claim 23, wherein adalimumab is produced at a titer of at least 2.5 g/L in said cell culture production medium.

25. The method of claim 23, wherein adalimumab is produced at a titer of at least 4 g/L in said cell culture production medium.

26. The method of claim 23, wherein said culturing lasts 9-15 days.

27. The method of claim 26, wherein said culture production medium is a serum-free medium which comprises galactose and manganese.

28. The method of claim 27, wherein said serum-free medium comprises: (a) at least one non-animal-based hydrolysate selected from the group consisting of a yeast-based hydrolysate, a soy-based hydrolysate, and a combination thereof, (b) a recombinant growth factor, (c) an osmolarity regulator, (d) a pH buffer agent, (e) glutamine, (f) methotrexate, and (g) a cell protectant.

29. The method of claim 23, wherein said CHO cells are cultured at 32° C. to 38° C.

30. The method of claim 23, wherein said culturing lasts 9-15 days, and said CHO cells are cultured at 32° C. to 38° C., wherein said culture production medium is a serum-free medium, and wherein adalimumab is produced at a titer of at least 4 g/L in said cell culture production medium.

* * * * *